(12) United States Patent
Chen et al.

(10) Patent No.: US 10,532,053 B2
(45) Date of Patent: Jan. 14, 2020

(54) HISTONE DEACETYLASE INHIBITOR, AND PREPARATION METHOD AND USE THEREOF

(71) Applicant: GUANGDONG ZHONGSHENG PHARMACEUTICAL CO., LTD, Dongguan, Guangdong (CN)

(72) Inventors: Lijuan Chen, Dongguan (CN); Chaofeng Long, Dongguan (CN); Xiaoxin Chen, Dongguan (CN); Zhuowei Liu, Dongguan (CN); Haoyu Ye, Dongguan (CN); Chenshi Xie, Dongguan (CN)

(73) Assignee: Guangdong Zhongsheng Pharmaceutical Co., Ltd, Guangdong (CN)

( * ) Notice: Subject to any disclaimer, the term of this patent is extended or adjusted under 35 U.S.C. 154(b) by 11 days.

(21) Appl. No.: 15/558,370

(22) PCT Filed: Mar. 17, 2016

(86) PCT No.: PCT/CN2016/076624
§ 371 (c)(1),
(2) Date: Sep. 14, 2017

(87) PCT Pub. No.: WO2016/146074
PCT Pub. Date: Sep. 22, 2016

(65) Prior Publication Data
US 2018/0098990 A1      Apr. 12, 2018

(30) Foreign Application Priority Data

Mar. 18, 2015   (CN) .......................... 2015 1 0119932

(51) Int. Cl.
| | |
|---|---|
| *C07D 239/94* | (2006.01) |
| *C07D 401/12* | (2006.01) |
| *C07D 403/12* | (2006.01) |
| *A61K 31/517* | (2006.01) |
| *A61P 35/00* | (2006.01) |

(52) U.S. Cl.
CPC ............ *A61K 31/517* (2013.01); *A61P 35/00* (2018.01); *C07D 239/94* (2013.01); *C07D 401/12* (2013.01)

(58) Field of Classification Search
CPC ... C07D 239/94; C07D 401/12; C07D 403/12
See application file for complete search history.

(56) References Cited

PUBLICATIONS

Yang et al. J.Med. Chem. vol. 59,pp. 1455-1470 (Year: 2015).*

* cited by examiner

*Primary Examiner* — Emily A Bernhardt
(74) *Attorney, Agent, or Firm* — Lewis Roca Rothgerber Christie LLP

(57) ABSTRACT

A compound represented by Formula I or pharmaceutically acceptable salt thereof. The present invention relates to a 4-arylamino quinazoline hydroxamic acid compound having a histone deacetylase inhibitory activity, preparation method of the compound, pharmaceutical composition comprising the compound, and use of the compound and the pharmaceutical composition in the preparation of a histone deacetylase inhibitor medicine. The present invention aims at acquiring, via a medicine design and a synthetic technology, a series of selective histone deacetylase inhibitors having good hypotype selectivity and favorable pharmacokinetic characteristics based on optimization of an enzyme surface recognition region and connection region of 4-arylamino quinazoline, thus reducing an effect on normal tissues or cells while improving an antineoplastic activity of the normal tissues or cells.

In Formula I, the variables are as described herein.

11 Claims, 7 Drawing Sheets

(Top left: tumor growth curve; Top right: body weight changes in each group of the mice during treatment; bottom left: comparison of tumor weight in each group; bottom right: picture of the tumors treated with III-2 and the positive drug)

(Top left: tumor growth curve; Top right : body weight changes in each group of the mice during treatment; bottom left: comparison of tumor weight in each group; bottom right: tumor picture)

(GAPDH as an internal reference protein)

(GAPDH as an internal reference protein)

(Top left: tumor growth curve; top right: body weight changes in each group of the mice during treatment; bottom left: comparison of tumor weight in each group; bottom right: tumor picture)

(Top left: tumor growth curve; top right: body weight changes in each group of the mice during treatment; bottom left: comparison of tumor weight in each group; bottom right: tumor picture)

(Top left: tumor growth curve; top right: body weight changes in each group of the mice during treatment; bottom left: comparison of tumor weight in each group; bottom right: tumor picture)

(Top left: tumor growth curve; top right: body weight changes in each group of the mice during treatment; bottom left: comparison of tumor weight in each group; bottom right: tumor picture)

HISTONE DEACETYLASE INHIBITOR, AND PREPARATION METHOD AND USE THEREOF

CROSS-REFERENCE TO RELATED APPLICATION(S)

This application claims the benefit of International Patent Application No. PCT/CN2016/076624 filed on Mar. 17, 2016, which claims priority from Chinese Patent Application No. 201510119932.2 filed on Mar. 18, 2015, the content of all of which are incorporated herein by reference in their entirety.

TECHNICAL FIELD

The present invention belongs to the field of pharmaceuticals, specifically, the present invention relates to a novel 4-arylamino quinazoline hydroxamic acid compound having histone deacetylase inhibitory activity, a preparation method of the compound, a pharmaceutical composition comprising the compound, and the use of the compound and the pharmaceutical composition in the preparation of histone deacetylase inhibitor drugs.

BACKGROUND TECHNIQUES

Tumor is a kind of major diseases which threaten human health, and tumor treatment has been attracting close attention all around the world. Traditional chemotherapeutic drugs block cell division non-specifically and thereby cause cell death, which damages the normal cells of the human body while killing the tumor cells. In addition, quite a few cytotoxic drugs have a limited therapeutic scope, and can easily cause adverse reactions. Long-term administration of such drugs will also result in drug resistance.

In recent years, pathogenesis of tumors is further understood in the cellular and molecular level with the rapid development of combinatorial chemistry, molecular biotechnology, structure-based drug design, computer science and other technology, so that biotherapy for tumor has made great progress and reached a new era of molecular targeting therapy. Targeted anticancer drugs can target specific pathways, prevent tumor growth and reduce toxicity to normal cells. They have common characteristics which are: non-cytotoxic and tumor cell-targeting; having effect on cell regulation and stabilization; generally can not be achieved dose-limiting toxicity and maximum tolerated dose in clinical studies; able to kill tumor cells which are not sensitive to or having resistance to chemotherapy, and resulting in better efficacy in combination with the conventional treatments (radiotherapy, chemotherapy).

At present, many anti-tumor targeting sites have been found, and histone deacetylase and microtubule are important targets for developing new anti-cancer drugs.

Factors that cause tumor gene expression and abnormal activity of gene expression products are two major changes, i.e., genetic and epigenetic changes. Among them, epigenetics refers to a way of gene expression regulation, which affects transcriptional activity of a gene without involving DNA sequence changes. The molecular basis is mainly related to two aspects: one is DNA methylation modification, and the other is acetylation modification of chromatin histones. Acetylation and deacetylation of chromatin histones is one of the key processes in regulating gene expression, in which two enzymes, i.e., histone acetyltransferase (HAT) and histone deacetylase (HDAC), determine the degree of histone acetylation. Histone deacetylase is a kind of enzyme catalyzing removal of an acetyl group from lysine on histones. It plays a critical role in chromatin condensation and chromatin remodeling as well as in the gene regulation involved, and is an important part of epigenetic regulation. Abnormality of this regulation mechanism is closely related to tumorigenesis and tumor development. HDAC includes four classes and 18 different isoforms (Class I: HDAC1, 2, 3, 8; Class II: HDAC4, 5, 6, 7, 9, 10; Class III: Sirt1-7; Class IV: HDAC11). HDAC and histone acetyltransferase (HAT) regulate histone acetylation modification together, wherein, HAT acetylates specific lysine residues on histones, while HDAC is responsible for removal of such modification for the residues (J Mol Biol, 17-31, 2004, 388:1). Histone acetylation leads to loosening of the chromatin structure and thereby facilitates binding of other DNA-binding proteins, which has a deacetylation effect on multiple proteins in the cytoplasm, such as tumor suppressive factor p53, molecular chaperone proteins (Johnstone & Licht, Cancer Cell 4, 13-18, 2003), DNA damage repair protein Ku70 (Kerr et al., Cell Death and Differentiation 19, 1317-1327, 2012), microtubule protein a-tubulin. In tumors, coincidentally, the deacetylation of various proteins in the cytoplasm usually results in an impact of facilitating tumor resistance to chemotherapeutic drugs or escaping from programmed cell death, for example, deacetylation of p53 protein will promote the degradation of the protein (Kim et. al., Apoptosis 18, 110-120, 2013). Thus, small molecule drug development focusing on such important epigenetic inheritance affecting molecular targets such as HDAC, has becoming a hotspot nowadays in the field of tumor targeting therapy worldwide.

Histone deacetylase inhibitor is one of the hotspots in the field of anti-tumor drug research in recent years. Studies have shown that histone deacetylation inhibitor can effectively inhibit tumor cell proliferation, induce tumor cell differentiation and apoptosis and anti-tumor angiogenesis, and has inhibitory effect on migration, invasion and metastasis of tumor cells. It can be divided into four categories: (i) hydroxamic acid analogues, wherein the representative compounds include SAHA (licensed in 2006 for CTCL), Panobinostat (licensed in 2015 for treating multiple myeloma), Belinostat (Phase II clinical trials), and etc; (ii) benz amide analogues, wherein the representative compounds include Entinostat (Phase II clinical trials), Mocetinostat (Phase II clinical trials), Chidamide (licensed in 2014 for treating CTCL), and etc; (iii) cyclic peptides, wherein the representative compound includes Romidepsin (licensed in 2009 for CTCL); (iv) aliphatic carboxylic acids, wherein the representative compounds include Valproic acid (Phase III clinical trials), VP-101 (Phase II clinical trials), and etc. In addition, there are some inhibitors not embraced by the above-mentioned four categories, such as RG2833 (Phase I clinical trials), CXD101 (Phase II clinical trials) and etc., due to their particular molecular structures. (Giannini et al, Future Med. Chem. 4 (11), 1439-1460, 2012; Zhiming Li et al, Int. J. Biol. Sci. 10 (7), 757-770, 2014).

SAHA (also known as Vorinostat) falls into the hydroxamic acid category, and is the first histone deacetylase inhibitor licensed for treating cutaneous T cell lymphoma (CTCL), its application in treating solid tumors isalso in clinical trials. Chidamide was licensed in December 2014 for treating CTCL. In February 2015, Panobinostat was licensed for treating multiple myeloma. Romidepsin (FK228) developed by Celgene (USA) is a histone deacetylase inhibitor of the cyclic tetracycline category, and was licensed for treating CTCL in USA in 2009 and licensed by the US FDA in 2011 for treating recurrent/refractory peripheral T cells lymphoma (PTCL). Since SAHA, Panobinostat and FK228 are all non-selective inhibitors for HDAC and can inhibit a number of signaling pathways, they have strong toxic side effects. Clinical data have shown that SAHA can cause thrombosis and neurotoxicity, while for FK228, the incidence of medication-related adverse reactions above Phase III is up to 66% and it has cardiotoxicity. In addition, for both of the drugs SAHA and FK228, their absorption peak concentrations, which directly associated with clinical validity, are significantly higher than the concentrations required for inhibiting the growth of normal or tumor cells in vitro, and thereby result in direct cytotoxicity to normal cells. This increases toxic side effects of drug administration and severely limits their use in a comprehensive tumor treatment in combination with other drugs having different mechanisms. The pre-clinical animal trials of Entinostat (MS-275, a benzamide-based HDAC inhibitor developed by Bayer (Germany) and Syndax, USA) show that the compound has significant anticancer activity against hematopoietic cancer, lung cancer and rectal cancer, and is a selective HADC inhibitor. Since its elimination half-life in human body is approximately up to 100 hours and it has a huge difference in drug exposures, it exhibits poor tolerance in clinical trials in human and therefore the administration dose cannot be increased. Chidamide, a novel anti-cancer drug innovated in China, is the first licensed isoform selective histone deacetylase inhibitor for oral administration in the world, and also the first Chinese innovator drug whose patent right was authorized to USA and other developed countries, it is available in the market in December 2014. This marks that the core technologies and capability of integrating the whole process of structure-based molecular design, targeting site research, safety evaluation, clinical development, and industrialization in our country are significantly improved, and is a historic breakthrough in the pharmaceutical industry in China. So far, there are a variety of HDAC inhibitors available in the market or undergoing clinical evaluation.

The HDAC inhibitors of the hydroxamic acid category consist of enzyme surface recognition region (Cap), a linking region (Linker) and zinc ion binding region (ZBG). In order to find the compounds having better activity than SAHA inhibitor, the researchers have done considerable studies on such compounds, wherein the main research of the hydroxamic acid inhibitor is focused on structural optimization of the enzyme surface recognition region and the linking region while keeping the hydroxamic acid groups in the metal binding region unchanged, in order to discover the derivatives with stronger activity and higher selectivity and safety. How to improve anti-tumor activity as well as reduce the impact on normal tissues or cells is an issue of great concern.

SUMMARY OF THE INVENTION

In order to overcome the shortcomings of the prior art, the present invention aims to obtain a series of selective histone deacetylase inhibitors, which are based on optimization of 4-arylamino quinazoline as enzyme surface recognition region and linking region, and have isoform selectivity and good pharmacokinetic characteristics, by means of drug design and synthesis.

Thus, one objective of the present invention is to provide a novel 4-arylamino quinazoline hydroxamic acid compound having histone deacetylase inhibitory activity or pharmaceutically acceptable salts thereof, in order to improve anti-tumor activity as well as reduce the impact on normal tissues or cells.

Another objective of the present invention is to provide a preparation method of said novel compound or pharmaceutically acceptable salts thereof.

A further objective of the present invention is to provide a use of said novel compound or pharmaceutically acceptable salts thereof in pharmaceutical preparation.

A yet further objective of the present invention is to provide a pharmaceutical composition comprising said novel compound or pharmaceutically acceptable salts thereof as a main active ingredient.

In order to achieve the above objectives, the technical solutions adopted by the present invention are as follows:

The present invention provides a compound as shown in Formula (I) or pharmaceutically acceptable salts thereof:

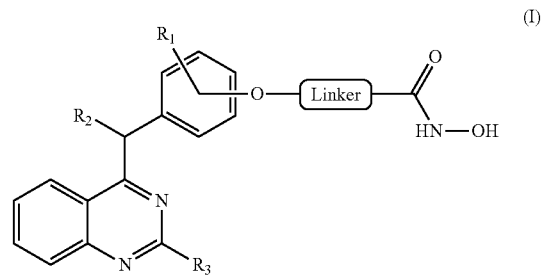

wherein, $R_1$ is one or more substituents;

$R_1$, $R_2$ and $R_3$ are each independently hydrogen, halogen, $C_{1-10}$ alkyl, oxygen-containing ether chain, nitrogen-containing alkane chain, $R_4O—$, $R_4OC(O)—$, $R_4C(O)O—$, $—NH_2$, $—NO_2$, hydroxyamino, $R_4NHR_5$, $R_4CONH—$, $R_4NHCO—$, guanidino, ureido, trifluoromethyl, $C_{1-10}$ alkylsulfonyl, substituted benzenesulfonyl, substituted phenyl, phenyl or heterocyclyl, wherein $R_4$ is $C_{1-10}$ alkyl or benzyl, $R_5$ is hydrogen or $C_{1-10}$ alkyl;

the Linker is a bond: $—(CH_2)_n—$, $—(CH_2)_nO—$, $—O(CH_2)_n—$, $—O(CH_2)_nC(O)—$, $—C(O)(CH_2)_nO—$, $—OC(O)(CH_2)_n—$, $—(CH_2)_nC(O)O—$, $—(CH_2)_nC(O)NH—$, $—C(O)NH(CH_2)_n—$, $—(CH_2)_n$ sulfonyl-, -sulfonyl $(CH_2)_n—$, wherein n is an integer from 1 to 10; or is substituted benzenesulfonyl, substituted phenyl, phenyl or heterocyclyl;

preferably, the substituted phenyl comprises 1 to 4 substituents on the benzene ring, the substituent of the substituted phenyl is halogen, $—OH$, $—NO_2$, cyano, alkoxy, $C_{1-4}$ alkyl or amino group;

preferably, the heterocyclyl is a saturated or unsaturated five-membered heterocyclyl or six-membered heterocyclyl comprising one or more heteroatoms selected from the group consisting of nitrogen, oxygen or sulfur;

preferably, the halogen is fluorine, chlorine, bromine or iodine.

In the above-mentioned groups, the $C_{1-10}$ alkyl is a linear, branched or cyclic saturated hydrocarbon containing 1-10 carbon atoms, wherein the alkyl can be substituted (e.g., can be pyrrolidin-1-yl-$C_{2-10}$ alkyl, morpholin-1-yl-$C_{2-10}$ alkyl or piperazin- 1-$C_{2-10}$ alkyl) or unsubstituted; preferably, the $C_{1-10}$ alkyl employed in the present invention is methyl, ethyl, propyl, isopropyl, cyclopropyl, butyl, isobutyl, sec-butyl, tert-butyl, cyclobutyl, pentyl, cyclopentyl, hexyl, cyclohexyl, heptyl, octyl, nonyl or decyl;

preferably, the R₄O— employed in the present invention is benzyloxy, pyrrolidin-1-yl-$C_{2-10}$ alkoxy, morpholin-1-yl-$C_{2-10}$ alkoxy or piperazin-1-$C_{2-10}$ alkoxy;

preferably, the R₄OC(O)— employed in the present invention is ethoxycarbonyl, propoxycarbonyl, butoxycarbonyl, isobutoxycarbonyl, pentyloxycarbonyl, hexyloxycarbonyl, heptyloxycarbonyl, octyloxycarbonyl, nonyloxycarbonyl or decyloxycarbonyl;

the R₄C(O)O— employed in the present invention is ethyl ester, propyl ester, butyl ester, isobutyl ester, pentyl ester, hexyl ester, heptyl ester, octyl ester, nonyl ester or decyl ester;

preferably, the R₄NHR₅ employed in the present invention is aminoethyl, 1-aminopropyl, 2-aminopropyl, 1-aminobutyl, 2-aminobutyl, 1-aminopentyl, 1-aminohexyl, 1-aminoheptyl, 1-aminooctyl, 1-aminononyl, 1-aminodecyl, N-methylamino, N-ethylamino, N-propylamino, N-butylamino, N-pentylamino, N-hexylamino, N-heptylamino, N-octylamino, N-nonylamino or N-decylamino;

preferably, the R₄CONH— employed in the present invention is acetamido, propionamido, butyrylamido, isobutyrylamido, pentanamido, hexanamido, heptanamido, octanamido, nonanamido or decanamido;

the $C_{1-10}$ alkylsulfonyl is a $C_{1-10}$ alkyl as defined above linked to a sulfonyl and is attached to a Formula (I) via the sulfonyl; preferably, the $C_{1-10}$ alkylsulfonyl employed in the present invention is methylsulfonyl, ethylsulfonyl, propylsulfonyl, isopropylsulfonyl, butylsulfonyl, pentylsulfonyl, hexylsulfonyl, heptylsulfonyl, octylsulfonyl, nonylsulfonyl or decylsulfonyl;

the pharmaceutically acceptable salts are hydrochloride, hydrobromide, sulfate, acetate, lactate, tartrate, tannate, citrate, trifluoroacetate, malate, maleate, succinate, p-toluenesulfonate or methanesulfonate.

Preferably, the present invention provides a compound as shown in Formula (II) or pharmaceutically acceptable salts thereof:

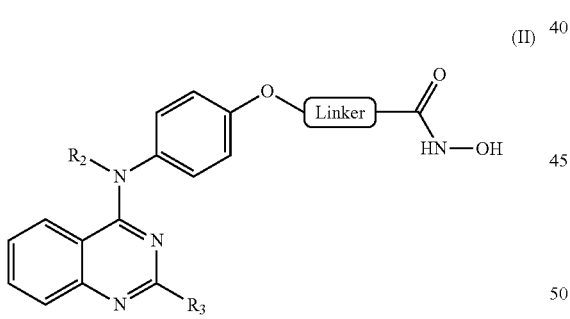

(II)

wherein, R₂ and R₃ are each independently hydrogen, halogen, $C_{1-10}$ alkyl, oxygen-containing ether chain, nitrogen-containing alkane chain, R₄O—, R₄OC(O)—, R₄C(O)O—, —NH₂, —NO₂, hydroxyamino, R₄NHR₅, R₄CONH—, R₄NHCO—, guanidino, ureido, trifluoromethyl, $C_{1-10}$ alkylsulfonyl, substituted benzenesulfonyl, substituted phenyl, phenyl or heterocyclyl, wherein R₄ is $C_{1-10}$ alkyl or benzyl, R₅ is hydrogen or $C_{1-10}$ alkyl; preferably, R₂ and R₃ are each independently hydrogen or $C_{1-6}$ alkyl; more preferably, R₂ and R₃ are each independently hydrogen or $C_{1-4}$ alkyl; most preferably, R₂ and R₃ are each independently hydrogen or methyl;

the Linker is a bond: —(CH₂)$_n$—, —(CH₂)$_n$O—, —O(CH₂)$_n$—, —O(CH₂)$_n$C(O)—, —C(O)(CH₂)$_n$O—, —OC(O)(CH₂)$_n$—, —(CH₂)$_n$C(O)O—, —(CH₂)$_n$C(O)NH—, —C(O)NH(CH₂)$_n$—, —(CH₂)$_n$ sulfonyl, -sulfonyl (CH₂)$_n$—, wherein n is an integer from 1 to 10; or is substituted benzenesulfonyl, substituted phenyl, phenyl or heterocyclyl;

preferably, the substituted phenyl comprises 1 to 4 substituents on the benzene ring, wherein the substituent of the substituted phenyl is halogen, —OH, —NO₂, cyano, alkoxy, $C_{1-4}$ alkyl or amino group;

preferably, the heterocyclyl is a saturated or unsaturated five-membered heterocyclyl or six-membered heterocyclyl comprising one or more heteroatoms selected from the group consisting of nitrogen, oxygen or sulfur;

preferably, the halogen is fluorine, chlorine, bromine or iodine.

Preferably, the Linker is —(CH₂)$_n$—, wherein n is an integer from 1 to 10; or is —(CH₂)$_m$ phenyl-, -phenyl (CH₂)$_m$—, wherein m is an integer from 0 to 5; or is saturated or unsaturated five-membered heterocyclyl or six-membered heterocyclyl comprising 1 or 2 heteroatoms, and the heteroatom is selected from nitrogen; more preferably, the Linker is —(CH₂)$_n$—, wherein n is an integer from 1 to 5; or —(CH₂)$_m$ phenyl-, wherein m is an integer from 0 to 5; or is saturated or unsaturated six-membered heterocyclyl comprising 1 or 2 nitrogen atoms, preferably unsaturated six-membered heterocyclyl comprising 1 nitrogen atom;

preferably, the pharmaceutically acceptable salts are hydrochloride, hydrobromide, sulfate, acetate, lactate, tartrate, tannate, citrate, trifluoroacetate, malate, maleate, succinate, p-toluenesulfonate or methanesulfonate.

According the embodiments of the present invention, the above-mentioned compound of Formula (I) or the compound of Formula (II) or pharmaceutically acceptable salts thereof are selected from the group consisting of:

(II-1) N-hydroxy-2-(4-(methyl(2-methyl-4-quinazolinyl)amino)phenoxy)acetamide

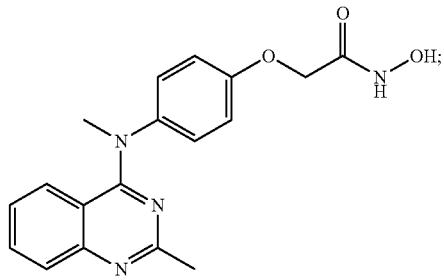 [SMILES: Cc1nc(N(C)c2ccc(OCC(=O)NO)cc2)c2ccccc2n1]

(II-2) N-hydroxy-4-(4-(methyl(2-methyl-4-quinazolinyl)amino)phenoxy)butanamide

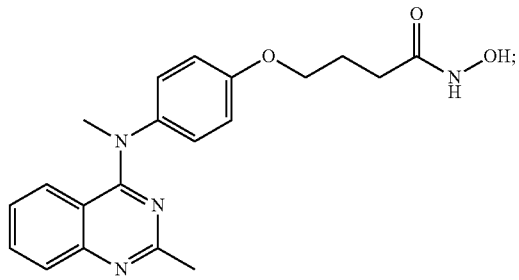 [SMILES: Cc1nc(N(C)c2ccc(OCCCC(=O)NO)cc2)c2ccccc2n1]

(II-3) N-hydroxy-5-(4-(methyl(2-methyl-4-quinazolinyl)amino)phenoxy)pentanamide

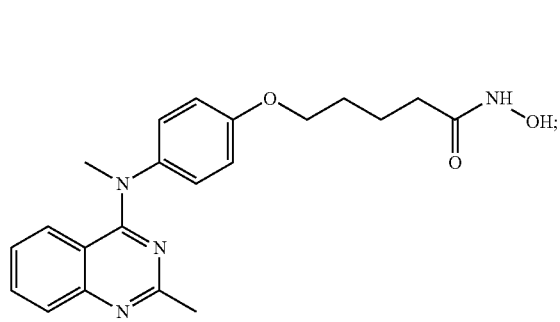 [SMILES: Cc1nc(N(C)c2ccc(OCCCCC(=O)NO)cc2)c2ccccc2n1]

(II-4) N-hydroxy-6-(4-(methyl(2-methyl-4-quinazolinyl)amino)phenoxy)hexanamide

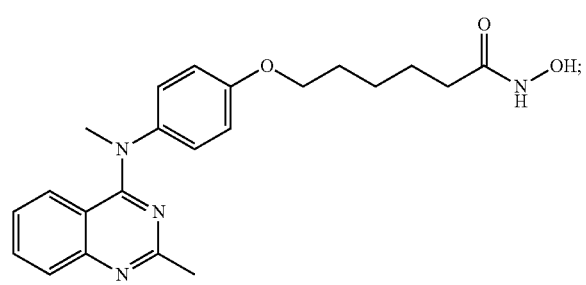

(II-5) N-hydroxy-4-((4-(methyl(2-methyl-4-quinazolinyl)amino)phenoxy)methyl)benzamide

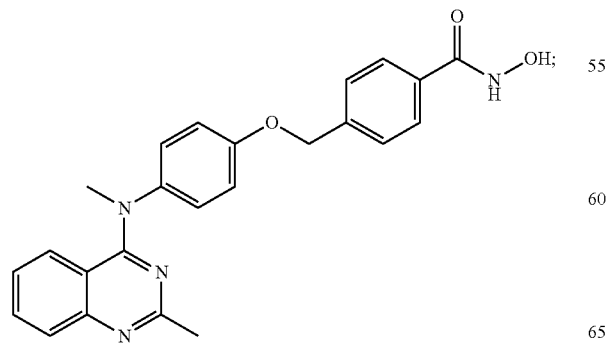

(II-6) N-hydroxy-4-(4-(methyl(2-methyl-4-quinazolinyl)amino)phenoxy)benzamide

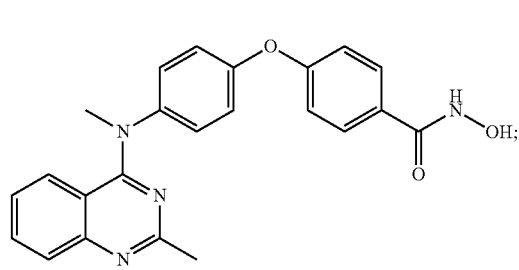 [SMILES: Cc1nc(N(C)c2ccc(Oc3ccc(C(=O)NO)cc3)cc2)c2ccccc2n1]

(II-7) N-hydroxy-6-(4-(methyl(2-methyl-4-quinazolinyl)amino)phenoxy)nicotinamide

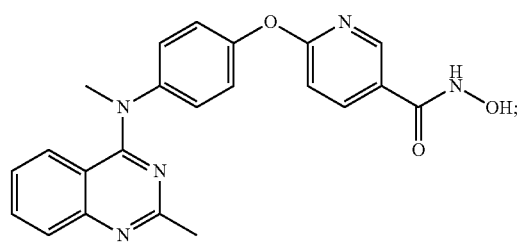 [SMILES: Cc1nc(N(C)c2ccc(Oc3ccc(C(=O)NO)cn3)cc2)c2ccccc2n1]

(II-8) N-hydroxy-5-(4-(methyl(2-methyl-4-quinazolinyl)amino)phenoxy)picolinamide

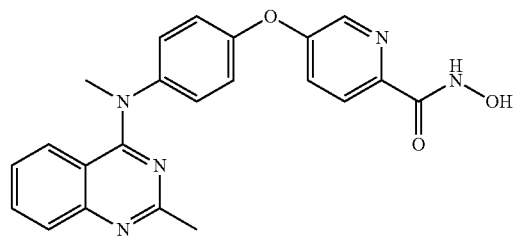 [SMILES: Cc1nc(N(C)c2ccc(Oc3ccc(C(=O)NO)nc3)cc2)c2ccccc2n1]

(II-9) N-hydroxy-2-(4-(methyl(2-methyl-4-quinazolinyl)amino)phenoxy)pyrimidin-5-amide

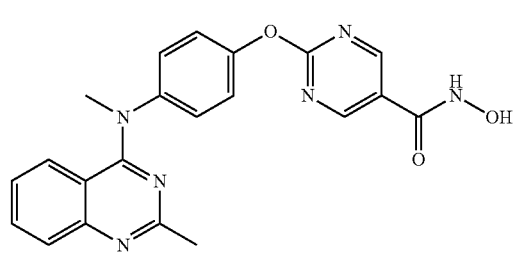

(II-10) N-hydroxy-5-(4-(methyl(2-methyl-4-quinazolinyl)amino)phenoxy)pyrimidin-2-amide

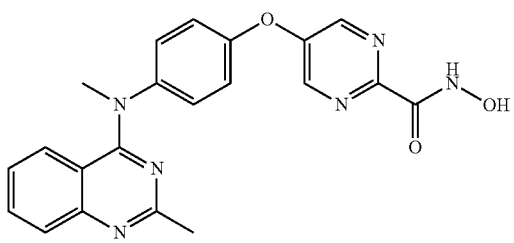 [SMILES: Cc1nc(N(C)c2ccc(Oc3cnc(C(=O)NO)nc3)cc2)c2ccccc2n1]

(II-11) N-hydroxy-5-(4-(methyl(2-methyl-4-quinazolinyl)amino)phenoxypyrazine-2-amide

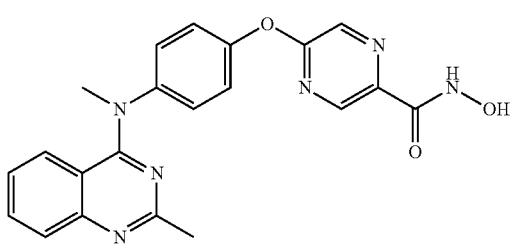 [SMILES: Cc1nc(N(C)c2ccc(Oc3cnc(C(=O)NO)cn3)cc2)c2ccccc2n1]

(II-12) N-hydroxy-2-(4-(methyl(4-quinazolinyl)amino)phenoxy)acetamide

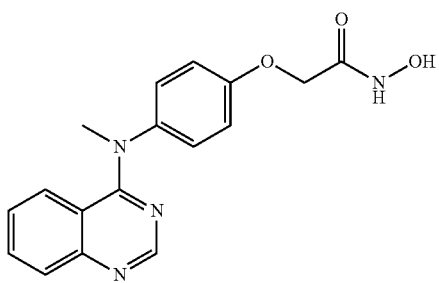 [SMILES: CN(c1ccc(OCC(=O)NO)cc1)c1ncnc2ccccc12]

(II-13) N-hydroxy-4-(4-(methyl(4-quinazolinyl)amino)phenoxy)butanamide

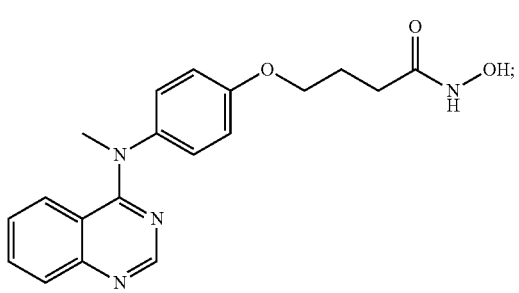 [SMILES: CN(c1ccc(OCCCC(=O)NO)cc1)c1ncnc2ccccc12]

(II-14) N-hydroxy-5-(4-(methyl(4-quinazolinyl)amino)phenoxy)pentanamide

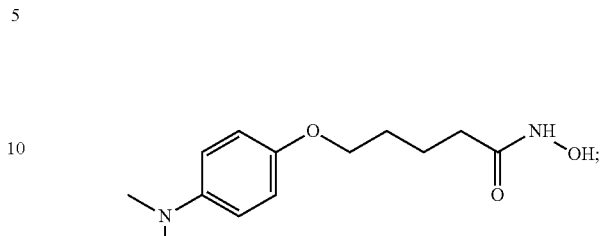

(II-15) N-hydroxy-6-(4-(methyl(4-quinazolinyl)amino)phenoxy)hexanamide

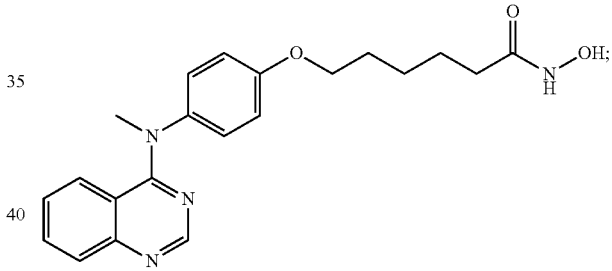

(II-16) N-hydroxy-4-((4-(methyl(4-quinazolinyl)amino)phenoxy)methyl)benzamide

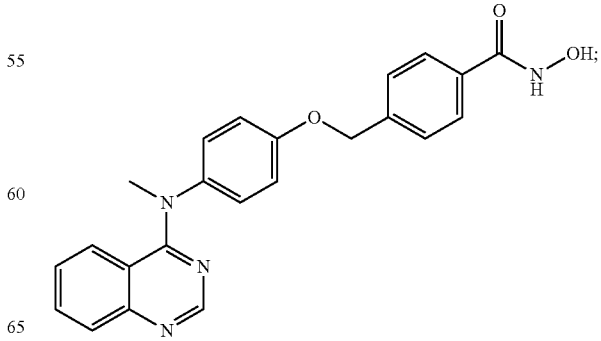

(II-17) N-hydroxy-4-(4-(methyl(4-quinazolinyl)amino)phenoxy)benzamide

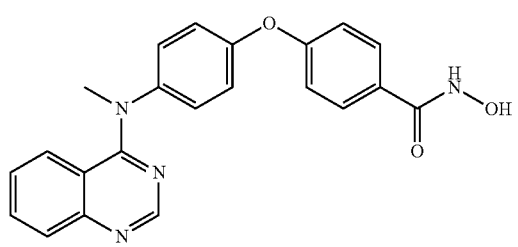 [SMILES: CN(c1ccc(Oc2ccc(C(=O)NO)cc2)cc1)c1ncnc2ccccc12]

(II-18) N-hydroxy-6-(4-(methyl(4-quinazolinyl)amino)phenoxy)nicotinamide

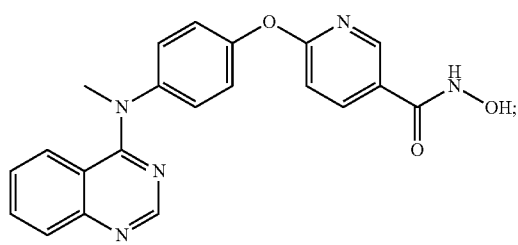 [SMILES: CN(c1ccc(Oc2ccc(C(=O)NO)cn2)cc1)c1ncnc2ccccc12]

(II-19) N-hydroxy-5-(4-(methyl(4-quinazolinyl)amino)phenoxypicolinamide

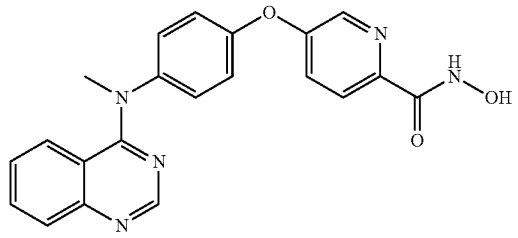 [SMILES: CN(c1ccc(Oc2ccc(C(=O)NO)nc2)cc1)c1ncnc2ccccc12]

(II-20) N-hydroxy-2-(4-(methyl(4-quinazolinyl)amino)phenoxy)pyrimidin-5-formamide

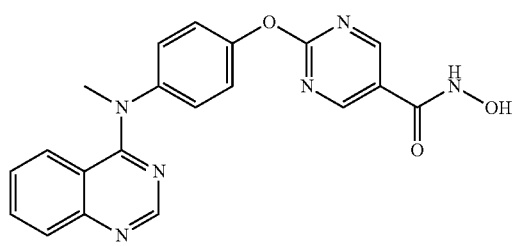 [SMILES: CN(c1ccc(Oc2ncc(C(=O)NO)cn2)cc1)c1ncnc2ccccc12]

(II-21) N-hydroxy-5-(4-(methyl(4-quinazolinyl)amino)phenoxy)pyrimidin-2-formamide

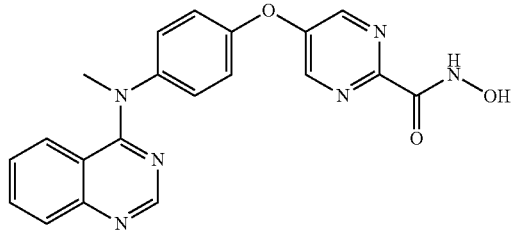 [SMILES: CN(c1ccc(Oc2cnc(C(=O)NO)nc2)cc1)c1ncnc2ccccc12]

(II-22) N-hydroxy-5-(4-(methyl(4-quinazolinyl)amino)phenoxy)pyrazin-2-formamide

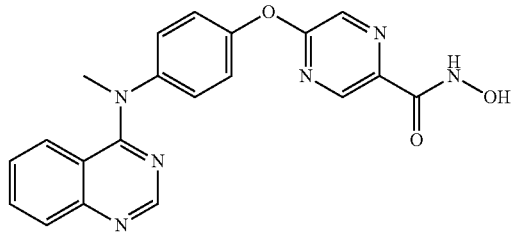

(II-23) N-hydroxy-2-(4-((2-methyl-4-quinazolinyl)amino)phenoxy)acetamide

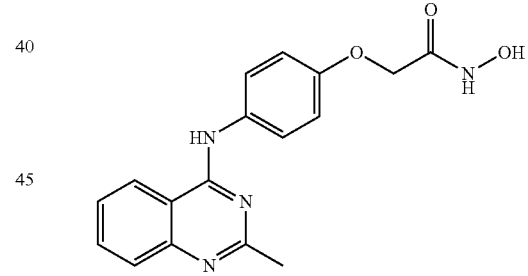

(II-24) N-hydroxy-3-(4-((2-methyl-4-quinazolinyl)amino)phenoxy)propionamide

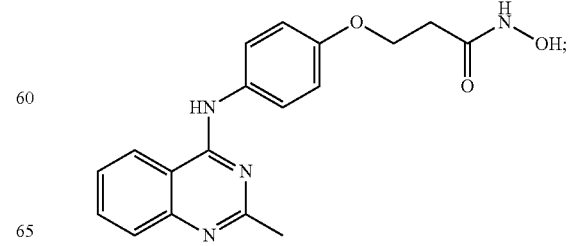

(II-25) N-hydroxy-4-(4-((2-methyl-4-quinazolinyl)amino)phenoxy)butanamide

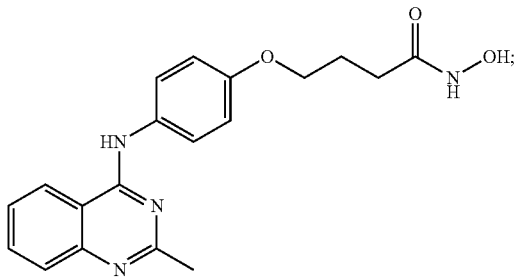 [SMILES: Cc1nc(Nc2ccc(OCCCC(=O)NO)cc2)c2ccccc2n1]

(II-26) N-hydroxy-5-(4-((2-methyl-4-quinazolinyl)amino)phenoxy)pentanamide

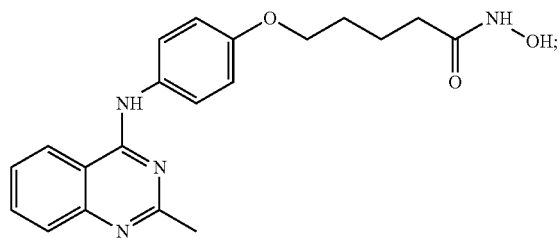 [SMILES: Cc1nc(Nc2ccc(OCCCCC(=O)NO)cc2)c2ccccc2n1]

(II-27) N-hydroxy-6-(4-((2-methyl-4-quinazolinyl)amino)phenoxy)hexanamide

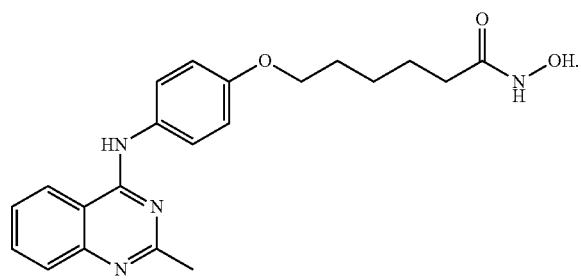 [SMILES: Cc1nc(Nc2ccc(OCCCCCC(=O)NO)cc2)c2ccccc2n1]

Preferably, the present invention provides a compound as shown in Formula (III) or pharmaceutically acceptable salts thereof:

(III)

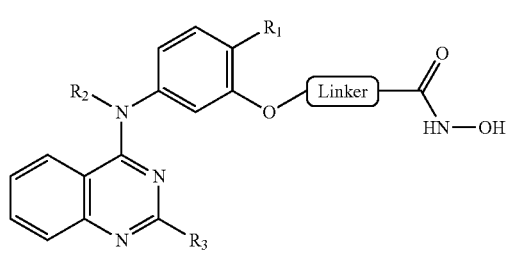

wherein, $R_1$, $R_2$ and $R_3$ are each independently hydrogen, halogen, $C_{1-10}$ alkyl, oxygen-containing ether chain, nitrogen-containing alkane chain, $R_4O$—, $R_4OC(O)$—, $R_4C(O)O$—, —$NH_2$, —$NO_2$, hydroxyamino, $R_4NHR_5$, $R_4CONH$—, $R_4NHCO$—, guanidino, ureido, trifluoromethyl, $C_{1-10}$ alkylsulfonyl, substituted benzenesulfonyl, substituted phenyl, phenyl or heterocyclyl, wherein $R_4$ is $C_{1-10}$ alkyl or benzyl, $R_5$ is hydrogen or $C_{1-10}$ alkyl; preferably, $R_1$ is hydrogen or $C_{1-6}$ alkoxy; more preferably, $R_1$ is hydrogen or $C_{1-4}$ alkoxy; most preferably, $R_1$ is hydrogen or methoxy; preferably, $R_2$ and $R_3$ are independently hydrogen or $C_{1-6}$ alkyl; more preferably, $R_2$ and $R_3$ are independently hydrogen or $C_{1-4}$ alkyl; most preferably, $R_2$ and $R_3$ are independently hydrogen or methyl;

the Linker is a bond: —$(CH_2)_n$—, —$(CH_2)_nO$—, —$O(CH_2)_n$—, —$O(CH_2)_nC(O)$—, —$C(O)(CH_2)_nO$—, —$OC(O)(CH_2)_n$—, —$(CH_2)_nC(O)O$—, —$(CH_2)_nC(O)NH$—, —$C(O)NH(CH_2)_n$—, —$(CH_2)_n$ sulfonyl-, -sulfonyl $(CH_2)_n$—, wherein n is an integer from 1 to 10; or is substituted benzenesulfonyl, substituted phenyl, phenyl or heterocyclyl;

preferably, the substituted phenyl comprises 1 to 4 substituents on the benzene ring, wherein the substituent of the substituted phenyl is halogen, —OH, —$NO_2$, cyano, alkoxy, $C_{1-4}$ alkyl or amino group;

preferably, the heterocyclyl is a saturated or unsaturated five-membered heterocyclyl or six-membered heterocyclyl comprising one or more heteroatoms selected from the group consisting of nitrogen, oxygen or sulfur;

preferably, the halogen is fluorine, chlorine, bromine or iodine.

preferably, the Linker is —$(CH_2)_nO$—, —$O(CH_2)_n$—, wherein n is an integer from 1 to 10; more preferably, the Linker is —$(CH_2)_nO$—, wherein n is an integer from 1 to 10; most preferably, the Linker is —$(CH_2)_nO$—, wherein n is an integer from 1 to 5;

preferably, the pharmaceutically acceptable salts are hydrochloride, hydrobromide, sulfate, acetate, lactate, tartrate, tannate, citrate, trifluoroacetate, malate, maleate, succinate, p-toluenesulfonate or methanesulfonate.

According the embodiments of the present invention, the above-mentioned compound of Formula (I) or the compound of Formula (III) or pharmaceutically acceptable salts thereof are selected from the group consisting of:

(III-1) N-hydroxy-2-(2-methoxy-5-(methyl(2-methyl-4-quinazolinyl)amino)phenoxy) acetamide

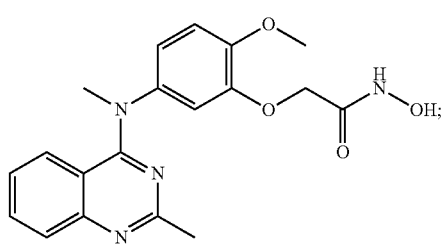 [SMILES: COc1ccc(N(C)c2nc(C)nc3ccccc23)cc1OCC(=O)NO]

(III-2) N-hydroxy-4-(2-methoxy-5-(methyl(2-methyl-4-quinazolinyl)amino)phenoxy) butanamide

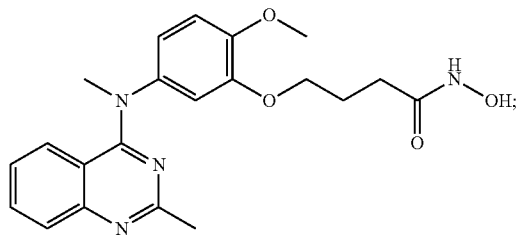 [SMILES: COc1ccc(N(C)c2nc(C)nc3ccccc23)cc1OCCCC(=O)NO]

(III-3) N-hydroxy-5-(2-methoxy-5-(methyl(2-methyl-4-quinazolinyl)amino)phenoxy) pentanamide

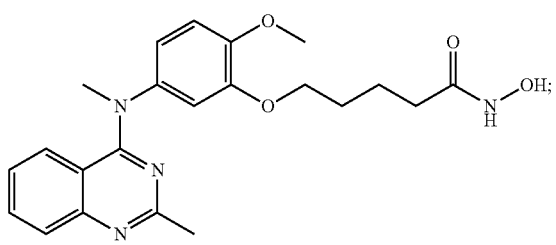 [SMILES: COc1ccc(N(C)c2nc(C)nc3ccccc23)cc1OCCCCC(=O)NO]

(III-4) N-hydroxy-6-(2-methoxy-5-(methyl(2-methyl-4-quinazolinyl)amino)phenoxy)hexanamide

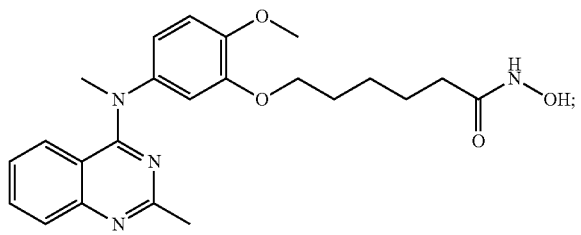 [SMILES: COc1ccc(N(C)c2nc(C)nc3ccccc23)cc1OCCCCCC(=O)NO]

(III-5) N-hydroxy-4-((2-methoxy-5-(methyl(2-methyl-4-quinazolinyl)amino)phenoxy)methyl) benzamide

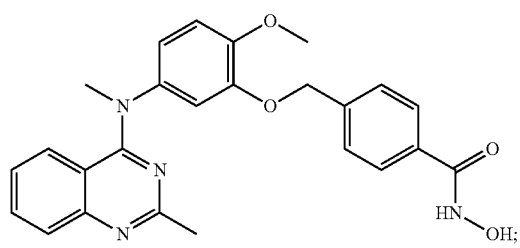 [SMILES: COc1ccc(N(C)c2nc(C)nc3ccccc23)cc1OCc1ccc(C(=O)NO)cc1]

(III-6) N-hydroxy-4-(2-methoxy-5-(methyl(2-methyl-4-quinazolinyl)amino)phenoxy)benzamide

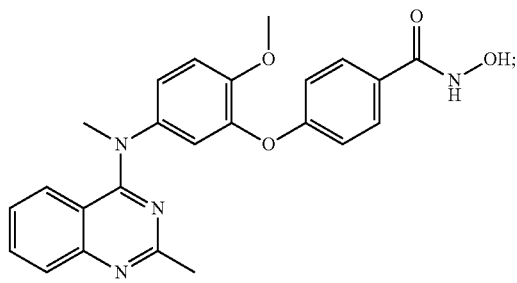

(III-7) N-hydroxy-6-(2-methoxy-5-(methyl(2-methyl-4-quinazolinyl)amino)phenoxy)nicotinamide

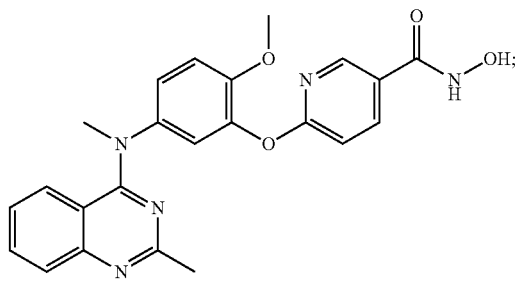 [SMILES: COc1ccc(N(C)c2nc(C)nc3ccccc23)cc1Oc1ccc(C(=O)NO)cn1]

(III-8) N-hydroxy-5-(2-methoxy-5-(methyl(2-methyl-4-quinazolinyl)amino)phenoxy)picolinamide

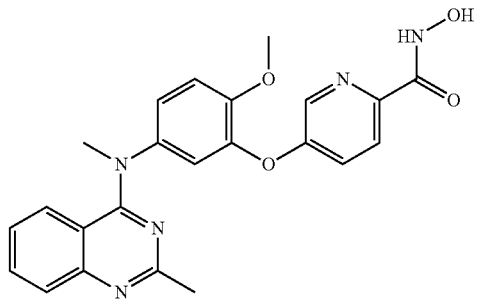

(III-9) N-hydroxy-2-(2-methoxy-5-(methyl(2-methyl-4-quinazolinyl)amino)phenoxy)pyrimidin-5-formamide

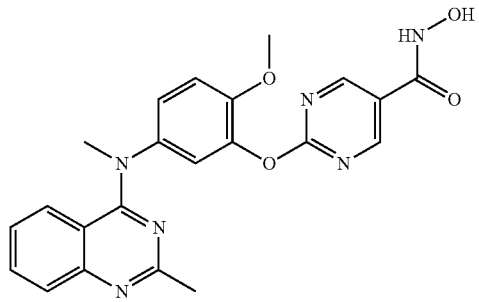 [SMILES: COc1ccc(N(C)c2nc(C)nc3ccccc23)cc1Oc1ncc(C(=O)NO)cn1]

(III-10) N-hydroxy-5-(2-methoxy-5-(methyl(2-methyl-4-quinazolinyl)amino)phenoxy)pyrimidin-2-formamide

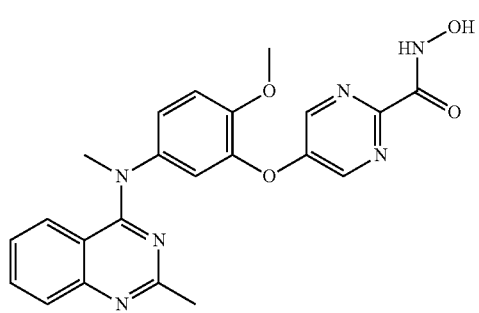 [SMILES: COc1ccc(N(C)c2nc(C)nc3ccccc23)cc1Oc1cnc(C(=O)NO)nc1]

(III-11) N-hydroxy-5-(2-methoxy-5-(methyl(2-methyl-4-quinazolinyl)amino)phenoxy)pyrazin-2-formamide

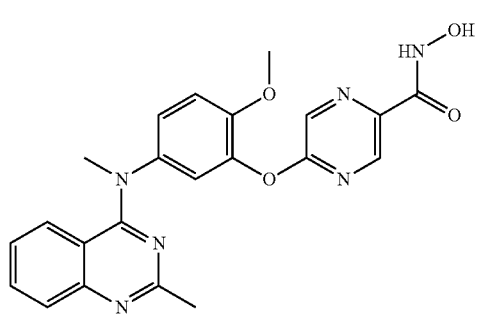

(III-12) N-hydroxy-2-(3-(methyl(2-methyl-4-quinazolinyl)amino)phenoxy)acetamide

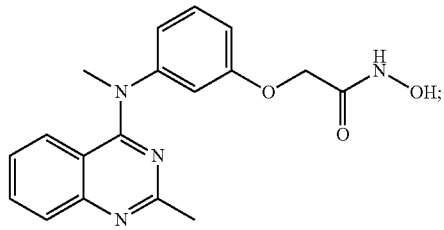 [SMILES: Cc1nc(N(C)c2cccc(OCC(=O)NO)c2)c2ccccc2n1]

(III-13) N-hydroxy-4-(3-(methyl(2-methyl-4-quinazolinyl)amino)phenoxy)butanamide

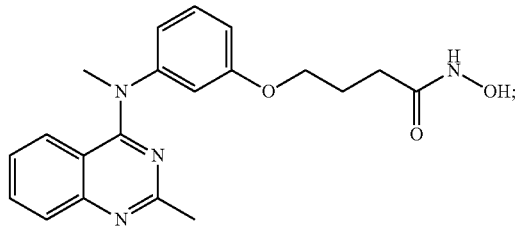 [SMILES: Cc1nc(N(C)c2cccc(OCCCC(=O)NO)c2)c2ccccc2n1]

(III-14) N-hydroxy-5-(3-(methyl(2-methyl-4-quinazolinyl)amino)phenoxy)pentanamide

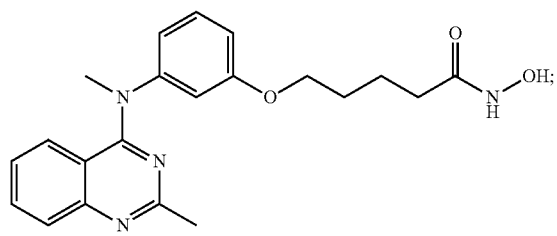 [SMILES: Cc1nc(N(C)c2cccc(OCCCCC(=O)NO)c2)c2ccccc2n1]

(III-15) N-hydroxy-6-(3-(methyl(2-methyl-4-quinazolinyl)amino)phenoxy)hexanamide

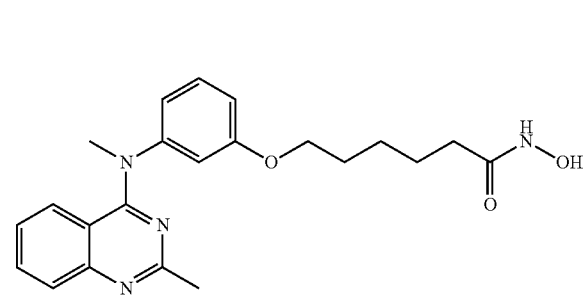 [SMILES: Cc1nc(N(C)c2cccc(OCCCCCC(=O)NO)c2)c2ccccc2n1]

(III-16) N-hydroxy-4-((3-(methyl(2-methyl-4-quinazolinyl)amino)phenoxy)methyl)benzamide

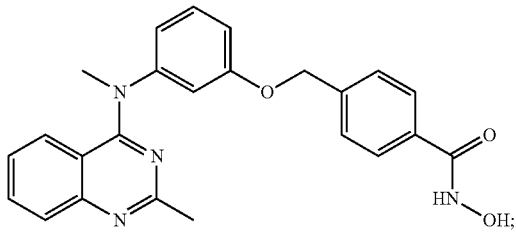

(III-17) N-hydroxy-4-(3-(methyl(2-methyl-4-quinazolinyl)amino)phenoxy)benzamide

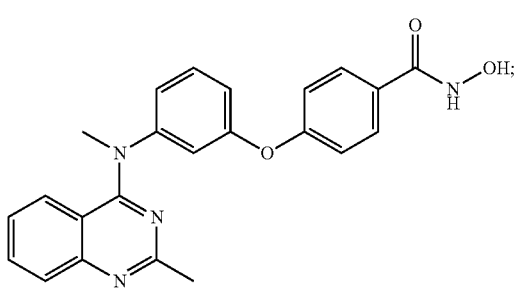 [SMILES: Cc1nc(N(C)c2cccc(Oc3ccc(C(=O)NO)cc3)c2)c2ccccc2n1]

(III-18) N-hydroxy-6-(3-(methyl(2-methyl-4-quinazolinyl)amino)phenoxy)nicotinamide

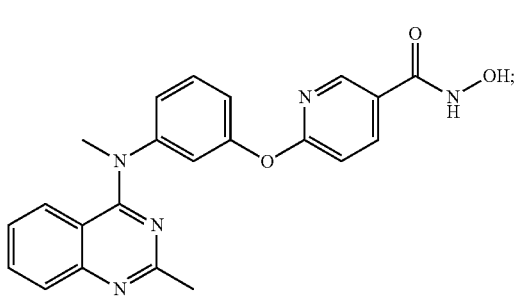 [SMILES: Cc1nc(N(C)c2cccc(Oc3ccc(C(=O)NO)cn3)c2)c2ccccc2n1]

(III-19) N-hydroxy-5-(3-(methyl(2-methyl-4-quinazolinyl)amino)phenoxy)picolinamide

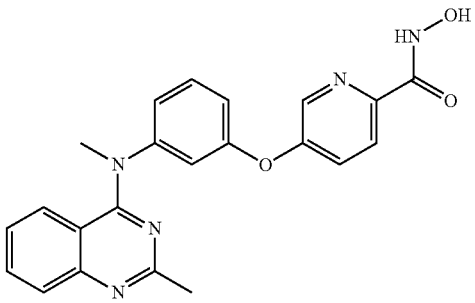 [SMILES: Cc1nc(N(C)c2cccc(Oc3ccc(C(=O)NO)nc3)c2)c2ccccc2n1]

(III-20) N-hydroxy-2-(3-(methyl(2-methyl-4-quinazolinyl)amino)phenoxy)pyrimidin-5-formamide

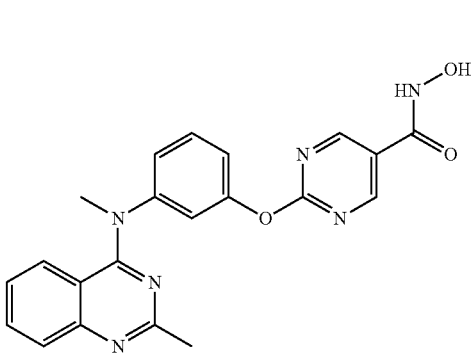 [SMILES: Cc1nc(N(C)c2cccc(Oc3ncc(C(=O)NO)cn3)c2)c2ccccc2n1]

(III-21) N-hydroxy-5-(3-(methyl(2-methyl-4-quinazolinyl)amino)phenoxy)pyrimidin-2-formamide

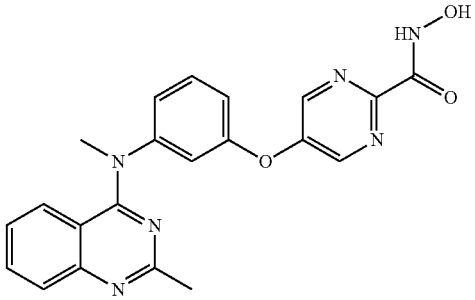

(III-22) N-hydroxy-5-(3-(methyl(2-methyl-4-quinazolinyl)amino)phenoxy)pyrazin-2-formamide

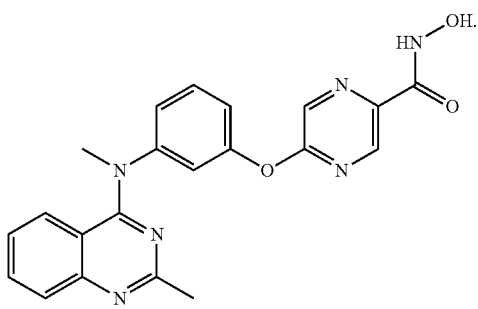 [SMILES: Cc1nc(N(C)c2cccc(Oc3cnc(C(=O)NO)cn3)c2)c2ccccc2n1]

Preferably, the present invention provides a compound as shown in Formula (IV) or pharmaceutically acceptable salts thereof:

(IV)

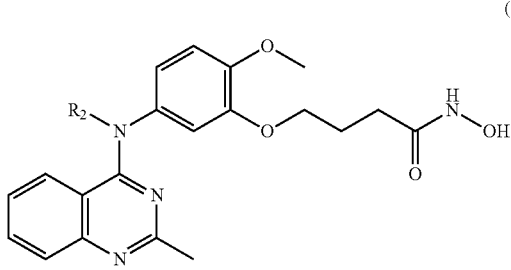

wherein, $R_2$ is independently hydrogen, halogen, $C_{1-10}$ alkyl, oxygen-containing ether chain, nitrogen-containing alkane chain, $R_4O-$, $R_4OC(O)-$, $R_4C(O)O-$, $-NH_2$, $-NO_2$, hydroxyamino, $R_4-O-CH_2-$, $R_4-O-CH_2-O-CH_2-$, $R_4NHR_5$, $R_4CONH-$, $R_4NHCO-$, guanidino, ureido, trifluoromethyl, $C_{1-10}$ alkylsulfonyl, substituted benzenesulfonyl, substituted phenyl, phenyl or heterocyclyl, wherein $R_4$ is $C_{1-10}$ alkyl or benzyl, $R_5$ is hydrogen or $C_{1-10}$ alkyl; preferably, $R_2$ is independently hydrogen or $C_{1-6}$ alkyl;

preferably, the pharmaceutically acceptable salts are hydrochloride, hydrobromide, sulfate, acetate, lactate, tartrate, tannate, citrate, trifluoroacetate, malate, maleate, succinate, p-toluenesulfonate or methanesulfonate.

According the embodiments of the present invention, the above-mentioned compound of Formula (I) or the compound of Formula (IV) or pharmaceutically acceptable salts thereof is selected from the group consisting of:

(IV-1) 4-(5-(ethyl(2-methyl-4-quinazolinyl)amino)-2-methoxyphenyl)-N-hydroxybutanamide

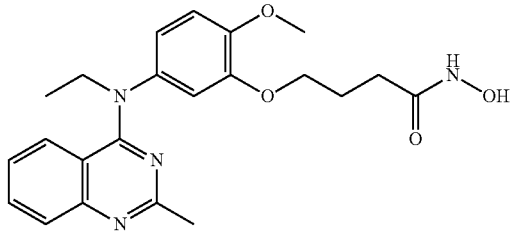 [SMILES: CCN(c1ccc(OC)c(OCCCC(=O)NO)c1)c1nc(C)nc2ccccc12]

(IV-2) N-hydroxy-4-(2-methoxy-5-((2-methyl-4-quinazolinyl)(propyl)amino)phenoxy)butanamide

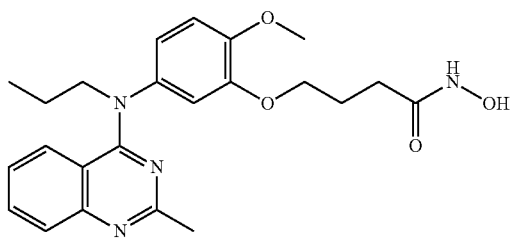

(IV-3) 4-(5-(butyl(2-methyl-4-quinazolinyl)amino)-2-methoxyphenyl)-N-hydroxybutanamide

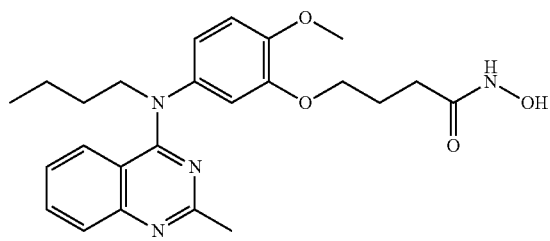 [SMILES: CCCCN(c1ccc(OC)c(OCCCC(=O)NO)c1)c1nc(C)nc2ccccc12]

(IV-4) N-hydroxy-4-(2-methoxy-5-((2-methyl-4-quinazolinyl)(pentyl)amino)phenoxy)butanamide

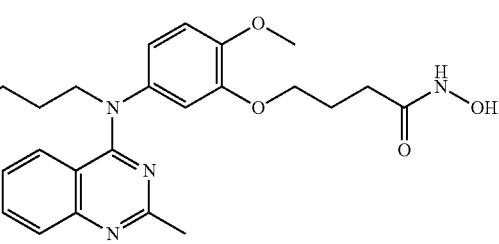

(IV-5) N-hydroxy-4-(2-methoxy-5-((methoxymethyl)(2-methyl-4-quinazolinyl)amino)phenoxy)butanamide

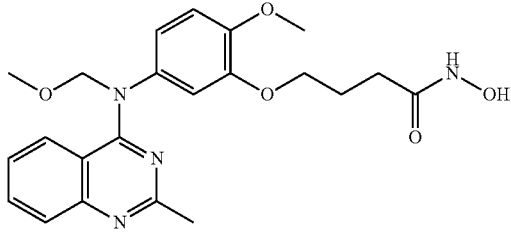

(IV-6) N-hydroxy-4-(2-methoxy-5-(((methoxymethoxy)methyl)(2-methyl-4-quinazolinyl)amino)phenoxy)butanamide

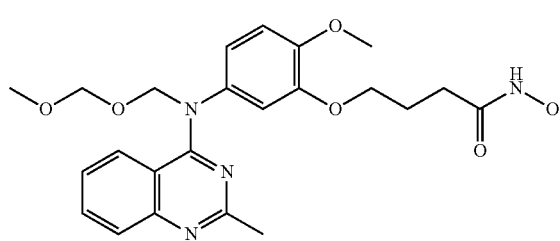

The present invention provides a preparation method of the above-mentioned compound of Formula (I) or pharmaceutically acceptable salts thereof, wherein the preparation method comprises the following steps:

(1) Adding a compound as shown in Formula (1-1) into $POCl_3$ or $SOCl_2$ followed by adding DMF, allowing for reaction to give a compound as shown in Formula (1-2):

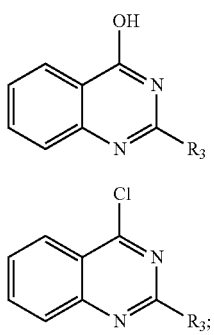

(2) In the present of $(Me)_2CHOH$, reacting the compound as shown in Formula (1-2) with a compound as shown in Formula (1-3) to give a compound as shown in Formula (1-4):

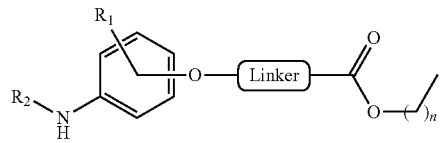

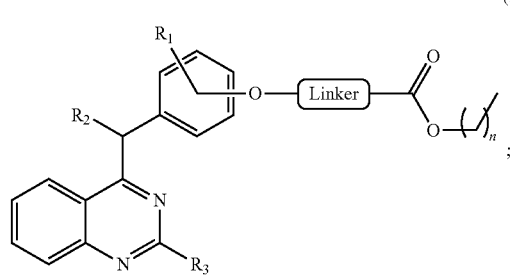

(3) Adding the compound as shown in Formula (1-4) into MeOH followed by adding $NH_2OH$ and KOH, allowing for reaction to give the compound as shown in Formula (I);

wherein, $R_1$, $R_2$, $R_3$, Linker and n are as defined above.

According the embodiments of the present invention, the synthesis route of general formula (I) is as follows:

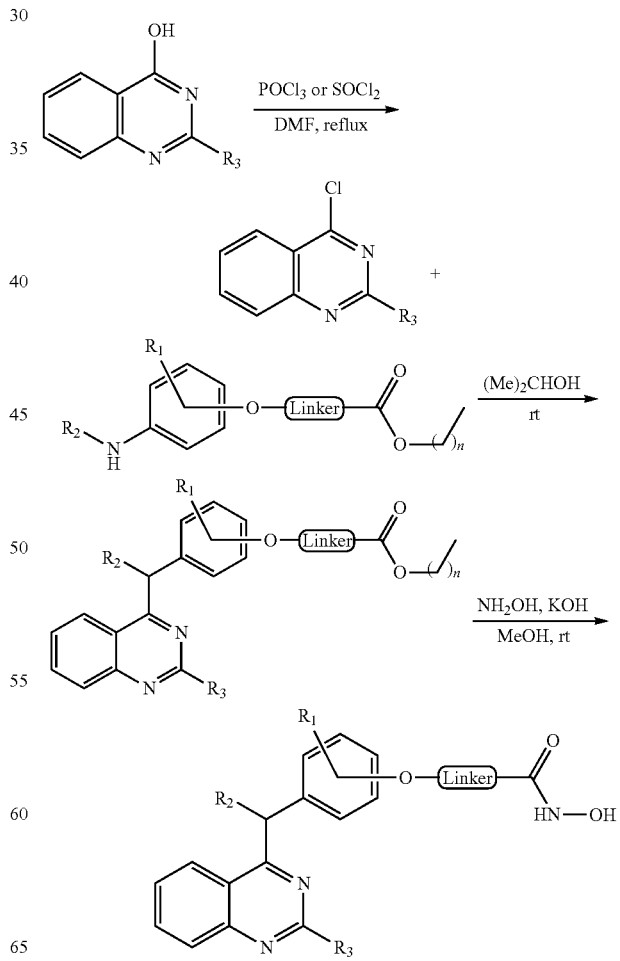

The present invention provides a preparation method of the above-mentioned compound as shown in Formula (II), wherein the preparation method comprises the following steps:

(1) Adding a compound as shown in Formula (2-1) into MOMCl followed by adding DIPEA, allowing for reaction to give a compound as shown in Formula (2-2):

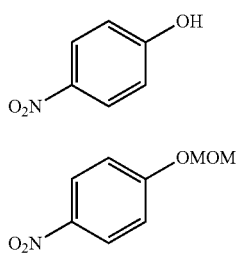

(2) Adding the compound as shown in Formula (2-2) into MeOH followed by adding Pd/C and H$_2$, allowing for reaction to give a compound as shown in Formula (2-3):

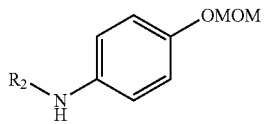

(3) Adding a compound as shown in Formula (2-4) into DMF followed by adding POCl$_3$ or SOCl$_2$, allowing for reaction to give a compound as shown in Formula (2-5):

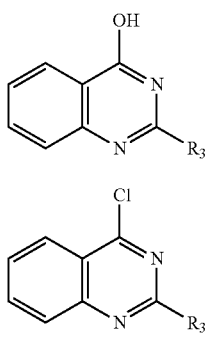

(4) In the present of (Me)$_2$CHOH, reacting the compound as shown in Formula (2-3) with the compound as shown in Formula (2-5) to give a compound as shown in Formula (2-6):

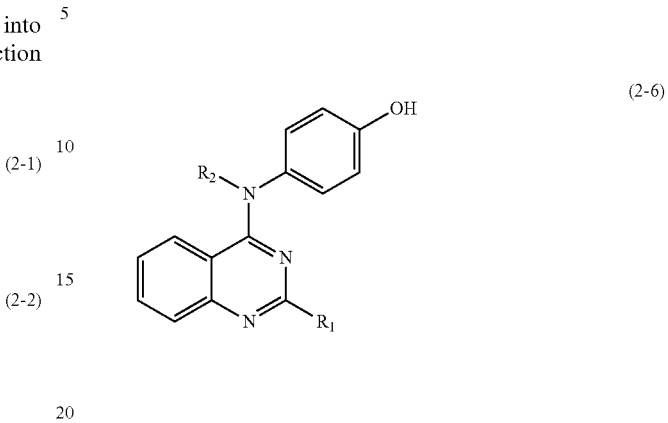

(5) Reacting the compound as shown in Formula (2-6) with a compound as shown in Formula (2-7) to give a compound as shown in Formula (2-8):

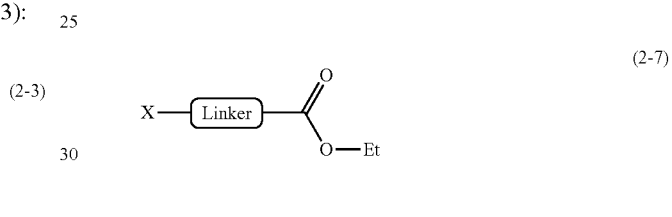

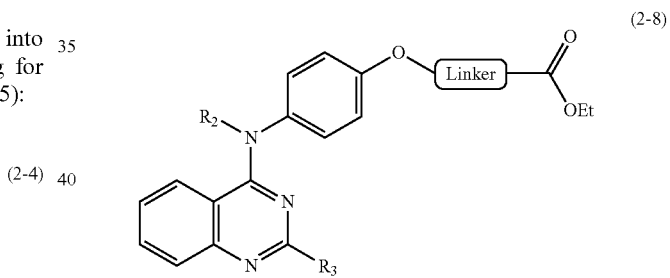

(6) Adding the compound as shown in Formula (2-8) into MeOH followed by adding NH$_2$OH and KOH, allowing for reaction to give the compound as shown in Formula (II); wherein, X is halogen F, Cl, Br, I; R$_1$, R$_2$, R$_3$ and Linker are as defined above.

According the embodiments of the present invention, the synthesis route of general formula (II) is as follows:

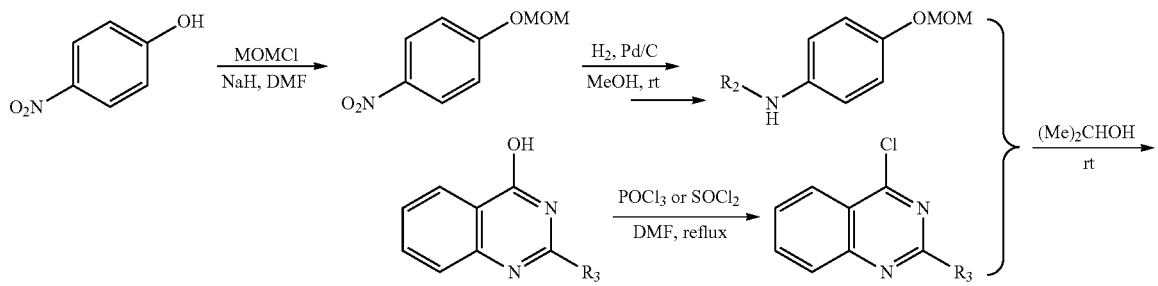

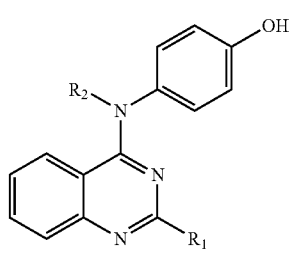 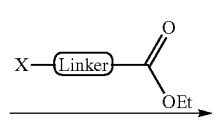 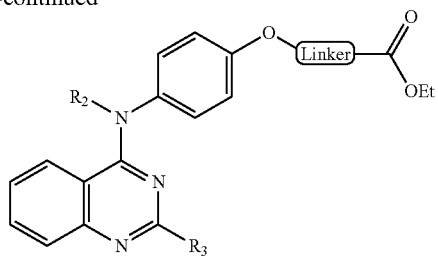 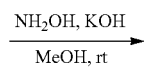

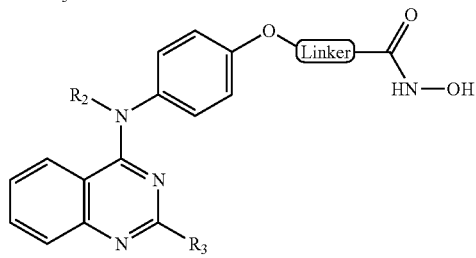

The present invention provides a preparation method of the above-mentioned compound as shown in Formula (III) or pharmaceutically acceptable salts thereof, wherein the preparation method comprises the following steps:

(1) Adding a compound as shown in Formula (3-1) into MOMCl, adding NaH, allowing for reaction to give a compound as shown in Formula (3-2):

(3-1)

![structure of 3-1: O2N-phenyl-R1, OH]

(3-2)

![structure of 3-2: O2N-phenyl-R1, OMOM]

(2) Adding the compound as shown in Formula (3-2) into MeOH followed by adding Pd/C and H$_2$, allowing for reaction to give a compound as shown in Formula (3-3):

(3-3)

![structure of 3-3: R2-NH-phenyl-R1, OMOM]

(3) Adding a compound as shown in Formula (3-4) into DMF followed by adding POCl$_3$ or SOCl$_2$, allowing for reaction to give a compound as shown in Formula (3-5):

(3-4)

![structure of 3-4: quinazoline with OH and R3]

-continued (3-5)

![structure of 3-5: quinazoline with Cl and R3]

(4) In the present of (Me)$_2$CHOH, reacting the compound as shown in Formula (3-3) with the compound as shown in Formula (3-5) to give a compound as shown in Formula (3-6):

(3-6)

![structure of 3-6]

(5) Reacting the compound as shown in Formula (3-6) with a compound as shown in Formula (3-7) to give a compound as shown in Formula (3-8):

(3-7)

![structure of 3-7: X-Linker-C(O)-O-Et]

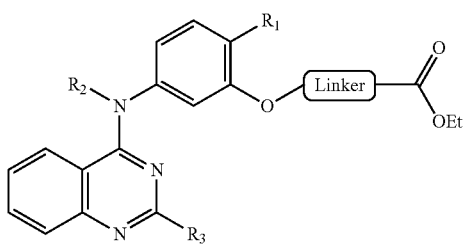

(6) Adding the compound as shown in Formula (3-8) into MeOH followed by adding $NH_2OH$ and KOH, allowing for reaction to give the compound as shown in Formula (III); wherein, X is halogen F, Cl, Br, I; $R_1$, $R_2$, $R_3$ and Linker are as defined above.

According the embodiments of the present invention, the synthesis route of general formula (III) is as follows:

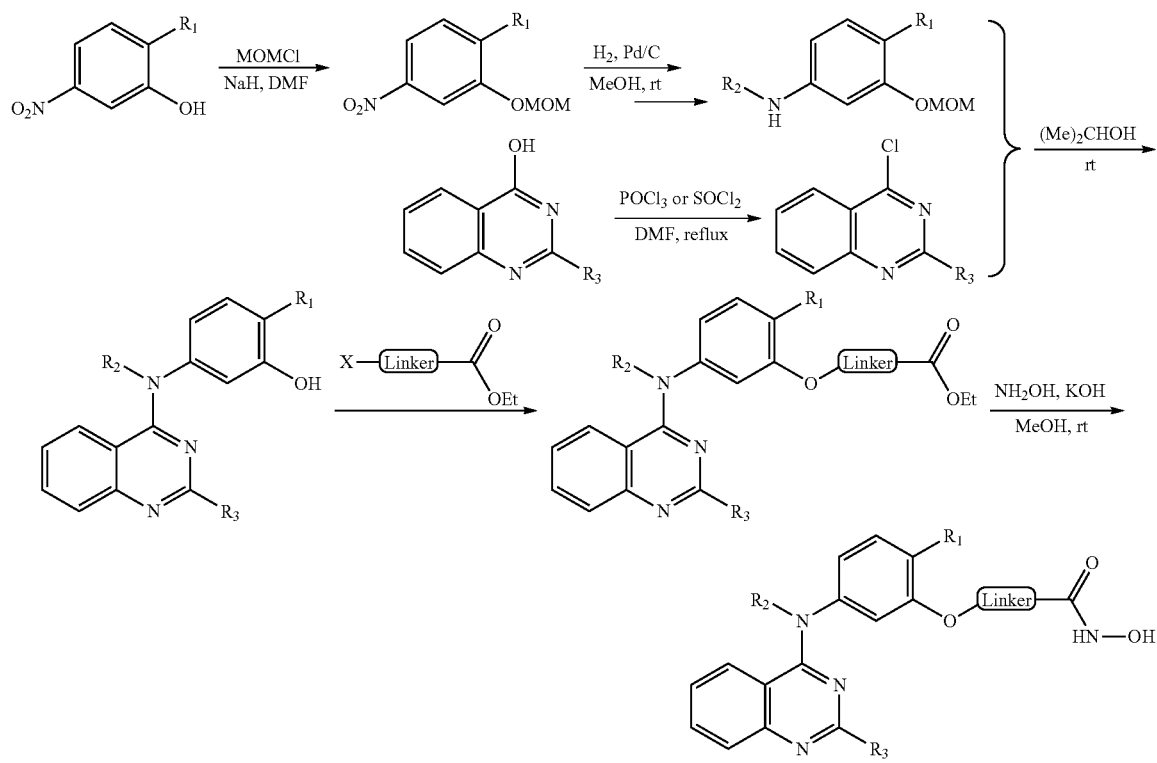

The present invention provides a preparation method of the above-mentioned compound as shown in Formula (III) or pharmaceutically acceptable salts thereof, wherein the preparation method comprises the following steps:

(1) Reacting a compound as shown in Formula (4-1) with a compound as shown in Formula (4-2) with to give a compound as shown in Formula (4-3):

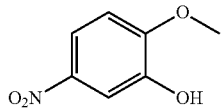

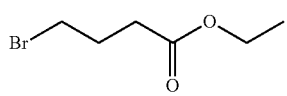

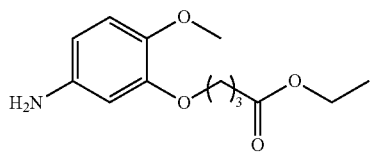

(2) Adding Pd/C and $H_2$ into the compound as shown in Formula (4-3), allowing for reaction to give a compound as shown in Formula (4-4):

(3) Adding a compound as shown in Formula (4-5) into DMF followed by adding $POCl_3$ o $SOCl_2$, allowing for reaction to give a compound as shown in Formula (4-6):

(4-5)

(4-6)

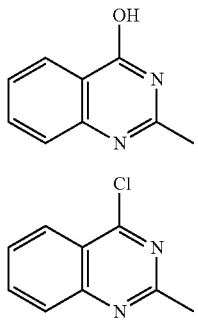

(4) In the present of $(Me)_2CHOH$, reacting the compound as shown in Formula (4-6) with the compound as shown in Formula (4-4) to give a compound as shown in Formula (4-7):

(4-7)

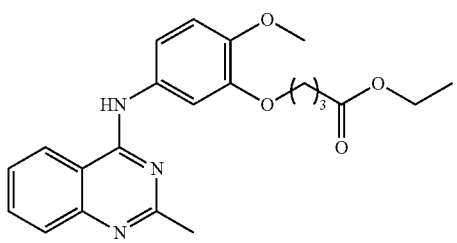

(5) Adding the compound as shown in Formula (4-7) into $R_2X$, allowing for reaction to give a compound as shown in Formula (4-8):

(4-8)

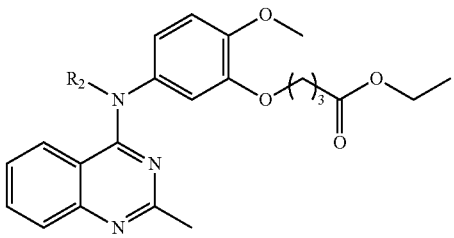

(6) Adding the compound as shown in Formula (4-8) into MeOH followed by adding $NH_2OH$ and KOH, allowing for reaction to give the compound as shown in Formula (IV), wherein, X is halogen F, Cl, Br or I; $R_2$ is as defined above.

According the embodiments of the present invention, the synthesis route of general formula (IV) is as follows:

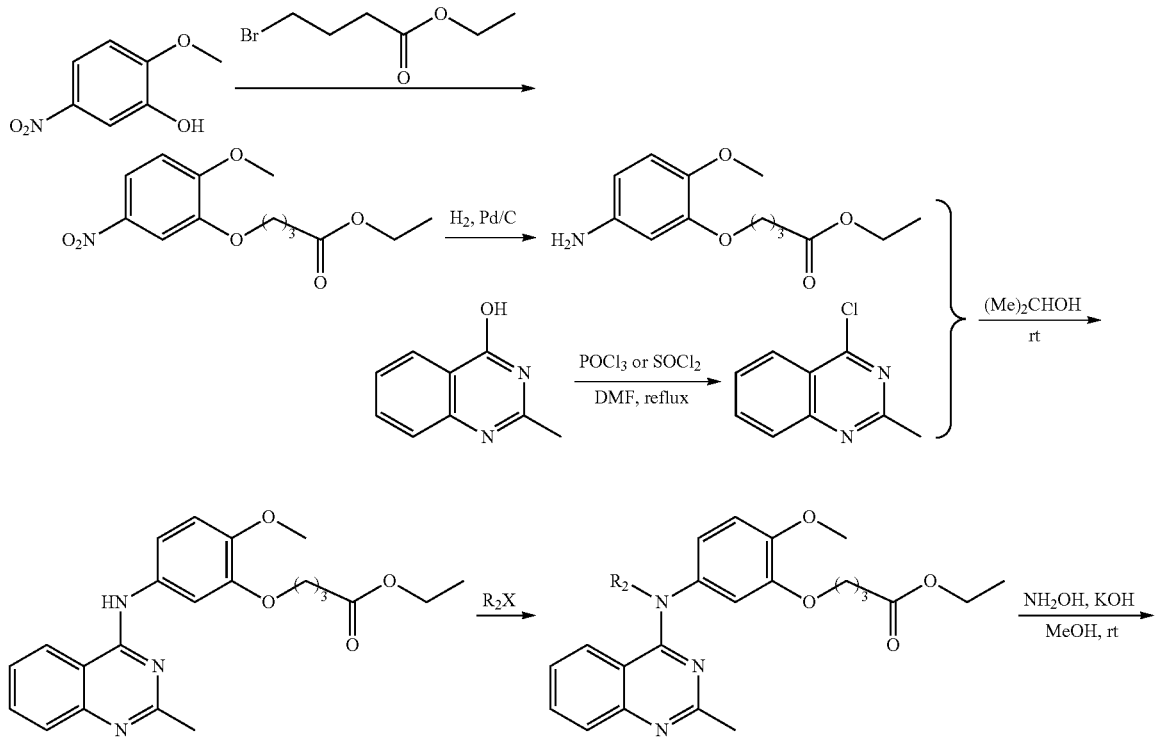

-continued

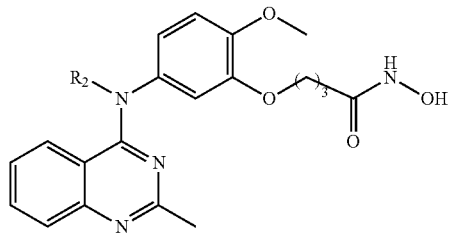

The present invention provides a use of all the above-mentioned compounds or pharmaceutically acceptable salts thereof in preparation of histone deacetylase inhibitor drugs.

The present invention provides a use of all the above-mentioned compounds or pharmaceutically acceptable salts thereof in preparation of drugs for treating tumors.

The tumor includes hematologic tumor and solid tumor; preferably, the hematologic tumor is lymphoma, multiple myeloma, leukemia; preferably, the lymphoma is B-cell lymphoma Ramos, HBL-1; preferably, the multiple myeloma is multiple myeloma MM1S; preferably, the leukemia is chronic myelomonocytic leukemia MV4-11;

preferably, the solid tumor is lung cancer, stomach cancer, colon cancer, liver cancer, breast cancer, ovarian cancer, cervical cancer, lung adenocarcinoma; preferably, the breast cancer is human breast cancer MCF-7, MDA-MB-231; preferably, the colon cancer is colon cancer HCT116; preferably, the ovarian cancer is ovarian cancer A2780s;

preferably, the tumor is lymphoma, multiple myeloma MM1S, HBL-1, human breast cancer MCF-7, MDA-MB-231, chronic myelomonocytic leukemia MV4-11, lung adenocarcinoma, colon cancer HCT116 and ovarian cancer A2780s; wherein the lymphoma is preferably B-cell lymphoma Ramos.

The present invention provides a pharmaceutical composition comprising all of the above-mentioned compounds or pharmaceutically acceptable salts thereof as well as pharmaceutically acceptable excipients.

The pharmaceutical composition is a tablet, a suppository, a dispersible tablet, an enteric-coated tablet, a chewable tablet, an orally-disintegrating tablet, a capsule, a sugar-coating formulation, a granule, a dry powder, an oral solution, a small injection, a freeze-dried powder injection or an infusion solution;

preferably, the pharmaceutically acceptable excipients include one or more selected from the following: diluent, solubilizer, disintegrant, suspending agent, lubricant, binder, filler, correctant, sweetening agent, antioxidant, surfactant, preservative, coating agent or pigment.

It is provided a method of treating a tumor, comprising administering to a patient in need a therapeutically effective amount of the compound of the invention or pharmaceutically acceptable salts thereof.

The tumor includes hematologic tumor and solid tumor; preferably, the hematologic tumor is lymphoma, multiple myeloma, leukemia; preferably, the lymphoma is B-cell lymphoma Ramos, HBL-1; preferably, the multiple myeloma is multiple myeloma MM1S; preferably, the leukemia is chronic myelomonocytic leukemia MV4-11;

preferably, the solid tumor is lung cancer, stomach cancer, colon cancer, liver cancer, breast cancer, ovarian cancer, cervical cancer, lung adenocarcinoma; preferably, the breast cancer is human breast cancer MCF-7, MDA-MB-231; preferably, the colon cancer is colon cancer HCT116; preferably, the ovarian cancer is ovarian cancer A2780s;

preferably, the tumor is lymphoma, multiple myeloma MM1S, HBL-1, human breast cancer MCF-7, MDA-MB-231, chronic myelomonocytic leukemia MV4-11, lung adenocarcinoma, colon cancer HCT116 and ovarian cancer A2780s; wherein the lymphoma is preferably B-cell lymphoma Ramos.

It is provided a method of inhibiting histone deacetylase, comprising administering to a patient in need a therapeutically effective amount of the compound according to the present invention or pharmaceutically acceptable salts thereof.

The 4-arylamino quinazoline hydroxamic acid compound according to the present invention is a compound as shown in general formula (I) or pharmaceutically acceptable salt thereof:

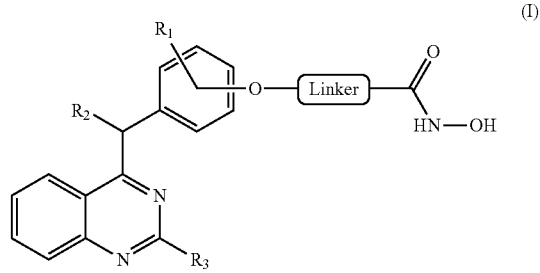

(I)

wherein, each group and substituent in general formula (I) are as defined above.

In order to facilitate understanding the present invention, the following specific compounds are preferred among the compounds of Formula (II), but the present invention is not limited to the following compounds:

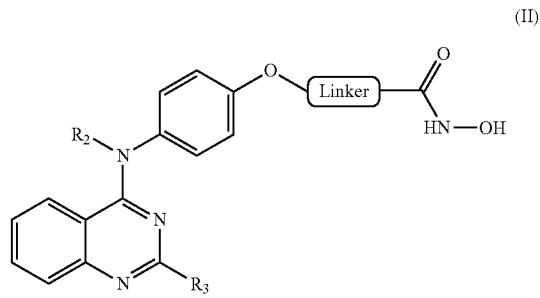

(II)

II-1    N-hydroxy-2-(4-(methyl(2-methyl-4-quinazolinyl)amino)phenoxy)acetamide;
II-2    N-hydroxy-4-(4-(methyl(2-methyl-4-quinazolinyl)amino)phenoxy)butanamide;

II-3 N-hydroxy-5-(4-(methyl(2-methyl-4-quinazolinyl)amino)phenoxy)pentanamide;
II-4 N-hydroxy-6-(4-(methyl(2-methyl-4-quinazolinyl)amino)phenoxy)hexanamide;
II-5 N-hydroxy-4-((4-(methyl(2-methyl-4-quinazolinyl)amino)phenoxy)methyl)benzamide;
II-6 N-hydroxy-4-(4-(methyl(2-methyl-4-quinazolinyl)amino)phenoxy)benzamide;
II-7 N-hydroxy-6-(4-(methyl(2-methyl-4-quinazolinyl)amino)phenoxy)nicotinamide;
II-8 N-hydroxy-5-(4-(methyl(2-methyl-4-quinazolinyl)amino)phenoxy)picolinamide;
II-9 N-hydroxy-2-(4-(methyl(2-methyl-4-quinazolinyl)amino)phenoxy)pyrimidin-5-amide;
II-10 N-hydroxy-5-(4-(methyl(2-methyl-4-quinazolinyl)amino)phenoxy)pyrimidin-2-amide;
II-11 N-hydroxy-5-(4-(methyl(2-methyl-4-quinazolinyl)amino)phenoxypyrazine-2-amide;
II-12 N-hydroxy-2-(4-(methyl(4-quinazolinyl)amino)phenoxy)acetamide;
II-13 N-hydroxy-4-(4-(methyl(4-quinazolinyl)amino)phenoxy)butanamide;
II-14 N-hydroxy-5-(4-(methyl(4-quinazolinyl)amino)phenoxy)pentanamide;
II-15 N-hydroxy-6-(4-(methyl(4-quinazolinyl)amino)phenoxy)hexanamide;
II-16 N-hydroxy-4-((4-(methyl(4-quinazolinyl)amino)phenoxy)methyl)benzamide;
II-17 N-hydroxy-4-(4-(methyl(4-quinazolinyl)amino)phenoxy)benzamide;
II-18 N-hydroxy-6-(4-(methyl(4-quinazolinyl)amino)phenoxy)nicotinamide;
II-19 N-hydroxy-5-(4-(methyl(4-quinazolinyl)amino)phenoxypicolinamide;
II-20 N-hydroxy-2-(4-(methyl(4-quinazolinyl)amino)phenoxy)pyrimidin-5-formamide;
II-21 N-hydroxy-5-(4-(methyl(4-quinazolinyl)amino)phenoxy)pyrimidin-2-formamide;
II-22 N-hydroxy-5-(4-(methyl(4-quinazolinyl)amino)phenoxy)pyrazin-2-formamide;
II-23 N-hydroxy-2-(4-((2-methyl-4-quinazolinyl)amino)phenoxy)acetamide;
II-24 N-hydroxy-3-(4-((2-methyl-4-quinazolinyl)amino)phenoxy)propionamide;
II-25 N-hydroxy-4-(4-((2-methyl-4-quinazolinyl)amino)phenoxy)butanamide;
II-26 N-hydroxy-5-(4-((2-methyl-4-quinazolinyl)amino)phenoxy)pentanamide;
II-27 N-hydroxy-6-(4-((2-methyl-4-quinazolinyl)amino)phenoxy)hexanamide.

III-1 N-hydroxy-2-(2-methoxy-5-(methyl(2-methyl-4-quinazolinyl)amino)phenoxy)acetamide;
III-2 N-hydroxy-4-(2-methoxy-5-(methyl(2-methyl-4-quinazolinyl)amino)phenoxy)butanamide;
III-3 N-hydroxy-5-(2-methoxy-5-(methyl(2-methyl-4-quinazolinyl)amino)phenoxy)pentanamide;
III-4 N-hydroxy-6-(2-methoxy-5-(methyl(2-methyl-4-quinazolinyl)amino)phenoxy)hexanamide;
III-5 N-hydroxy-4-((2-methoxy-5-(methyl(2-methyl-4-quinazolinyl)amino)phenoxy)methyl)benzamide;
III-6 N-hydroxy-4-(2-methoxy-5-(methyl(2-methyl-4-quinazolinyl)amino)phenoxy)benzamide;
III-7 N-hydroxy-6-(2-methoxy-5-(methyl(2-methyl-4-quinazolinyl)amino)phenoxy)nicotinamide;
III-8 N-hydroxy-5-(2-methoxy-5-(methyl(2-methyl-4-quinazolinyl)amino)phenoxy)picolinamide;
III-9 N-hydroxy-2-(2-methoxy-5-(methyl(2-methyl-4-quinazolinyl)amino)phenoxy)pyrimidin-5-formamide;
III-10 N-hydroxy-5-(2-methoxy-5-(methyl(2-methyl-4-quinazolinyl)amino)phenoxy)pyrimidin-2-formamide;
III-11 N-hydroxy-5-(2-methoxy-5-(methyl(2-methyl-4-quinazolinyl)amino)phenoxy)pyrazin-2-formamide;
III-12 N-hydroxy-2-(3-(methyl(2-methyl-4-quinazolinyl)amino)phenoxy)acetamide;
III-13 N-hydroxy-4-(3-(methyl(2-methyl-4-quinazolinyl)amino)phenoxy)butanamide;
III-14 N-hydroxy-5-(3-(methyl(2-methyl-4-quinazolinyl)amino)phenoxy)pentanamide;
III-15 N-hydroxy-6-(3-(methyl(2-methyl-4-quinazolinyl)amino)phenoxy)hexanamide;
III-16 N-hydroxy-4-((3-(methyl(2-methyl-4-quinazolinyl)amino)phenoxy)methyl)benzamide;
III-17 N-hydroxy-4-(3-(methyl(2-methyl-4-quinazolinyl)amino)phenoxy)benzamide;
III-18 N-hydroxy-6-(3-(methyl(2-methyl-4-quinazolinyl)amino)phenoxy)nicotinamide;
III-19 N-hydroxy-5-(3-(methyl(2-methyl-4-quinazolinyl)amino)phenoxy)picolinamide;
III-20 N-hydroxy-2-(3-(methyl(2-methyl-4-quinazolinyl)amino)phenoxy)pyrimidin-5-formamide;
III-21 N-hydroxy-5-(3-(methyl(2-methyl-4-quinazolinyl)amino)phenoxy)pyrimidin-2-formamide;
III-22 N-hydroxy-5-(3-(methyl(2-methyl-4-quinazolinyl)amino)phenoxy)pyrazin-2-formamide.

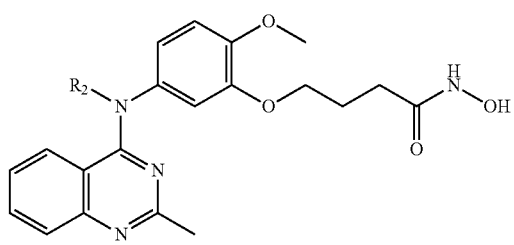

(IV)

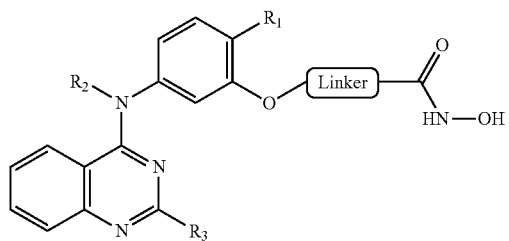

(III)

IV-1 4-(5-(ethyl(2-methyl-4-quinazolinyl)amino)-2-methoxyphenyl)-N-hydroxybutanamide;
IV-2 N-hydroxy-4-(2-methoxy-5-((2-methyl-4-quinazolinyl)(propyl)amino)phenoxy)butanamide;
IV-3 4-(5-(butyl(2-methyl-4-quinazolinyl)amino)-2-methoxyphenyl)-N-hydroxybutanamide;
IV-4 N-hydroxy-4-(2-methoxy-5-((2-methyl-4-quinazolinyl)(pentyl)amino)phenoxy)butanamide;
IV-5 N-hydroxy-4-(2-methoxy-5-((methoxymethyl)(2-methyl-4-quinazolinyl)amino)phenoxy)butanamide;

IV-6 N-hydroxy-4-(2-methoxy-5-(((methoxymethoxy)methyl)(2-methyl-4-quinazolinyl)amino)phenoxy)butanamide.

No. and corresponding structure of the preferred compounds

| No. | Structure |
|---|---|
| II-1 | |
| II-2 | |
| II-3 | |
| II-4 | |
| II-5 | |
| II-6 | 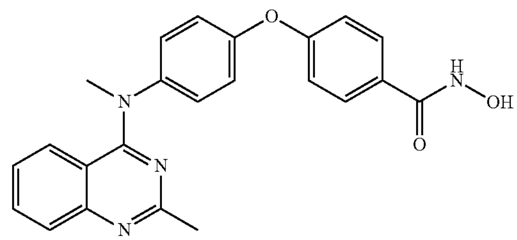 [SMILES: Cc1nc(N(C)c2ccc(Oc3ccc(C(=O)NO)cc3)cc2)c2ccccc2n1] |
| II-7 | 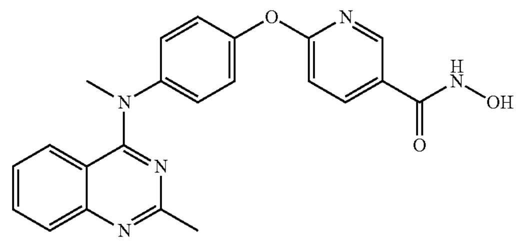 |
| II-8 | 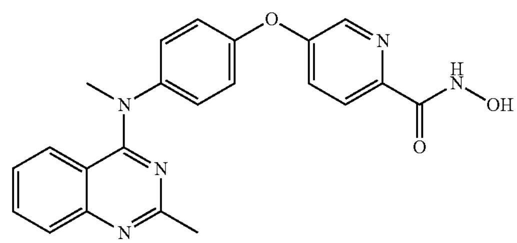 [SMILES: Cc1nc(N(C)c2ccc(Oc3ccc(C(=O)NO)nc3)cc2)c2ccccc2n1] |
| II-9 | 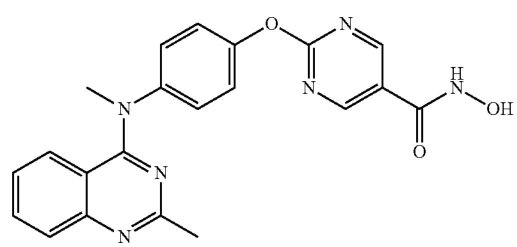 [SMILES: Cc1nc(N(C)c2ccc(Oc3ncc(C(=O)NO)cn3)cc2)c2ccccc2n1] |
| II-10 | 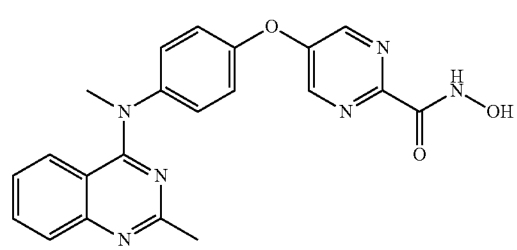 [SMILES: Cc1nc(N(C)c2ccc(Oc3cnc(C(=O)NO)nc3)cc2)c2ccccc2n1] |
| II-11 | 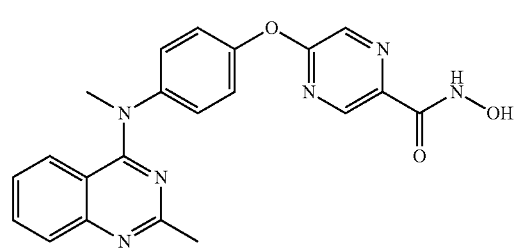 [SMILES: Cc1nc(N(C)c2ccc(Oc3cnc(C(=O)NO)cn3)cc2)c2ccccc2n1] |

| No. and corresponding structure of the preferred compounds | |
|---|---|
| No. | Structure |
| II-12 | |
| II-13 | |
| II-14 | |
| II-15 | |
| II-16 | |
| II-17 | |// -continued

| No. and corresponding structure of the preferred compounds | |
|---|---|
| No. | Structure |
| II-18 | |
| II-19 | |
| II-20 | |
| II-21 | |
| II-22 | |
| II-23 | |

| No. | Structure |
|---|---|
| II-24 | 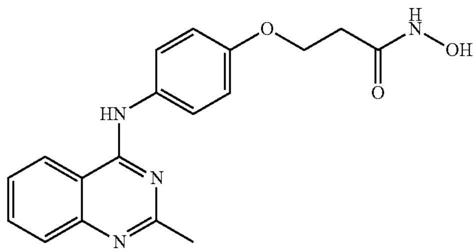 [SMILES: Cc1nc(Nc2ccc(OCCC(=O)NO)cc2)c2ccccc2n1] |
| II-25 | 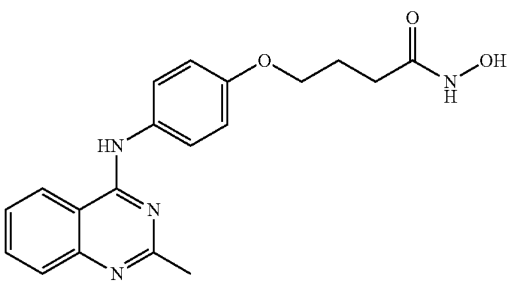 [SMILES: Cc1nc(Nc2ccc(OCCCC(=O)NO)cc2)c2ccccc2n1] |
| II-26 | 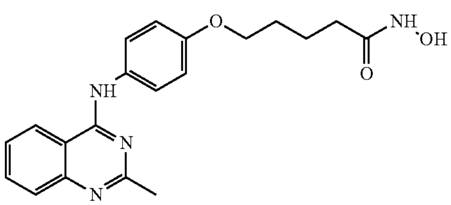 [SMILES: Cc1nc(Nc2ccc(OCCCCC(=O)NO)cc2)c2ccccc2n1] |
| II-27 | 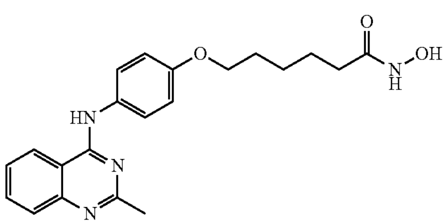 [SMILES: Cc1nc(Nc2ccc(OCCCCCC(=O)NO)cc2)c2ccccc2n1] |
| III-1 | 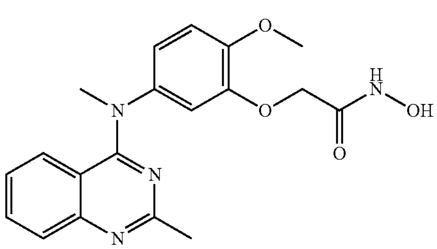 [SMILES: COc1ccc(N(C)c2nc(C)nc3ccccc23)cc1OCC(=O)NO] |
| III-2 | 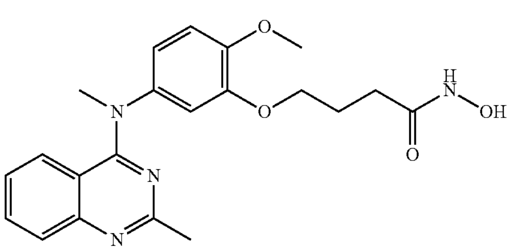 [SMILES: COc1ccc(N(C)c2nc(C)nc3ccccc23)cc1OCCCC(=O)NO] |

| No. | Structure |
|---|---|
| III-3 | 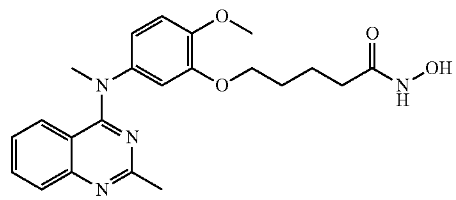 [SMILES: COc1ccc(N(C)c2nc(C)nc3ccccc23)cc1OCCCCC(=O)NO] |
| III-4 | 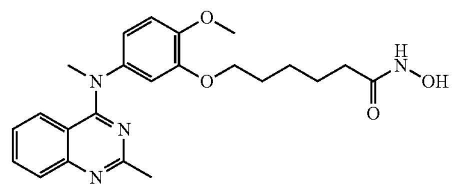 [SMILES: COc1ccc(N(C)c2nc(C)nc3ccccc23)cc1OCCCCCC(=O)NO] |
| III-5 | 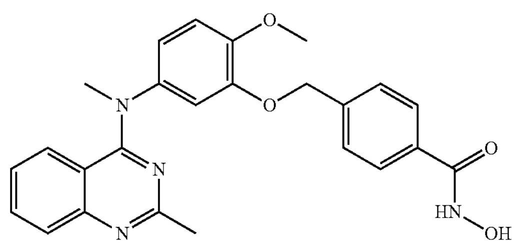 [SMILES: COc1ccc(N(C)c2nc(C)nc3ccccc23)cc1OCc1ccc(C(=O)NO)cc1] |
| III-6 | 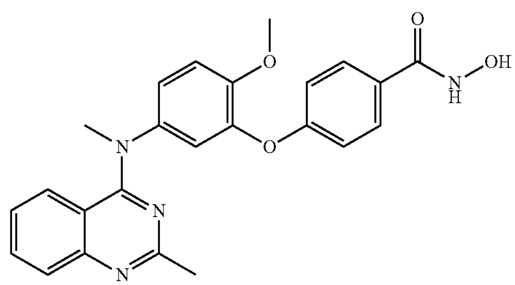 [SMILES: COc1ccc(N(C)c2nc(C)nc3ccccc23)cc1Oc1ccc(C(=O)NO)cc1] |
| III-7 | 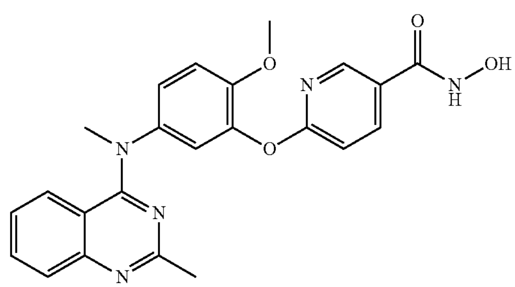 [SMILES: COc1ccc(N(C)c2nc(C)nc3ccccc23)cc1Oc1ccc(C(=O)NO)cn1] |
| III-8 | 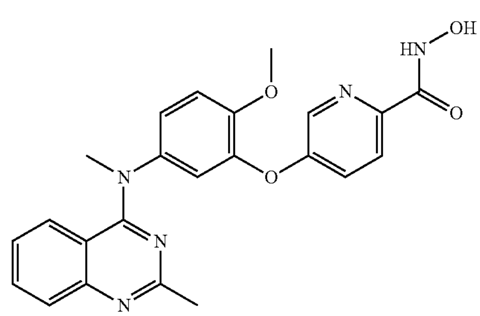 [SMILES: COc1ccc(N(C)c2nc(C)nc3ccccc23)cc1Oc1ccc(C(=O)NO)nc1] |

-continued
No. and corresponding structure of the preferred compounds
| No. | Structure |
|---|---|
| III-9 | 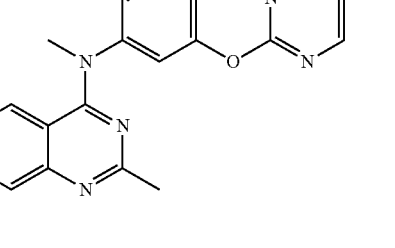 |
| III-10 | 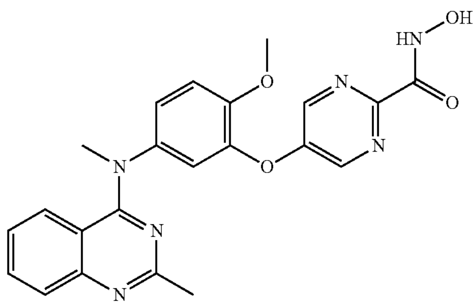 |
| III-11 | 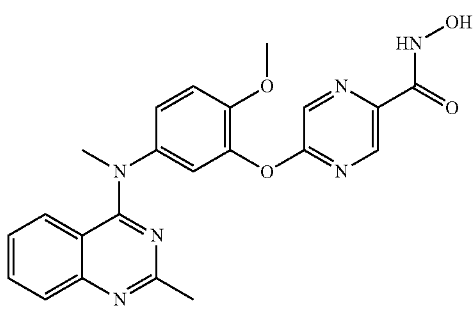 |
| III-12 | 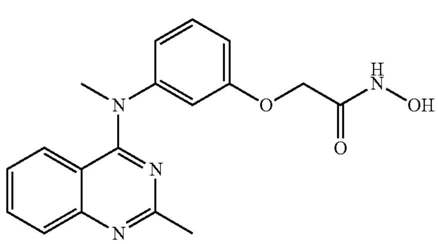 [SMILES: Cc1nc(N(C)c2cccc(OCC(=O)NO)c2)c2ccccc2n1] |
| III-13 | 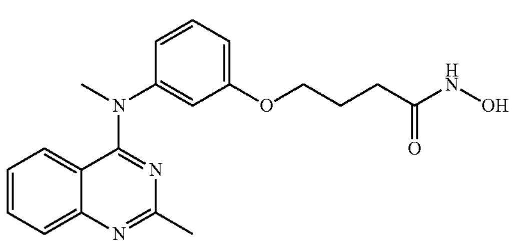 [SMILES: Cc1nc(N(C)c2cccc(OCCCC(=O)NO)c2)c2ccccc2n1] |
-continued
No. and corresponding structure of the preferred compounds
| No. | Structure |
|---|---|
| III-14 | 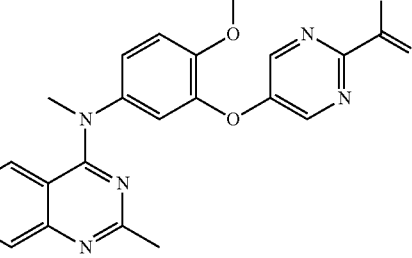 |
| III-15 | 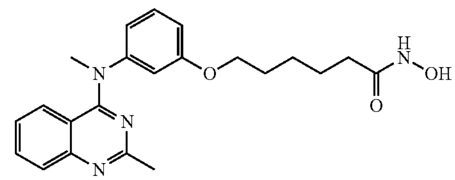 [SMILES: Cc1nc(N(C)c2cccc(OCCCCCC(=O)NO)c2)c2ccccc2n1] |
| III-16 | 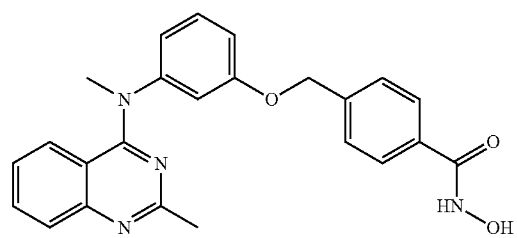 [SMILES: Cc1nc(N(C)c2cccc(OCc3ccc(C(=O)NO)cc3)c2)c2ccccc2n1] |
| III-17 | 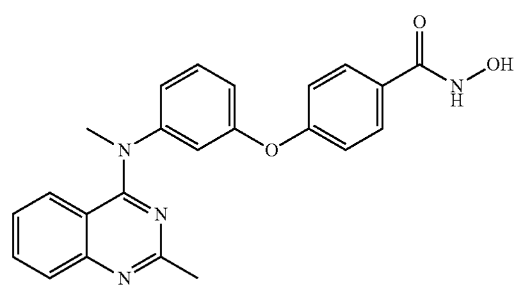 [SMILES: Cc1nc(N(C)c2cccc(Oc3ccc(C(=O)NO)cc3)c2)c2ccccc2n1] |
| III-18 | 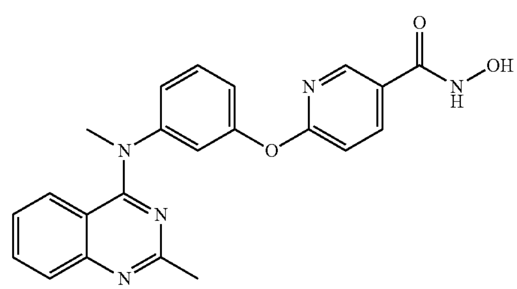 [SMILES: Cc1nc(N(C)c2cccc(Oc3ccc(C(=O)NO)cn3)c2)c2ccccc2n1] |
| III-19 | 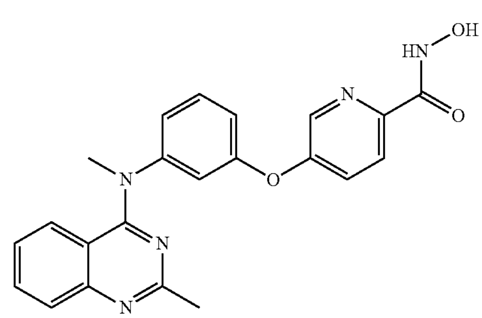 [SMILES: Cc1nc(N(C)c2cccc(Oc3ccc(C(=O)NO)nc3)c2)c2ccccc2n1] |

-continued

No. and corresponding structure of the preferred compounds

| No. | Structure |
|---|---|
| III-20 | |
| III-21 | |
| III-22 | |
| IV-1 | |
| IV-2 | 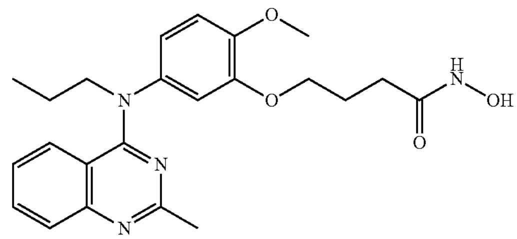 |
| IV-3 | 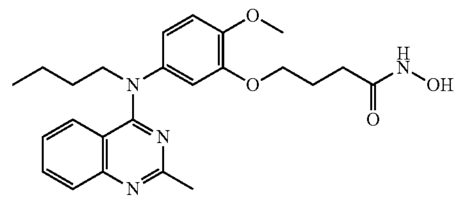 [SMILES: CCCCN(c1ccc(OC)c(OCCCC(=O)NO)c1)c1nc(C)nc2ccccc12] |
| IV-4 | 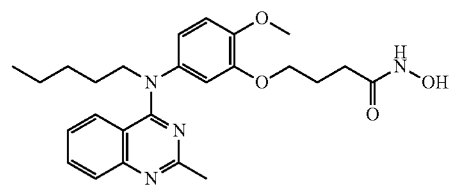 [SMILES: CCCCCN(c1ccc(OC)c(OCCCC(=O)NO)c1)c1nc(C)nc2ccccc12] |
| IV-5 | 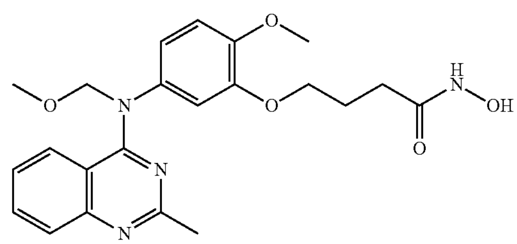 [SMILES: COCN(c1ccc(OC)c(OCCCC(=O)NO)c1)c1nc(C)nc2ccccc12] |
| IV-6 | 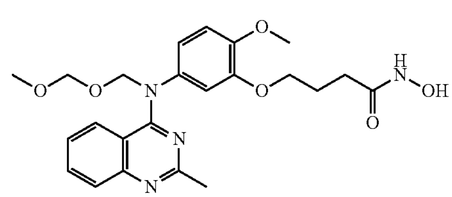 |

The compound can salt-form with inorganic acid or organic acid to give a salt-form compound, wherein the salt is hydrochloride, hydrobromide, sulfate, acetate, lactate, tartrate, tannate, citrate, trifluoroacetate, malate, maleate, succinate, p-toluenesulfonate or methanesulfonate, and the like.

The present invention provides a preparation method of analogs of Formulas I, II, III, IV via the following routes:

Route I: Synthesis route of general formula (I):

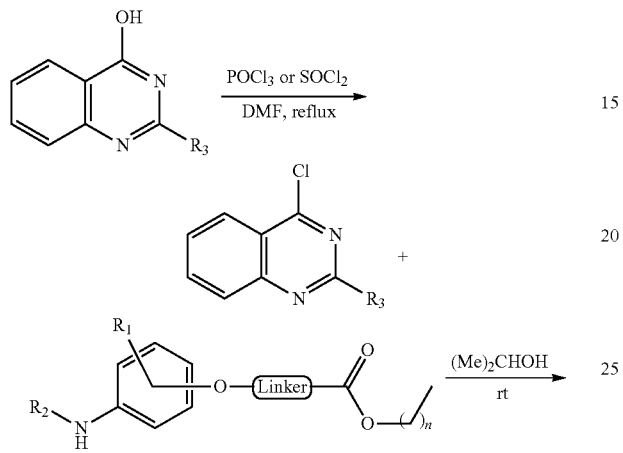

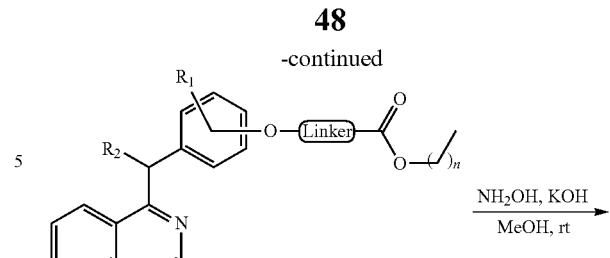

Route II: Synthesis route of general formula (II):

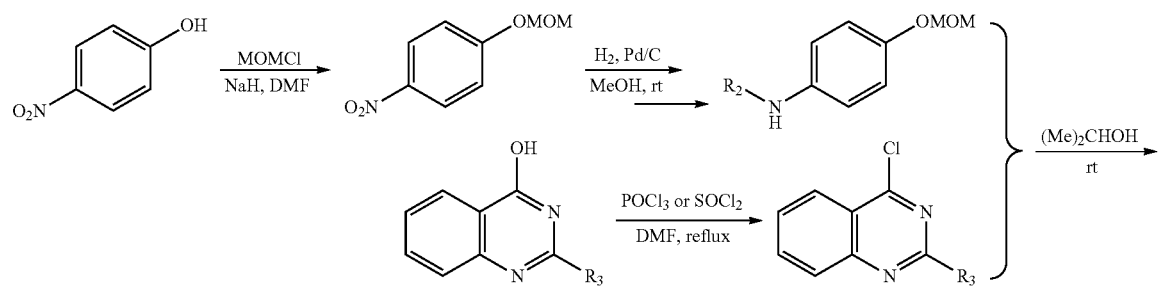

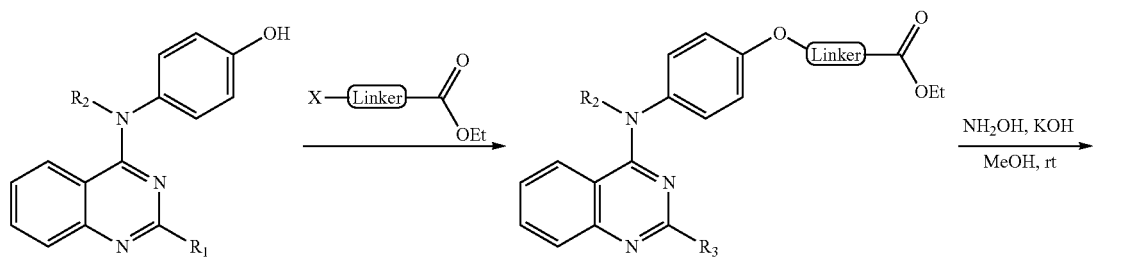

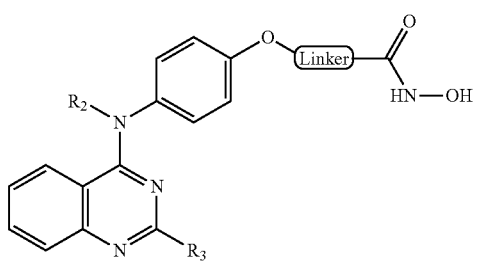

Route III: Synthesis route of general formula (III):
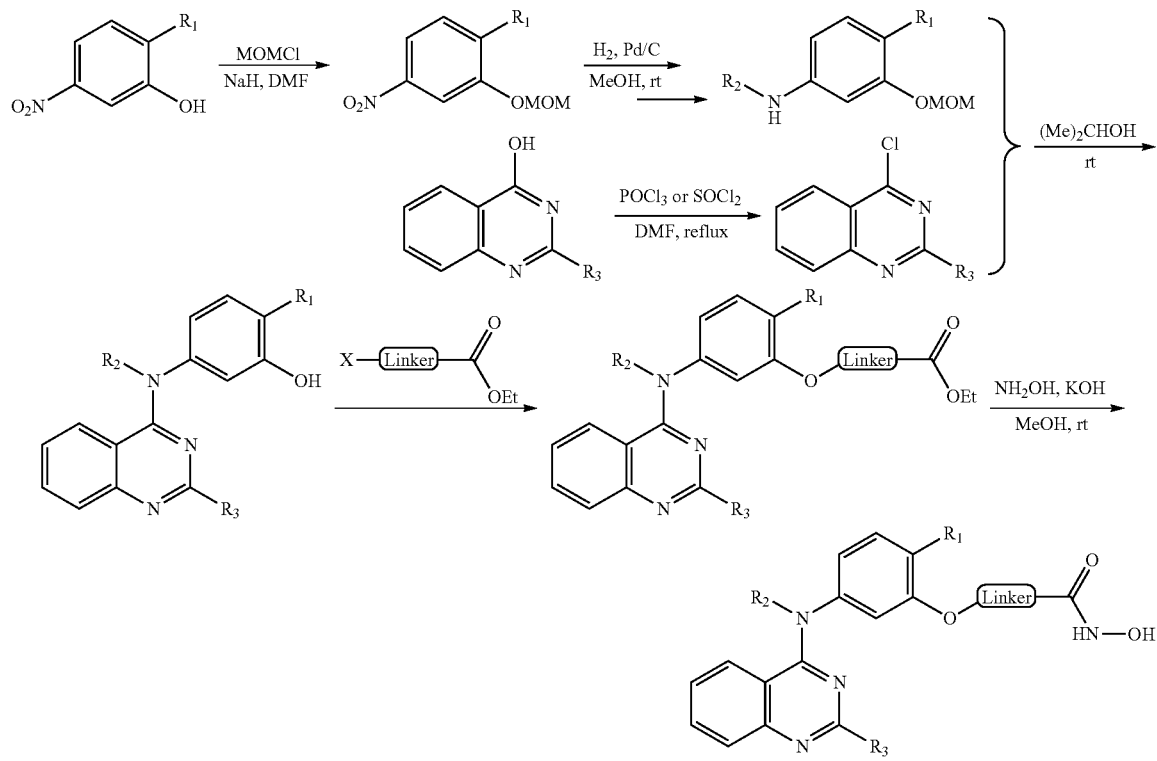
Route IV: Synthesis route of general formula (IV):
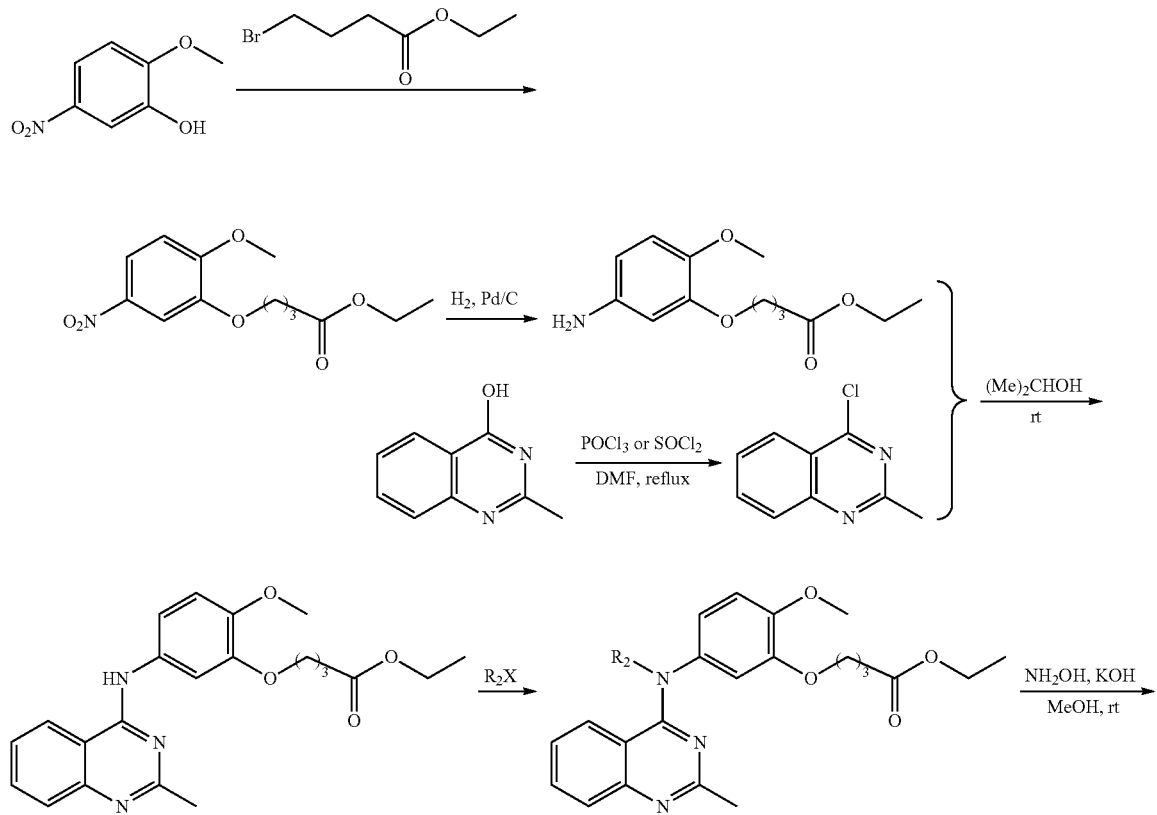

-continued

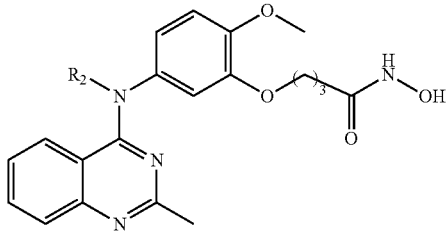

In summary, the present invention provides a novel 4-arylamino quinazoline hydroxamic acid compound having histone deacetylase inhibitory activity. It has been shown by experiments that, compared with the existing histone deacetylase inhibitors, the present invention obtains a series of selective histone deacetylase inhibitors by means of drug design and synthesis based on optimization of 4-arylamino quinazoline as enzyme surface recognition region and linking region, which have isoform selectivity and good pharmacokinetic characteristics.

DESCRIPTION OF THE DRAWINGS

Hereinafter, embodiments of the present invention will be described in details with reference to the drawings.

SPECIFIC EMODIMENTS

Figure 1:
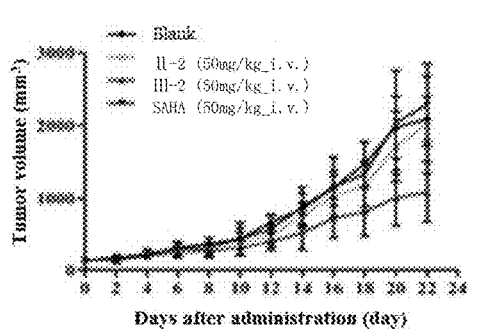
FIG. 1 depicts the therapeutic effect of the compound (II-2) and the compound (III-2) according to the present invention on the MV4-11 model.
Figure 1:
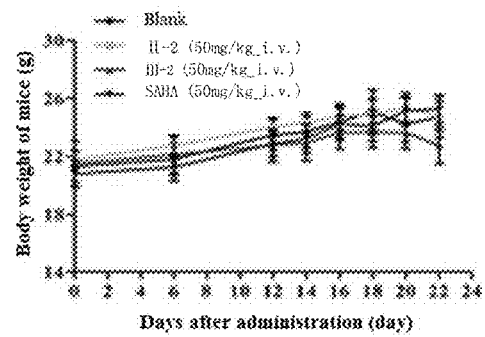
Figure 1:
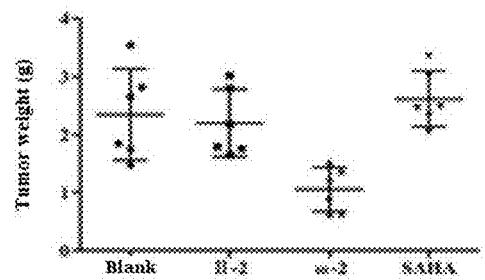
Figure 1:
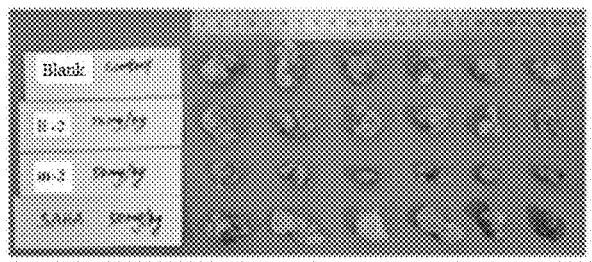

The present invention will be described in further details with reference to specific embodiments hereinafter, and the examples are given by way of illustration only but not intended to limit the scope of the present invention.

The experimental methods employed in the following examples are conventional methods, unless otherwise specified. The medicinal raw materials, reagent materials and etc. used in the following examples are all commercially available from conventional biochemical reagent stores or pharmaceutical companies, unless otherwise specified.

Example 1

Synthesis of the Compound
1-(methoxymethoxy)-4-nitrobenzene (F1)

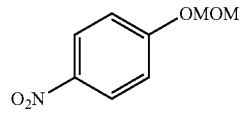

100 mmol p-nitrophenol was added into 300 ml dichloromethane while stirring in an ice-water bath. Then, 120 mmol DIPEA and 200 mmol MOMCl were successively added dropwise, followed by stirring at room temperature. After 3 hours of reaction, the reaction solution was washed successively with saturated brine, water, 1 N hydrochloric acid and saturated brine. The organic layer was spin-dried under reduced pressure to give a dark red oily target product.

Example 2

Synthesis of the Compound
4-(methoxymethoxy)aniline (F2)

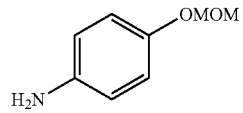

100 mmol of the compound F1 and 5 mmol 10% Pd/C were added into 250 ml methanol, followed by inletting hydrogen gas and allowing for reaction overnight at room temperature. After the reaction was complete, the reaction solution was filtered with diatomite followed by washing with ethyl acetate. The organic layers were combined and dried with $NaSO_4$ followed by spin-drying under reduced pressure to give a dark red oily target product.

Example 3

Synthesis of the Compound 4-(methoxymethoxy)-N-methylaniline (F3)

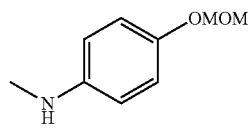

100 mmol Na was added into 200 ml methanol in batches. After the reaction was complete, 20 mmol of the compound F2 and 28 mmol paraformaldehyde were added to the reaction flask, allowed for reaction overnight at room temperature. Then 20 mmol $NaBH_4$ was added in batches, followed by heating reflux for 2 hours. The reaction solution was concentrated under reduced pressure and then 2 N NaOH solution was added into the residue, followed by extraction with tert-butyl methyl ether. The organic phases were combined, dried over anhydrous sodium sulfate and concentrated under reduced pressure to give a dark red oily target product.

Example 4

Synthesis of the Compound 2-methyl-4-chloroquinazoline (F4)

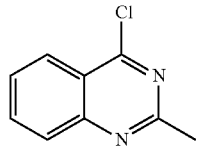

100 mmol 2-methyl-4-hydroxyquinazoline was added into 50 ml $POCl_3$, and then 3 drops of DMF was added dropwise, allowed for heating reflux. After the reaction was complete, the reaction solution was removed under reduced pressure to give an oily target product.

Example 5

Synthesis of the Compound 4-(methyl(2-methyl-4-quinazolinyl)amino)phenol (F5)

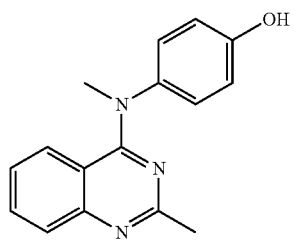 [SMILES: Cc1nc(N(C)c2ccc(O)cc2)c2ccccc2n1]

200 ml isopropanol was added into a reaction flask containing 100 mmol of the compound F4, and then 100 mmol of the compound F3 was added, while stirring at room temperature. After the reaction was complete, the reaction solution was concentrated under elevated pressure. The residue was added into ethyl acetate and concentrated hydrochloric acid while stirring, followed by TLC detection. After the reaction was complete, saturated $NaHCO_3$ solution was added to adjust the pH value to about 7. The ethyl acetate layers were collected, and the aqueous phase was extracted with ethyl acetate. The organic layers were combined and concentrated under reduced pressure to obtain a solid product, which was recrystallized from ethanol to give a light gray solid product.

1H NMR (400 MHz, DMSO-d6) δ: 9.71 (s, 1H), 7.68 (d, J=8.1 Hz, 1H), 7.63 (d, J=7.0 Hz, 1H), 7.12 (d, J=8.6 Hz, 2H), 7.08 (d, J=7.2 Hz, 1H), 7.02 (d, J=8.4 Hz, 1H), 6.85 (d, J=8.6 Hz, 2H), 3.52 (s, 3H), 2.62 (s, 3H).

Example 6

Synthesis of the Compound 2-(4-(methyl(2-methyl-4-quinazolinyl)amino)phenoxy)acetate (F6)

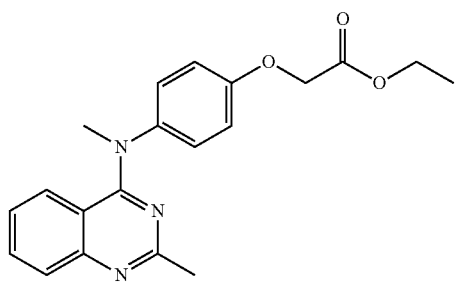 [SMILES: CCOC(=O)COc1ccc(N(C)c2nc(C)nc3ccccc23)cc1]

1 mmol of the compound F5, 2 mmol $Cs_2CO_3$, 1 ml DMF and 2 mmol ethyl bromoacetate were added into a reaction flask successively, and then heated to 80° C. and allowed for reaction for 2 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether:ethyl acetate=1:1) to give a pale yellow oily liquid target product.

Example 7

Synthesis of the Compound (II-1) N-hydroxy-2-(4-(methyl(2-methyl-4-quinazolinyl)amino)phenoxy) acetamide 0.5 mmol of the compound F6, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol to give the target product (II-1).

1H NMR (400 MHz, DMSO-d6) δ: 10.86 (s, 1H), 9.00 (s, 1H), 7.66 (d, J=8.0 Hz, 1H), 7.59 (t, J=7.4 Hz, 1H), 7.21 (d, J=8.8 Hz, 2H), 7.06 (t, J=7.2 Hz, 1H), 7.00 (d, J=8.8 Hz, 2H), 6.97 (d, J=8.6 Hz, 1H), 4.49 (s, 2H), 3.50 (s, 3H), 2.59 (s, 3H).

Example 8

Synthesis of the Compound 2-(4-(methyl(2-methyl-4-quinazolinyl)amino)phenoxy)butyrate (F7)

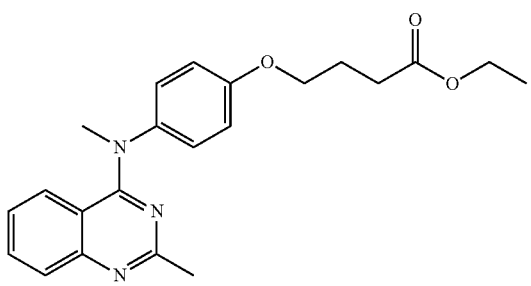 [SMILES: CCOC(=O)CCCOc1ccc(N(C)c2nc(C)nc3ccccc23)cc1]

1 mmol of the compound F5, 2 mmol Cs$_2$CO$_3$, 1 ml DMF and 2 mmol ethyl bromobutyrate were added into a reaction flask successively, and then heated to 80° C. and allowed for reaction for 2 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether:ethyl acetate=1:1) to give a pale yellow oily liquid target product.

Example 9

Synthesis of the Compound (II-2) N-hydroxy-2-(4-(methyl(2-methyl-4-quinazolinyl)amino)phenoxy)butanamide 0.5 mmol of the compound F7, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol. The target product (II-2) was then obtained.

1H NMR (400 MHz, DMSO-d6) δ: 10.43 (s, 1H), 8.75 (s, 1H), 7.65 (d, J=8.1 Hz, 1H), 7.58 (t, J=7.4 Hz, 1H), 7.18 (d, J=8.6 Hz, 2H), 7.06 (t, J=7.4 Hz, 1H), 6.97 (d, J=8.3 Hz, 3H), 3.97 (t, J=6.1 Hz, 2H), 3.49 (s, 3H), 2.59 (s, 3H), 2.14 (t, J=7.2 Hz, 2H), 1.98-1.91 (m, 2H).

Example 10

Synthesis of the Compound 2-(4-(methyl(2-methyl-4-quinazolinyl)amino)phenoxy)pentanoate (F8)

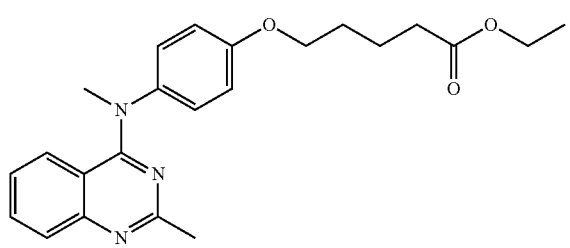 [SMILES: CCOC(=O)CCCCOc1ccc(N(C)c2nc(C)nc3ccccc23)cc1]

1 mmol of the compound F5, 2 mmol Cs$_2$CO$_3$, 1 ml DMF and 2 mmol ethyl bromovalerate were added into a reaction flask successively and then heated to 80° C. and allowed for reaction for 2 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether:ethyl acetate=1:1) to give a pale yellow oily liquid target product.

Example 11

Synthesis of the Compound (II-3) N-hydroxy-2-(4-(methyl(2-methyl-4-quinazolinyl)amino)phenoxy)pentanamide 0.5 mmol of the compound F8, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol. The target product (II-3) was then obtained.

1H NMR (400 MHz, DMSO-d6) δ: 10.38 (s, 1H), 8.70 (s, 1H), 7.65 (d, J=7.8 Hz, 1H), 7.58 (t, J=7.5 Hz, 1H), 7.18 (d, J=8.8 Hz, 2H), 7.06 (t, J=7.1 Hz, 1H), 6.97 (d, J=8.8 Hz, 3H), 3.98 (t, J=5.8 Hz, 2H), 3.49 (s, 3H), 2.59 (s, 3H), 2.03 (t, J=6.9 Hz, 2H), 1.74-1.61 (m, 4H).

Example 12

Synthesis of the Compound 2-(4-(methyl(2-methyl-4-quinazolinyl)amino)phenoxy)hexanoate (F9)

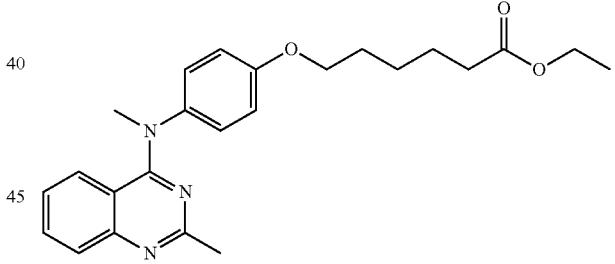

1 mmol of the compound F5, 2 mmol Cs$_2$CO$_3$, 1 ml DMF and 2 mmol ethyl bromohexanoate were added into a reaction flask successively and then heated to 80° C. and allowed for reaction for 2 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether:ethyl acetate=1:1) to give a pale yellow oily liquid target product.

Example 13

Synthesis of the Compound (II-4) N-hydroxy-2-(4-(methyl(2-methyl-4-quinazolinyl)amino)phenoxy)hexanamide 0.5 mmol of the compound F6, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol. The target product (II-4) was then obtained.

1H NMR (400 MHz, DMSO-d6) δ: 10.36 (s, 1H), 8.70 (s, 1H), 7.65 (d, J=7.6 Hz, 1H), 7.62-7.55 (m, 1H), 7.17 (d, J=8.8 Hz, 2H), 7.06 (t, J=7.1 Hz, 1H), 6.97 (d, J=8.8 Hz, 3H), 3.96 (t, J=6.4 Hz, 2H), 3.49 (s, 3H), 2.58 (s, 3H), 1.98 (t, J=7.2 Hz, 2H), 1.79-1.65 (m, 2H), 1.62-1.50 (m, 2H), 1.43-1.37 (m, 2H).

Example 14

Synthesis of the Compound 4-((4-(methyl(2-methyl-4-quinazolinyl)amino)phenoxy)methyl)ethyl benzoate (F10)

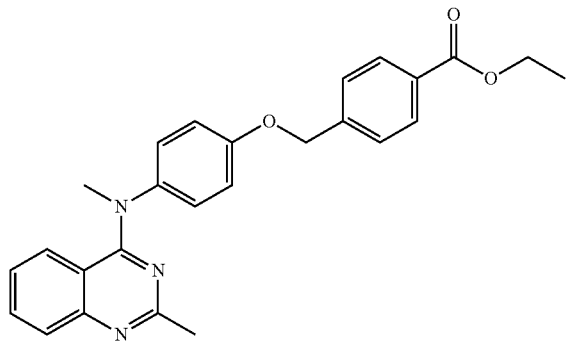 [SMILES: CCOC(=O)c1ccc(COc2ccc(N(C)c3nc(C)nc4ccccc34)cc2)cc1]

1 mmol of the compound F5, 2 mmol $Cs_2CO_3$, 1 ml DMF and 2 mmol 4-(ethyl formate) benzyl bromide were added into a reaction flask successively and then heated to 80° C. and allowed for reaction for 2 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether:ethyl acetate=1:1) to give a pale yellow oily liquid target product.

Example 15

Synthesis of the Compound (II-5) N-hydroxy-4-((4-(methyl(2-methyl-4-quinazolinyl)amino)phenoxy)methyl)benzoate 0.5 mmol of the compound F10, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol. The target product (II-5) was then obtained.

1H NMR (400 MHz, DMSO-d6) δ: 11.25 (s, 1H), 9.08 (s, 1H), 7.78 (d, J=7.9 Hz, 2H), 7.65 (d, J=8.2 Hz, 1H), 7.58 (t, J=7.4 Hz, 1H), 7.53 (d, J=7.9 Hz, 2H), 7.20 (d, J=8.6 Hz, 2H), 7.07 (d, J=8.5 Hz, 2H), 7.03 (d, J=7.2 Hz, 1H), 6.95 (d, J=8.4 Hz, 1H), 5.19 (s, 2H), 3.49 (s, 3H), 2.58 (s, 3H).

Example 16

Synthesis of the Compound methyl 4-(4-(methyl(2-methyl-4-quinazolinyl)amino)phenoxy) benzoate (F11)

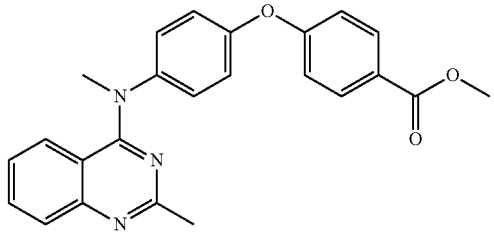 [SMILES: COC(=O)c1ccc(Oc2ccc(N(C)c3nc(C)nc4ccccc34)cc2)cc1]

1 mmol of the compound F5, N,N-dimethylglycine, cuprous iodide, $Cs_2CO_3$, 1,4-dioxane and 2 mmol methyl 4-bromobenzoate were added into a reaction flask successively, and then heated to 80° C. under nitrogen atmosphere and allowed for reaction for 24 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether:ethyl acetate=1:1) to give a pale yellow oily liquid target product.

Example 17

Synthesis of the Compound (II-6) N-hydroxy-4-(4-(methyl(2-methyl-4-quinazolinyl)amino)phenoxy) benzamide 0.5 mmol of the compound F11, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol. The target product (II-6) was then obtained.

$^1$H NMR (400 MHz, DMSO-d6) δ: 11.21 (s, 1H), 9.04 (s, 1H), 7.82 (d, J=8.6 Hz, 2H), 7.68 (d, J=8.0 Hz, 1H), 7.63 (t, J=7.3 Hz, 1H), 7.30 (d, J=8.7 Hz, 2H), 7.16 (d, J=7.9 Hz, 1H), 7.12 (d, J=8.7 Hz, 2H), 7.07 (d, J=8.6 Hz, 2H), 7.02 (d, J=8.5 Hz, 1H), 3.55 (s, 3H), 2.61 (s, 3H).

Example 18

Synthesis of the Compound methyl 6-(4-(methyl(2-methyl-4-quinazolinyl)amino)phenoxy)nicotinate (F12)

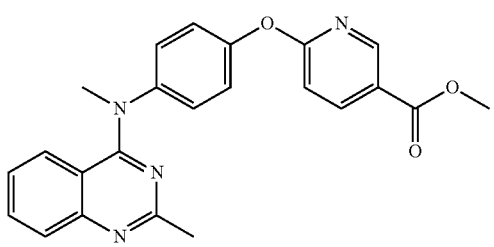 [SMILES: COC(=O)c1ccc(Oc2ccc(N(C)c3nc(C)nc4ccccc34)cc2)nc1]

1 mmol of the compound F5, N,N-dimethylglycine, cuprous iodide, Cs₂CO₃, 1,4-dioxane and 2 mmol methyl 2-chloro-4-nicotinate were added into a reaction flask successively, and then heated to 80° C. under nitrogen atmosphere and allowed for reaction for 24 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether:ethyl acetate=1:1) to give a pale yellow oily liquid target product.

1H NMR (400 MHz, DMSO-d6) δ: 8.73 (d, J=2.2 Hz, 1H), 8.34 (dd, J=8.6, 2.4 Hz, 1H), 7.69 (d, J=8.1 Hz, 1H), 7.63 (t, J=7.5 Hz, 1H), 7.32 (d, J=8.8 Hz, 2H), 7.24 (d, J=8.8 Hz, 2H), 7.17 (d, J=8.6 Hz, 1H), 7.14 (d, J=7.1 Hz, 1H), 7.04 (d, J=8.4 Hz, 1H), 3.86 (s, 3H), 3.58 (s, 3H), 2.62 (s, 3H).

Example 19

Synthesis of the Compound (II-7) N-hydroxy-6-(4-(methyl(2-methyl-4-quinazolinyl)amino)phenoxy)nicotinamide 0.5 mmol of the compound F12, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol. The target product (II-7) was then obtained.

1H NMR (400 MHz, DMSO-d6) δ: 11.28 (s, 1H), 9.14 (s, 1H), 8.53 (d, J=2.3 Hz, 1H), 8.18 (dd, J=8.6, 2.4 Hz, 1H), 7.69 (d, J=7.8 Hz, 1H), 7.63 (t, J=7.0 Hz, 1H), 7.31 (d, J=8.8 Hz, 2H), 7.21 (d, J=8.8 Hz, 2H), 7.14 (d, J=8.8 Hz, 1H), 7.13 (d, J=6.8 Hz, 1H), 7.03 (d, J=8.2 Hz, 1H), 3.58 (s, 3H), 2.61 (s, 3H).

Example 20

Synthesis of the Compound 5-(4-(methyl(2-methyl-4-quinazolinyl)amino)phenoxy)methyl nicotinate (F13)

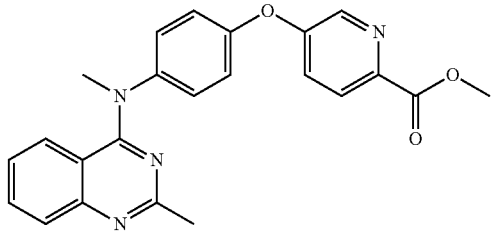 [SMILES: COC(=O)c1ccc(Oc2ccc(N(C)c3nc(C)nc4ccccc34)cc2)cn1]

1 mmol of the compound F5, N,N-dimethylglycine, cuprous iodide, Cs₂CO₃, 1,4-dioxane and 2 mmol methyl 5-chloropyridine-2-carboxylate were added into a reaction flask successively and then heated to 80° C. under nitrogen atmosphere and allowed for reaction for 24 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether: ethyl acetate=1:1) to give a pale yellow oily liquid target product.

Example 21

Synthesis of the Compound (II-8) N-hydroxy-5-(4-(methyl(2-methyl-4-quinazolinyl)amino)phenoxy) pyridine carboxamide 0.5 mmol of the compound F13, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol. The target product (II-8) was then obtained.

Example 22

Synthesis of the Compound 2-(4-(methyl(2-methyl-4-quinazolinyl)amino)phenoxy)pyrimidin-5-methyl ester (F14)

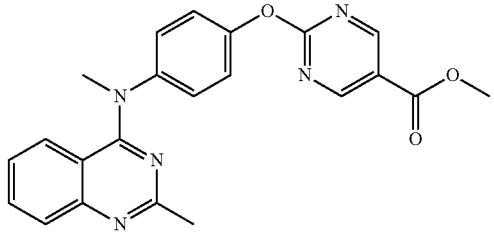 [SMILES: COC(=O)c1cnc(Oc2ccc(N(C)c3nc(C)nc4ccccc34)cc2)nc1]

1 mmol of the compound F5, N,N-dimethylglycine, cuprous iodide, Cs₂CO₃, 1,4-dioxane and 2 mmol methyl 2-chloropyrimidine-5-carboxylate were added into a reaction flask successively, and then heated to 80° C. under nitrogen atmosphere and allowed for reaction for 24 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether: ethyl acetate=1:1) to give a pale yellow oily liquid target product.

Example 23

Synthesis of the Compound (II-9) N-hydroxy-2-(4-(methyl(2-methyl-4-quinazolinyl)amino)phenoxy)pyrimidin-5-formamide 0.5 mmol of the compound F14, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol. The target product (II-9) was then obtained.

Example 24

Synthesis of the Compound methyl 5-(4-(methyl(2-methyl-4-quinazolinyl)amino)phenoxy)pyrimidin-2-formate (F15)

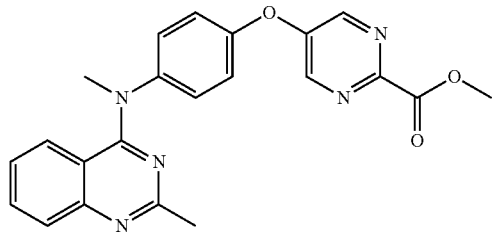 [SMILES: COC(=O)c1ncc(Oc2ccc(N(C)c3nc(C)nc4ccccc34)cc2)cn1]

1 mmol of the compound F5, N,N-dimethylglycine, cuprous iodide, $Cs_2CO_3$, 1,4-dioxane and 2 mmol methyl 5-bromo-2-pyrimidinecarboxylate were added into a reaction flask successively, and then heated to 80° C. under nitrogen atmosphere and allowed for reaction for 24 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether: ethyl acetate=1:1) to give a pale yellow oily liquid target product.

Example 25

Synthesis of the Compound (II-10) N-hydroxy-5-(4-(methyl(2-methyl-4-quinazolinyl)amino)phenoxy)pyrimidin-2-formamide 0.5 mmol of the compound F15, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol. The target product (II-10) was then obtained.

Example 26

Synthesis of the Compound methyl 5-(4-(methyl(2-methyl-4-quinazolinyl)amino)phenoxy)pyrazin-2-formate (F16)

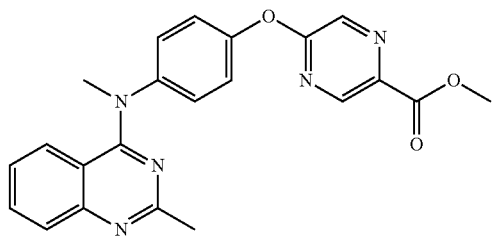 [SMILES: COC(=O)c1cnc(Oc2ccc(N(C)c3nc(C)nc4ccccc34)cc2)cn1]

1 mmol of the compound F5, N,N-dimethylglycine, cuprous iodide, $Cs_2CO_3$, 1,4-dioxane and 2 mmol methyl 5-bromopyrazin-2-carboxylate were added into a reaction flask successively, and then heated to 80° C. under nitrogen atmosphere and allowed for reaction for 24 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether: ethyl acetate=1:1) to give a pale yellow oily liquid target product.

Example 27

Synthesis of the Compound (II-11) N-hydroxy-5-(4-(methyl(2-methyl-4-quinazolinyl)amino)phenoxy-pyrazine-2-formamide 0.5 mmol of the compound F16, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol. The target product (II-11) was then obtained.

Example 28

Synthesis of the Compound 4-chloroquinazoline (F17)

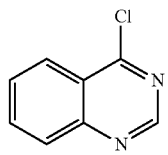

100 mmol 4-hydroxyquinazoline was added into 50 ml POCl$_3$, and then 3 drops of DMF was added dropwise, allowed for heating reflux. After the reaction was complete, the reaction solution was removed under reduced pressure to give an oily target product.

Example 29

Synthesis of the Compound 4-(methyl(4-quinazolinyl)amino)phenol (F18)

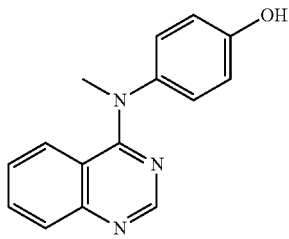 [SMILES: CN(c1ccc(O)cc1)c1ncnc2ccccc12]

200 ml isopropanol was added into a reaction flask containing 100 mmol of the compound F13, and then 100 mmol of the compound F3 was added and stirred at room temperature. After the reaction was complete, the reaction solution was concentrated under elevated pressure. Saturated NaHCO$_3$ solution was added to the concentrated residue, adjust the pH value to pH=8, the solid was precipitated, dried by suction filtration and recrystallized from ethanol to give a light grey solid product.

1H NMR (400 MHz, DMSO-d6) δ: 10.04 (s, 1H), 8.91 (d, J=1.8 Hz, 1H), 7.86 (d, J=7.9 Hz, 1H), 7.79 (t, J=7.6 Hz, 1H), 7.28 (d, J=8.4 Hz, 1H), 7.24 (d, J=7.3 Hz, 2H), 6.91 (d, J=8.3 Hz, 3H), 3.64 (s, 3H).

Example 30

Synthesis of ethyl 2-(4-(methyl(4-quinazolinyl)amino) phenoxyacetate (F19)

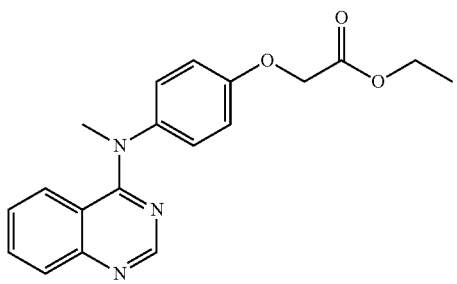 [SMILES: CCOC(=O)COc1ccc(N(C)c2ncnc3ccccc23)cc1]

1 mmol of the compound F18, 2 mmol Cs$_2$CO$_3$, 1 ml DMF and 2 mmol ethyl bromoacetate were added into a reaction flask successively, and then heated to 80° C. and allowed for reaction for 2 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether:ethyl acetate=1:1) to give a pale yellow oily liquid target product.

Example 31

Synthesis of the Compound (II-12) N-hydroxy-2-(4-(methyl(4-quinazolinyl)amino)phenoxy)acetamide 0.5 mmol of the compound F19, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol. The target product (II-12) was then obtained.

Example 32

Synthesis of ethyl 4-(4-(methyl(4-quinazolinyl)amino)phenoxy)butyl ester (F20)

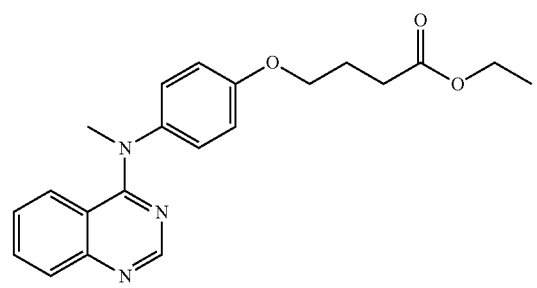 [SMILES: CCOC(=O)CCCOc1ccc(N(C)c2ncnc3ccccc23)cc1]

1 mmol of the compound F18, 2 mmol Cs$_2$CO$_3$, 1 ml DMF and 2 mmol ethyl butyrate were added into a reaction flask successively, and then heated to 80° C. and allowed for reaction for 2 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether:ethyl acetate=1:1) to give a pale yellow oily liquid target product.

1H NMR (400 MHz, CDCl3) δ: 8.80 (s, 1H), 7.84 (d, J=8.4 Hz, 1H), 7.60-7.56 (m, 1H), 7.15-7.08 (m, 2H), 7.05 (d, J=3.6 Hz, 2H), 6.94-6.87 (m, 2H), 4.16 (q, J=7.2 Hz, 2H), 4.03 (t, J=6.1 Hz, 2H), 3.60 (s, 3H), 2.54 (t, J=7.2 Hz, 2H), 2.14 (p, J=6.8 Hz, 2H), 1.27 (t, J=7.2 Hz, 3H).

Example 33

Synthesis of the Compound (II-13) N-hydroxy-4-(4-(methyl(4-quinazolinyl)amino)phenoxy)butanamide 0.5 mmol of the compound F20, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol. The target product (II-13) was then obtained.

1H NMR (400 MHz, DMSO-d6) δ: 10.43 (s, 1H), 8.71 (s, 2H), 7.74 (d, J=7.9 Hz, 1H), 7.67-7.61 (m, 1H), 7.20 (d, J=8.8 Hz, 2H), 7.18-7.11 (m, 1H), 7.01 (d, J=8.9 Hz, 1H), 6.98 (d, J=8.8 Hz, 2H), 3.98 (t, J=6.3 Hz, 2H), 3.51 (s, 3H), 2.14 (t, J=7.4 Hz, 2H), 1.96 (dd, J=13.9, 6.6 Hz, 2H).

Example 34

Synthesis of the Compound 2-(4-(methyl(4-quinazolinyl)amino)phenoxy)pentanoate (F21)

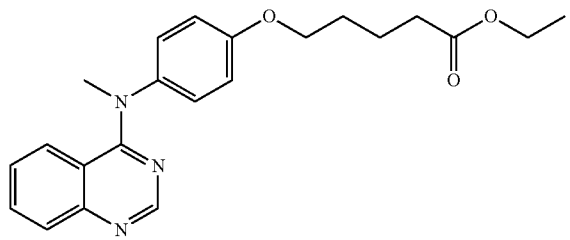 [SMILES: CCOC(=O)CCCCOc1ccc(N(C)c2ncnc3ccccc23)cc1]

1 mmol of the compound F18, 2 mmol Cs₂CO₃, 1 ml DMF and 2 mmol ethyl bromovalerate were added into a reaction flask successively, and then heated to 80° C. and allowed for reaction for 2 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether:ethyl acetate=1:1) to give a pale yellow oily liquid target product.

1H NMR (400 MHz, CDCl3) δ: 8.80 (s, 1H), 7.85 (d, J=8.3 Hz, 1H), 7.62-7.54 (m, 1H), 7.11 (d, J=8.8 Hz, 2H), 7.05 (d, J=3.9 Hz, 2H), 6.90 (d, J=8.8 Hz, 2H), 4.14 (q, J=7.1 Hz, 2H), 4.00 (t, J=5.6 Hz, 2H), 3.60 (s, 3H), 2.40 (t, J=6.9 Hz, 2H), 1.90-1.80 (m, 4H), 1.27 (t, J=7.1 Hz, 3H).

Example 35

Synthesis of the Compound (II-14) N-hydroxy-2-(4-(methyl(4-quinazolinyl)amino)phenoxy)pentanamide 0.5 mmol of the compound F21, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol. The target product (II-14) was then obtained.

1H NMR (400 MHz, DMSO-d6) δ: 10.38 (s, 1H), 8.71 (s, 2H), 7.74 (d, J=8.1 Hz, 1H), 7.68-7.60 (m, 1H), 7.20 (d, J=8.8 Hz, 2H), 7.17-7.11 (m, 1H), 7.02 (d, J=9.0 Hz, 1H), 6.98 (d, J=8.8 Hz, 2H), 3.98 (t, J=5.9 Hz, 2H), 3.50 (s, 3H), 2.03 (t, J=6.9 Hz, 2H), 1.77-1.58 (m, 4H).

Example 36

Synthesis of the Compound 2-(4-(methyl(4-quinazolinyl)amino)phenoxy)hexanoate (F22)

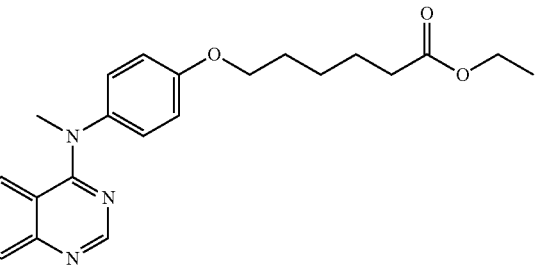

1 mmol of the compound F18, 2 mmol Cs₂CO₃, 1 ml DMF and 2 mmol ethyl bromohexanoate were added into a reaction flask successively, and then heated to 80° C. and allowed for reaction for 2 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether:ethyl acetate=1:1) to give a pale yellow oily liquid target product.

1H NMR (400 MHz, CDCl3) δ: 8.80 (s, 1H), 7.85 (d, J=8.4 Hz, 1H), 7.58 (dt, J=8.3, 4.2 Hz, 1H), 7.11 (d, J=8.8Hz, 2H), 7.05 (d, J=3.7 Hz, 2H), 6.90 (d, J=8.8 Hz, 2H), 4.14 (q, J =7.2 Hz, 2H), 3.98 (t, J=6.4 Hz, 2H), 3.60 (s, 3H), 2.35 (t, J=7.4 Hz, 2H), 1.89-1.79 (m, 2H), 1.79-1.69 (m, 2H), 1.68-1.60 (m, 2H), 1.60-1.48 (m, 2H), 1.26 (t, J=7.1 Hz, 3H).

Example 37

Synthesis of the Compound (II-15) N-hydroxy-2-(4-(methyl(4-quinazolinyl)amino)phenoxy)hexanamide 0.5 mmol the compound F23, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol to give the target product (II-15).

1H NMR (400 MHz, DMSO-d6) δ: 10.35 (s, 1H), 8.71 (s, 1H), 8.70 (s, 1H), 7.74 (d, J=7.8 Hz, 1H), 7.67-7.61 (m, 1H), 7.19 (d, J=8.9 Hz, 2H), 7.17-7.11 (m, 1H), 7.01 (d, J=8.8 Hz, 1H), 6.98 (d, J=8.9 Hz, 2H), 3.97 (t, J=6.4 Hz, 2H), 3.50 (s, 3H), 1.98 (t, J=7.3 Hz, 2H), 1.78-1.65 (m, 2H), 1.63-1.49 (m, 2H), 1.44-1.35 (m, 2H).

Example 38

Synthesis of the Compound methyl 4-((4-(methyl (4-quinazolinyl)amino)phenoxy)methyl)benzoate (F24)

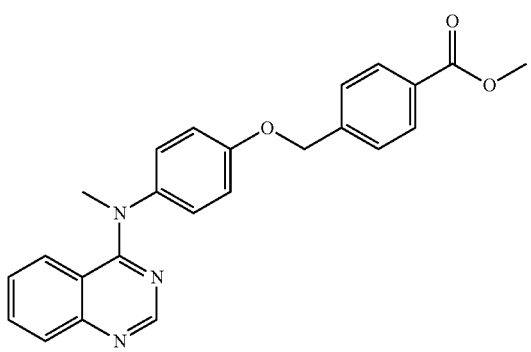 [SMILES: COC(=O)c1ccc(COc2ccc(N(C)c3ncnc4ccccc34)cc2)cc1]

1 mmol of the compound F18, 2 mmol Cs$_2$CO$_3$, 1 ml DMF and 2 mmol 4-(methyl formate) benzyl bromide methyl 4-bromobenzoate were added into a reaction flask successively, and then heated to 80° C. and allowed for reaction for 2 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether:ethyl acetate=1:1) to give a pale yellow oily liquid target product.

1H NMR (400 MHz, CDCl3) δ: 8.81 (s, 1H), 8.08 (d, J=8.3 Hz, 2H), 7.87 (d, J=8.3 Hz, 1H), 7.61-7.56 (m, 1H), 7.52 (d, J=8.2 Hz, 2H), 7.14 (d, J=8.8 Hz, 2H), 7.09 - 7.01 (m, 2H), 6.99 (d, J=8.8 Hz, 2H), 5.16 (s, 2H), 3.93 (s, 3H), 3.61 (s, 3H).

Example 39

Synthesis of the Compound (II-16) N-hydroxy-4-((4-(methyl(4-quinazolinyl)amino)phenoxy)methyl)benzoate 0.5 mmol of the compound F24, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol to give the target product (II-16).

1H NMR (400 MHz, DMSO-d6) δ: 11.24 (s, 1H), 9.12 (s, 1H), 8.71 (s, 1H), 7.94 (d, J=7.8 Hz, 1H), 7.78 (d, J=8.1 Hz, 1H), 7.74 (d, J=8.1 Hz, 1H), 7.67-7.62 (m, 1H), 7.52 (d, J=8.1 Hz, 2H), 7.41 (d, J=7.9 Hz, 1H), 7.22 (d, J=8.9 Hz, 2H), 7.15-7.10 (m, 1H), 7.08 (d, J=8.9 Hz, 2H), 6.99 (d, J=8.5 Hz, 1H), 5.19 (s, 2H), 3.51 (s, 3H).

Example 40

Synthesis of the Compound methyl 4-(4-(methyl(4-quinazolinyl)amino)phenoxy)benzoate (F25)

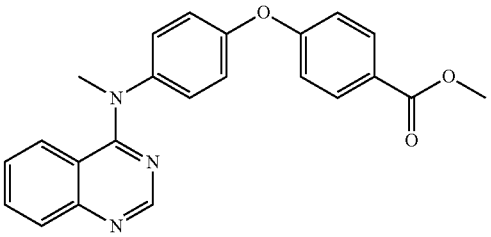 [SMILES: COC(=O)c1ccc(Oc2ccc(N(C)c3ncnc4ccccc34)cc2)cc1]

1 mmol of the compound F18, N,N-dimethylglycine, cuprous iodide, Cs$_2$CO$_3$, 1,4-dioxane and 2 mmol methyl 4-bromobenzoate were added into a reaction flask successively, and then heated to 80° C. under nitrogen atmosphere and allowed for reaction for 24 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether:ethyl acetate=1:1) to give a pale yellow oily liquid target product.

Example 41

Synthesis of the Compound (II-17) N-hydroxy-4-(4-(methyl(4-quinazolinyl)amino)phenoxy)benzamide 0.5 mmol of the compound F25, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol. The target product (II-17) was then obtained.

Example 42

Synthesis of the methyl Compound 6-(4-(methyl(4-quinazolinyl)amino)phenoxy)nicotinate (F26)

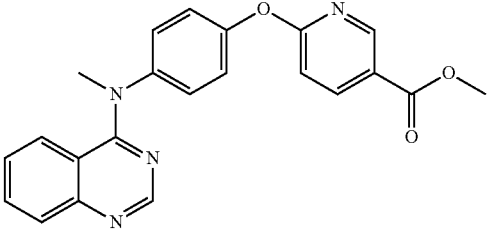 [SMILES: COC(=O)c1ccc(Oc2ccc(N(C)c3ncnc4ccccc34)cc2)nc1]

1 mmol of the compound F18, 2 mmol Cs$_2$CO$_3$, 1 ml DMF and 2 mmol methyl 2-chloro-4-nicotinate were added into a reaction flask successively, and then heated to 80° C. and allowed for reaction for 2 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether:ethyl acetate=1:1) to give a pale yellow oily liquid target product.

1H NMR (400 MHz, CDCl3) δ: 8.86 (s, 1H), 8.84 (d, J=2.0 Hz, 1H), 8.31 (dd, J=8.6, 2.4 Hz, 1H), 7.87 (d, J=8.3 Hz, 1H), 7.64-7.59 (m, 1H), 7.26 (d, J=7.6 Hz, 1H), 7.24-7.19 (m, 3H), 7.17 (dd, J=5.6, 2.9 Hz, 1H), 7.15-7.09 (m, 2H), 7.00 (d, J=8.6 Hz, 1H), 3.93 (s, 3H), 3.68 (s, 3H).

Example 43

Synthesis of the Compound (II-18) N-hydroxy-6-(4-(methyl(4-quinazolinyl)amino)phenoxy)nicotinamide 0.5 mmol of the compound F26, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol to give the target product (II-18).

1H NMR (400 MHz, DMSO-d6) δ: 8.76 (s, 1H), 8.52 (d, J=1.6 Hz, 1H), 8.17 (dd, J=8.6, 2.0 Hz, 1H), 7.78 (d, J=8.2 Hz, 1H), 7.68 (t, J=7.4 Hz, 1H), 7.32 (d, J=8.7 Hz, 2H), 7.21 (t, J=9.4 Hz, 3H), 7.08 (d, J=8.4 Hz, 1H), 7.03 (d, J=8.6 Hz, 1H), 3.58 (s, 3H).

Example 44

Synthesis of the Compound methyl 5-(4-(methyl(4-quinazolinyl)amino)phenoxy)pyridinecarboxylate (F27)

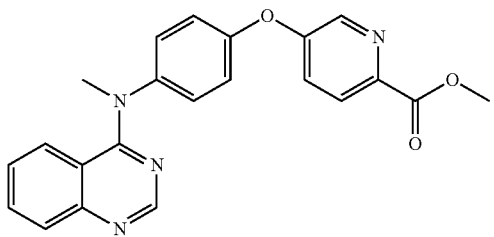 [SMILES: COC(=O)c1ccc(Oc2ccc(N(C)c3ncnc4ccccc34)cc2)cn1]

1 mmol of the compound F18, 2 mmol Cs$_2$CO$_3$, 1 ml DMF and 2 mmol methyl 5-chloropyridine-2-carboxylate were added into a reaction flask successively, and then heated to 80° C. under nitrogen atmosphere and allowed for reaction for 2 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether:ethyl acetate=1:1) to give a pale yellow oily liquid target product.

Example 45

Synthesis of the Compound (II-19) N-hydroxy-5-(4-(methyl(4-quinazolinyl)amino)phenoxypicolinamide 0.5 mmol of the compound F27, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol to give the target product (II-19).

Example 46

Synthesis of the Compound methyl 2-(4-(methyl(4-quinazolinyl)amino)phenoxy)pyrimidin-5-formate (F28)

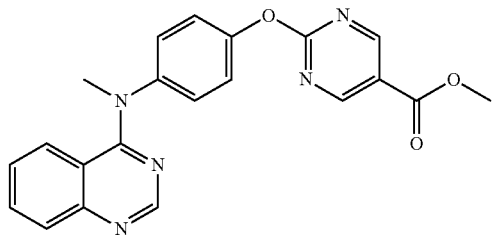 [SMILES: COC(=O)c1cnc(Oc2ccc(N(C)c3ncnc4ccccc34)cc2)nc1]

1 mmol of the compound F18, 2 mmol Cs$_2$CO$_3$, 1 ml DMF and 2 mmol methyl 2-chloropyrimidine-5-carboxylate were added into a reaction flask successively, and then heated to 80° C. under nitrogen atmosphere and allowed for reaction for 2 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether:ethyl acetate=1:1) to give a pale yellow oily liquid target product.

Example 47

Synthesis of the Compound (II-20) N-hydroxy-2-(4-(methyl(4-quinazolinyl)amino)phenoxy)pyrimidin-5-formamide 0.5 mmol of the compound F28, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol to give the target product (II-20).

Example 48

Synthesis of the Compound methyl 5-(4-(methyl(4-quinazolinyl)amino)phenoxy)pyrimidin-2-formate (F29)

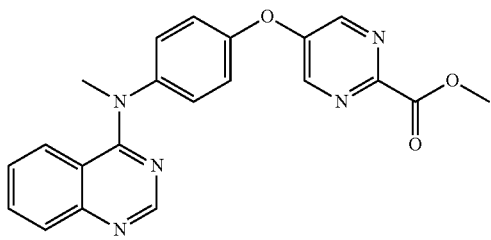 [SMILES: COC(=O)c1ncc(Oc2ccc(N(C)c3ncnc4ccccc34)cc2)cn1]

1 mmol of the compound F18, 2 mmol $Cs_2CO_3$, 1 ml DMF and 2 mmol methyl 5-bromo-2-pyrimidinecarboxylate were added into a reaction flask successively, and then heated to 80° C. under nitrogen atmosphere and allowed for reaction for 2 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether:ethyl acetate=1:1) to give a pale yellow oily liquid target product.

Example 49

Synthesis of the Compound (II-21) N-hydroxy-5-(4-(methyl(4-quinazolinyl)amino)phenoxy)pyrimidin-2-formamide 0.5 mmol of the compound F29, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol to give the target product (II-21).

Example 50

Synthesis of the Compound methyl 5-(4-(methyl(4-quinazolinyl)amino)phenoxy)pyrazin-2-formate (F30)

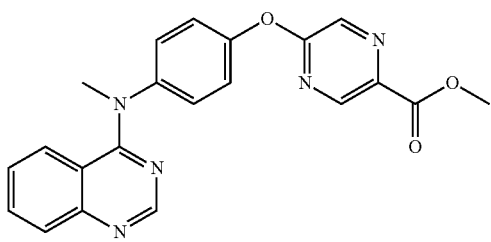 [SMILES: COC(=O)c1cnc(Oc2ccc(N(C)c3ncnc4ccccc34)cc2)cn1]

1 mmol of the compound F18, 2 mmol $Cs_2CO_3$, 1 ml DMF and 2 mmol methyl 5-bromopyrazin-2-carboxylate were added into a reaction flask successively, and then heated to 80° C. under nitrogen atmosphere and allowed for reaction for 2 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether:ethyl acetate=1:1) to give a pale yellow oily liquid target product.

Example 51

Synthesis of the Compound (II-22) N-hydroxy-5-(4-(methyl(4-quinazolinyl)amino)phenoxy)pyrazin-2-formamide 0.5 mmol of the compound F30, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol to give the target product (II-22).

Example 52

Synthesis of the Compound 4-((2-methyl-4-quinazolinyl)amino)phenol (F31)

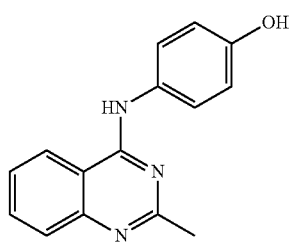 [SMILES: Cc1nc(Nc2ccc(O)cc2)c2ccccc2n1]

200 ml isopropanol was added into a reaction flask containing 100 mmol of the compound F4, and then 100 mmol of the compound F2 was added and stirred at room temperature. After the reaction was complete, the reaction solution was concentrated under elevated pressure. The residue was added into ethyl acetate and concentrated hydrochloric acid while stirring, followed by TLC detection. After the reaction was complete, saturated $NaHCO_3$ solution was added to adjust the pH value to about 7. The ethyl acetate layers were collected, and the aqueous phase was extracted with ethyl acetate. The organic layers were combined and concentrated under reduced pressure to obtain a solid product which was recrystallized from ethanol to give a light gray solid product.

Example 53

Synthesis of the Compound ethyl 2-(4-((2-methyl-4-quinazolinyl)amino)phenoxy)acetate (F32)

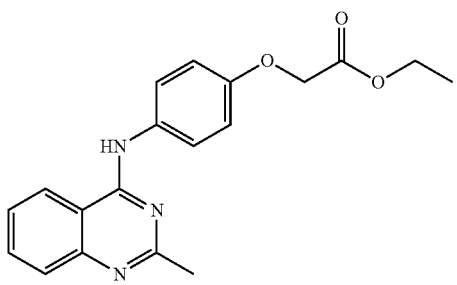 [SMILES: CCOC(=O)COc1ccc(Nc2nc(C)nc3ccccc23)cc1]

1 mmol of the compound F31, 2 mmol $Cs_2CO_3$, 1 ml DMF and 2 mmol ethyl bromoacetate were added into a reaction flask successively, and then heated to 80° C. and allowed for reaction for 2 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether:ethyl acetate=1:1) to give a pale yellow oily liquid target product.

Example 54

Synthesis of the Compound (II-23) N-hydroxy-2-(4-((2-methyl-4-quinazolinyl)amino)phenoxy)acetamide 0.5 mmol of the compound F32, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol to give the target product (II-23).

Example 55

Synthesis of the Compound ethyl 3-(4-((2-methyl-4-quinazolinyl)amino)phenoxy)propionate (F33)

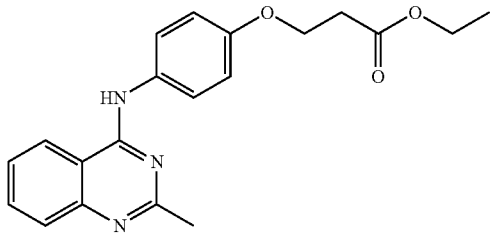 [SMILES: CCOC(=O)CCOc1ccc(Nc2nc(C)nc3ccccc23)cc1]

1 mmol of the compound F31, 2 mmol $Cs_2CO_3$, 1 ml DMF and 2 mmol ethyl bromopropionate were added into a reaction flask successively, and then heated to 80° C. and allowed for reaction for 2 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether:ethyl acetate=1:1) to give a pale yellow oily liquid target product.

1H NMR (400 MHz, DMSO-d6) δ: 9.58 (s, 1H), 8.47 (d, J=8.1 Hz, 1H), 7.79 (d, J=8 Hz, 1H), 7.77 (d, J=8.8 Hz, 2H), 7.67 (d, J=8.1 Hz, 1H), 7.52 (t, J=7.6 Hz, 1H), 6.97 (d, J=9.0 Hz, 2H), 4.22 (t, J=6.0 Hz, 2H), 3.66 (s, 3H), 2.81 (t, J=5.9 Hz, 2H), 2.47 (s, 3H).

Example 56

Synthesis of the Compound (II-24) N-hydroxy-3-(4-((2-methyl-4-quinazolinyl)amino)phenoxy)propionamide 0.5 mmol of the compound F33, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol to give the target product (II-24).

1H NMR (400 MHz, DMSO-d6) δ: 9.72 (s, 1H), 8.53 (s, 1H), 8.51 (d, J=8.4 Hz, 1H), 7.84 (t, J=7.6 Hz, 1H), 7.76 (d, J=8.1 Hz, 1H), 7.70 (d, J=9.0 Hz, 2H), 7.61 (t, J=7.6 Hz, 1H), 6.98 (d, J=9.0 Hz, 2H), 4.22 (t, J=6.0 Hz, 2H), 3.66 (s, 3H), 2.82 (t, J=6.0 Hz, 2H).

Example 57

Synthesis of the Compound ethyl 4-(4-((2-methyl-4-quinazolinyl)amino)phenoxy)butyrate (F34)

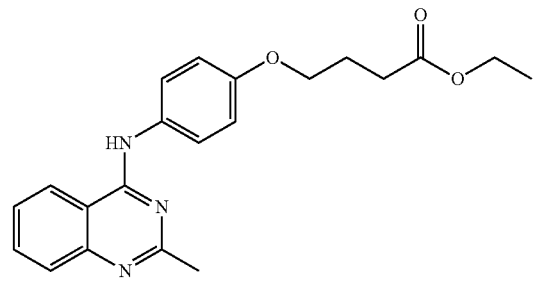 [SMILES: CCOC(=O)CCCOc1ccc(Nc2nc(C)nc3ccccc23)cc1]

1 mmol of the compound F31, 2 mmol $Cs_2CO_3$, 1 ml DMF and 2 mmol ethyl bromobutyrate were added into a reaction flask successively, and then heated to 80° C. and allowed for reaction for 2 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether:ethyl acetate=1:1) to give a pale yellow oily liquid target product.

Example 58

Synthesis of the Compound (II-25) N-hydroxy-4-(4-((2-methyl-4-quinazolinyl)amino)phenoxy)butanamide 0.5 mmol of the compound F34, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol to give the target product (II-25).

Example 59

Synthesis of the Compound ethyl 5-(4-((2-methyl-4-quinazolinyl)amino)phenoxy)valerate (F35)

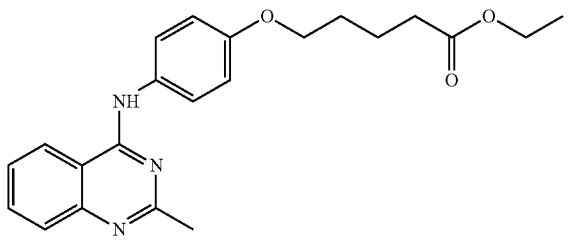 [SMILES: CCOC(=O)CCCCOc1ccc(Nc2nc(C)nc3ccccc23)cc1]

1 mmol of the compound F31, 2 mmol $Cs_2CO_3$, 1 ml DMF and 2 mmol ethyl bromovalerate were added into a reaction flask successively, and then heated to 80° C. and allowed for reaction for 2 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether:ethyl acetate=1:1) to give a pale yellow oily liquid target product.

Example 60

Synthesis of the Compound (II-26) N-hydroxy-5-(4-((2-methyl-4-quinazolinyl)amino)phenoxy)pentanamide 0.5 mmol of the compound F35, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol to give the target product (II-26).

Example 61

Synthesis of the Compound ethyl 6-(4-((2-methyl-4-quinazolinyl)amino)phenoxy)hexanoate (F36)

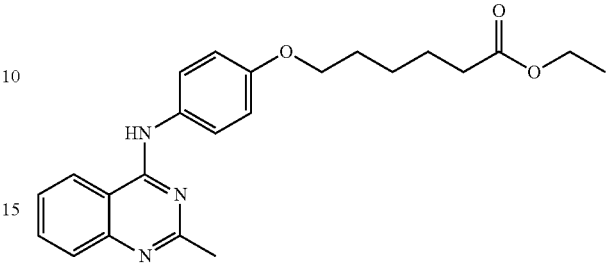

1 mmol of the compound F31, 2 mmol $Cs_2CO_3$, 1 ml DMF and 2 mmol ethyl bromohexanoate were added into a reaction flask successively, and then heated to 80° C. and allowed for reaction for 2 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether:ethyl acetate=1:1) to give a pale yellow oily liquid target product.

Example 62

Synthesis of the Compound (II-27) N-hydroxy-6-(4-((2-methyl-4-quinazolinyl)amino)phenoxy)hexanamide 0.5 mmol of the compound F36, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol to give the target product (II-27).

Example 63

Synthesis of the Compound 1-methoxy-2-(methoxymethoxy)-4-nitrobenzene (F37)

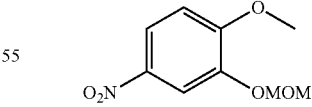

100 mmol 2-methoxy-5-nitrophenol was added into 300 ml dichloromethane while stirring in an ice-water bath. Then 120 mmol DIPEA and 200 mmol MOMCl were successively added dropwise, then stirred at room temperature. After reaction for 3 hours, the reaction solution was washed with saturated brine, water, 1N hydrochloric acid and saturated brine successively. The organic layers were spin-dried under reduced pressure and then a dark red oily target product was obtained.

1H NMR (400 MHz, CDCl3) δ: 8.04 (d, J=2.6 Hz, 1H), 7.97 (dd, J=9.0, 2.6 Hz, 1H), 6.95 (d, J=9.0 Hz, 1H), 5.30 (s, 2H), 3.99 (s, 3H), 3.54 (s, 3H).

Example 64

Synthesis of the Compound 4-methoxy-3-(methoxymethoxy)aniline (F38)

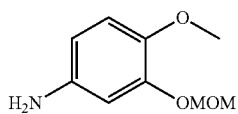

100 mmol of the compound F37 and 5 mmol 10% Pd/C were added into 250 ml methanol, followed by inletting hydrogen gas and allowing for reaction overnight at room temperature. After the reaction was complete, the reaction solution was filtered with diatomite followed by washing with ethyl acetate. The organic layers were combined and dried with NaSO4 followed by spin-drying under reduced pressure to give a dark red oily target product.

Example 65

Synthesis of the Compound 4-methoxy-3-(methoxymethoxy)-N-methylaniline (F39)

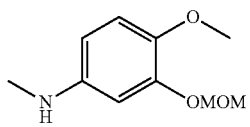

100 mmol Na was added into 200 ml methanol in batches. After the reaction was complete, 20 mmol of the compound F38 and 28 mmol paraformaldehyde were added to the reaction flask, allowed for reaction overnight at room temperature. Then 20 mmol NaBH4 was added in batches, followed by heating reflux for 2 hours. The reaction solution was concentrated under reduced pressure and then 2 N NaOH solution was added into the residue, followed by extraction with tert-butyl methyl ether. The organic phases were combined, dried over anhydrous sodium sulfate and concentrated under reduced pressure to give a dark red oily target product.

Example 66

Synthesis of the Compound 2-methoxy-5-(methyl (2-methyl-4-quinazolinyl)amino)phenol (F40)

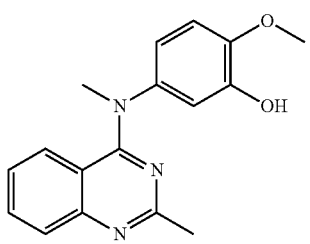 [SMILES: COc1ccc(N(C)c2nc(C)nc3ccccc23)cc1O]

200 ml isopropanol was added into a reaction flask containing 100 mmol of the compound F4, and then 100 mmol of the compound F39 was added and stirred at room temperature. After the reaction was complete, the reaction solution was concentrated under elevated pressure. The residue was added into ethyl acetate and concentrated hydrochloric acid while stirring, followed by TLC detection. After the reaction was complete, saturated NaHCO3 solution was added to adjust the pH value to about 7. The ethyl acetate layers were collected, and the aqueous phase was extracted with ethyl acetate. The organic layers were combined and concentrated under reduced pressure to obtain a solid product which was recrystallized from ethanol to give a light gray solid product.

1H NMR (400 MHz, DMSO-d6) δ: 9.31 (s, 1H), 7.64 (d, J=8.0 Hz, 1H), 7.61-7.56 (m, 1H), 7.13-7.03 (m, 2H), 6.94 (dd, J=7.1, 1.9 Hz, 1H), 6.64 (dd, J=7.4, 2.2 Hz, 2H), 3.79 (s, 3H), 3.47 (s, 3H), 2.58 (s, 3H).

Example 67

Synthesis of the Compound ethyl 2-(2-(methoxy-5-(methyl(2-methyl-4-quinazolinyl)amino)phenoxy) acetate (F41)

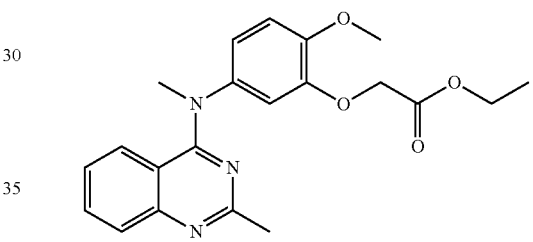

1 mmol of the compound F40, 2 mmol Cs2CO3, 1 ml DMF and 2 mmol ethyl bromoacetate were added into a reaction flask successively, and then heated to 80° C. and allowed for reaction for 2 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether:ethyl acetate=1:1) to give a pale yellow oily liquid target product.

1H NMR (400 MHz, DMSO-d6) δ: 7.64 (d, J=8.1 Hz, 1H), 7.58 (t, J=7.4 Hz, 1H), 7.06 (t, J=7.5 Hz, 1H), 6.99 (d, J=8.4 Hz, 1H), 6.98 (d, J=8.8 Hz, 1H), 6.92 (d, J=2.2 Hz, 1H), 6.75 (dd, J=8.5, 2.2 Hz, 1H), 4.74 (s, 2H), 4.01 (q, J=7.1 Hz, 2H), 3.80 (s, 3H), 3.48 (s, 3H), 2.58 (s, 3H), 1.10 (t, J=7.1 Hz, 3H).

Example 68

Synthesis of the Compound (III-1) N-hydroxy-2-(2-methoxy-5-(methyl(2-methyl-4-quinazolinyl)amino) phenoxy)acetamide 0.5 mmol of the compound F41, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol to give the target product (III-1).

1H NMR (400 MHz, DMSO-d6) δ: 10.71 (s, 1H), 8.99 (s, 1H), 7.65 (d, J=8.1 Hz, 1H), 7.59 (t, J=7.4 Hz, 1H), 7.07 (t, J=7.2 Hz, 1H), 7.04-6.93 (m, 3H), 6.72 (d, J=8.3 Hz, 1H), 4.38 (s, 2H), 3.79 (s, 3H), 3.49 (s, 3H), 2.59 (s, 3H).

Example 69

Synthesis of the Compound ethyl 2-(2-(methoxy-5-(methyl(2-methyl-4-quinazolinyl)amino)phenoxy)butyrate (F42)

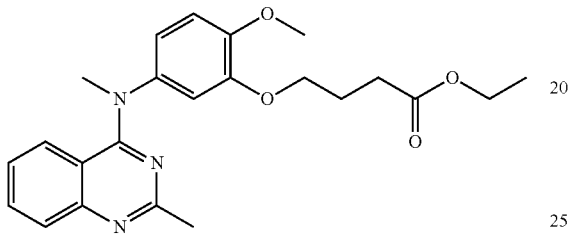 [SMILES: CCOC(=O)CCCCOc1cc(N(C)c2nc(C)nc3ccccc23)ccc1OC]

1 mmol of the compound F40, 2 mmol $Cs_2CO_3$, 1 ml DMF and 2 mmol ethyl bromobutyrate were added into a reaction flask successively, and then heated to 80° C. and allowed for reaction for 2 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether:ethyl acetate=1:1) to give a pale yellow oily liquid target product.

1H NMR (400 MHz, DMSO-d6) δ: 7.63 (d, J=8.1 Hz, 1H), 7.57 (t, J=7.5 Hz, 1H), 7.06 (t, J=7.6 Hz, 1H), 6.99 (d, J=8.2 Hz, 1H), 6.96 (d, J=3.7 Hz, 1H), 6.94 (d, J=2.4 Hz, 1H), 6.72 (dd, J=8.5, 2.4 Hz, 1H), 4.04 (q, J=7.1 Hz, 2H), 3.90 (t, J=6.4 Hz, 2H), 3.78 (s, 3H), 3.50 (s, 3H), 2.58 (s, 3H), 2.39 (t, J=7.3 Hz, 2H), 1.88 (p, J=6.8 Hz, 2H), 1.16 (t, J=7.1 Hz, 3H).

Example 70

Synthesis of the Compound (III-2) N-hydroxy-2-(2-methoxy-5-(methyl(2-methyl-4-quinazolinyl)amino)phenoxy)butanamide 0.5 mmol of the compound F42, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol to give the target product (III-2).

1H NMR (400 MHz, DMSO-d6) δ: 10.41 (s, 1H), 8.69 (s, 1H), 7.64 (d, J=8.1 Hz, 1H), 7.58 (t, J=7.2 Hz, 1H), 7.07 (t, J=7.3 Hz, 1H), 6.99 (d, J=8.6 Hz, 1H), 6.97 (d, J=2.1 Hz, 1H), 6.94 (d, J=8.6 Hz, 1H), 6.69 (dd, J=8.5, 2.1 Hz, 1H), 3.88 (t, J=6.3 Hz, 2H), 3.78 (s, 3H), 3.50 (s, 3H), 2.58 (s, 3H), 2.09 (t, J=7.4 Hz, 2H), 1.93-1.81 (m, 2H).

Example 71

Synthesis of ethyl 2-(2-(methoxy-5-(methyl(2-methyl-4-quinazolinyl)amino)phenoxy)valerate (F43)

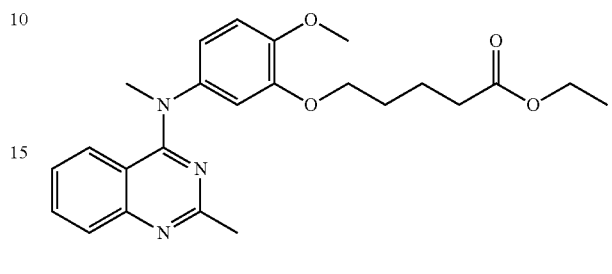

1 mmol of the compound F40, 2 mmol $Cs_2CO_3$, 1 ml DMF and 2 mmol ethyl bromovalerate were added into a reaction flask successively, and then heated to 80° C. and allowed for reaction for 2 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether:ethyl acetate=1:1) to give a pale yellow oily liquid target product.

1H NMR (400 MHz, DMSO-d6) δ: 7.64 (d, J=8.2 Hz, 1H), 7.57 (t, J=7.5 Hz, 1H), 7 7.06 (t, J=8 Hz, 1H), 7.00 (d, J=8.4 Hz, 1H), 6.96 (s, 1H), 6.94 (d, J=8.4 Hz, 1H), 6.70 (dd, J=8.5, 2.3 Hz, 1H), 4.04 (q, J=7.1 Hz, 3H), 3.88 (t, J=5.8 Hz, 2H), 3.77 (s, 3H), 3.50 (s, 3H), 2.58 (s, 3H), 2.31 (t, J=6.9 Hz, 2H), 1.67-1.59 (m, 4H), 1.17 (t, J=7.1 Hz, 3H).

Example 72

Synthesis of the Compound (III-3) N-hydroxy-2-(2-methoxy-5-(methyl(2-methyl-4-quinazolinyl)amino)phenoxy)pentanamide 0.5 mmol of the compound F43, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol to give the target product (III-3).

1H NMR (400 MHz, DMSO-d6) δ: 10.35 (s, 1H), 8.69 (s, 1H), 7.64 (d, J=8.2 Hz, 1H), 7.58 (t, J=7.5 Hz, 1H), 7.07 (t, J=7.6 Hz, 1H), 7.00 (d, J=8.4 Hz, 1H), 6.96 (d, J=2.4 Hz, 1H), 6.94 (d, J=8.8 Hz, 1H), 6.69 (dd, J=8.5, 2.3 Hz, 1H), 3.88 (t, J=5.6 Hz, 2H), 3.78 (s, 3H), 3.51 (s, 3H), 2.58 (s, 3H), 1.99-1.94 (m, 2H), 1.70-1.52 (m, 4H).

Example 73

Synthesis of ethyl 2-(2-(methoxy-5-(methyl(2-methyl-4-quinazolinyl)amino)phenoxy)hexanoate (F44)

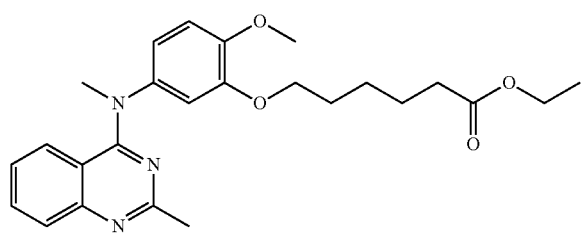 [SMILES: CCOC(=O)CCCCCOc1cc(N(C)c2nc(C)nc3ccccc23)ccc1OC]

1 mmol of the compound F40, 2 mmol Cs$_2$CO$_3$, 1 ml DMF and 2 mmol ethyl bromohexanoate were added into a reaction flask successively, and then heated to 80° C. and allowed for reaction for 2 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether:ethyl acetate=1:1) to give a pale yellow oily liquid target product.

1H NMR (400 MHz, DMSO-d6) δ: 7.64 (d, J=8.1 Hz, 1H), 7.57 (t, J=7.0 Hz, 1H), 7.06 (t, J=7.5 Hz, 1H), 7.00 (d, J=7.9 Hz, 1H), 6.94 (d, J=8.4 Hz, 1H), 6.94 (s, 1H), 6.70 (dd, J=8.5, 2.4 Hz, 1H), 4.04 (q, J=7.1 Hz, 3H), 3.86 (t, J=6.5 Hz, 2H), 3.77 (s, 3H), 3.50 (s, 3H), 2.58 (s, 3H), 2.27 (t, J=7.4 Hz, 3H), 1.65-1.58 (m, 2H), 1.57-1.49 (m, 2H), 1.41-1.27 (m, 2H), 1.17 (t, J=7.1 Hz, 3H).

Example 74

Synthesis of the Compound (III-4) N-hydroxy-2-(2-methoxy-5-(methyl(2-methyl-4-quinazolinyl)amino)phenoxy)hexanamide 0.5 mmol of the compound F44, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol to give the target product (III-4).

1H NMR (400 MHz, DMSO-d6) δ: 10.35 (s, 1H), 8.67 (s, 1H), 7.64 (d, J=8.1 Hz, 1H), 7.58 (t, J=7.1 Hz, 1H), 7.06 (t, J=7.4 Hz, 1H), 6.99 (d, J=8.4 Hz, 1H), 6.94 (dd, J=5.3, 3.0 Hz, 2H), 6.70 (dd, J=8.4, 2.1 Hz, 1H), 3.85 (t, J=6.4 Hz, 2H), 3.77 (s, 3H), 3.50 (s, 3H), 2.58 (s, 3H), 1.94 (t, J=7.2 Hz, 2H), 1.67-1.56 (m, 2H), 1.56-1.44 (m, 2H), 1.37-1.26 (m, 2H).

Example 75

Synthesis of the Compound methyl 4-((2-methoxy-5-(methyl(2-methyl-4-quinazolinyl)amino)phenoxy)methylbenzoate (F45)

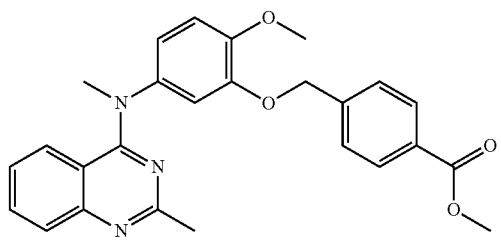 [SMILES: COC(=O)c1ccc(COc2cc(N(C)c3nc(C)nc4ccccc34)ccc2OC)cc1]

1 mmol of the compound F40, 2 mmol Cs$_2$CO$_3$, 1 ml DMF and 2 mmol methyl 4-(bromomethyl)benzoate were added into a reaction flask successively and then heated to 80° C. and allowed for reaction for 2 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether:ethyl acetate=1:1) to give a pale yellow oily liquid target product.

Example 76

Synthesis of the Compound (III-5) N-hydroxy-4-((2-methoxy-5-(methyl(2-methyl-4-quinazolinyl)amino)phenoxy)methyl)benzamide 0.5 mmol of the compound F45, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol to give the target product (III-5).

Example 77

Synthesis of the Compound methyl 4-(2-methoxy-5-(methyl(2-methyl-4-quinazolinyl)amino)phenoxy)benzoate (F46)

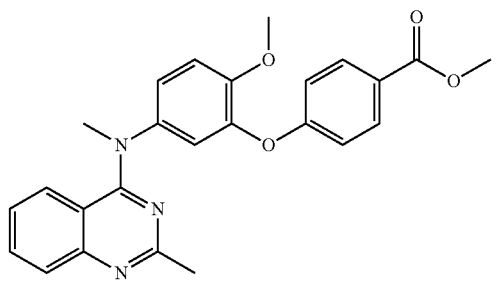 [SMILES: COC(=O)c1ccc(Oc2cc(N(C)c3nc(C)nc4ccccc34)ccc2OC)cc1]

1 mmol of the compound F40, N,N-dimethylglycine, cuprous iodide, Cs$_2$CO$_3$, 1,4-dioxane and 2 mmol methyl 4-bromobenzoate were added into a reaction flask successively, and then heated to 80° C. under nitrogen atmosphere and allowed for reaction for 24 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether:ethyl acetate=1:1) to give a pale yellow oily liquid target product.

Example 78

Synthesis of the Compound (III-6) N-hydroxy-4-(2-methoxy-5-(methyl(2-methyl-4-quinazolinyl)amino)phenoxy)benzamide 0.5 mmol of the compound F46, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol. The target product (III-6) was then obtained.

Example 79

Synthesis of the methyl Compound 6-(2-methoxy-5-(methyl(2-methyl-4-quinazolinyl)amino)phenoxy)nicotinate (F47)

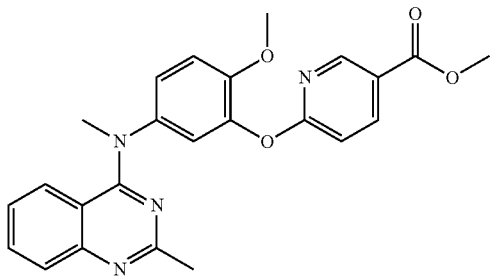 [SMILES: COC(=O)c1ccc(Oc2cc(N(C)c3nc(C)nc4ccccc34)ccc2OC)nc1]

1 mmol of the compound F40, N,N-dimethylglycine, cuprous iodide, Cs$_2$CO$_3$, 1,4-dioxane and 2 mmol methyl 6-chloronicotinate were added into a reaction flask successively, and then heated to 80° C. under nitrogen atmosphere and allowed for reaction for 24 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether:ethyl acetate=1:1) to give a pale yellow oily liquid target product.

Example 80

Synthesis of the Compound (III-7) N-hydroxy-6-(2-methoxy-5-(methyl(2-methyl-4-quinazolinyl)amino)phenoxy)nicotinamide 0.5 mmol of the compound F47, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol. The target product (III-7) was then obtained.

Example 81

Synthesis of the Compound methyl 5-(2-methoxy-5-(methyl(2-methyl-4-quinazolinyl)amino)phenoxy)pyridinecarboxylate (F48)

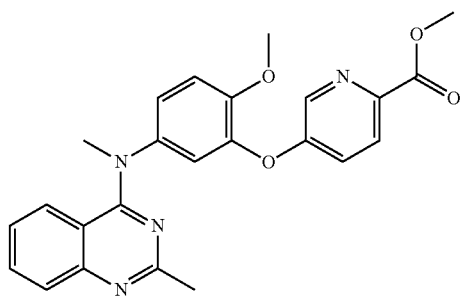 [SMILES: COC(=O)c1ccc(Oc2cc(N(C)c3nc(C)nc4ccccc34)ccc2OC)cn1]

1 mmol of the compound F40, N,N-dimethylglycine, cuprous iodide, Cs$_2$CO$_3$, 1,4-dioxane and 2 mmol methyl 5-chloropyridine-2-carboxylate were added into a reaction flask successively, and then heated to 80° C. under nitrogen atmosphere and allowed for reaction for 24 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether: ethyl acetate=1:1) to give a pale yellow oily liquid target product.

Example 82

Synthesis of the Compound (III-8) N-hydroxy-5-(2-methoxy-5-(methyl(2-methyl-4-quinazolinyl)amino)phenoxy)picolinamide 0.5 mmol of the compound F48, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol. The target product (III-8) was then obtained.

Example 83

Synthesis of the Compound methyl 2-(2-methoxy-5-(methyl(2-methyl-4-quinazolinyl)amino)phenoxy)pyrimidin-5-formate (F49)

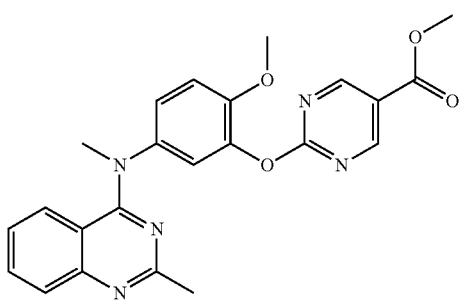 [SMILES: COC(=O)c1cnc(Oc2cc(N(C)c3nc(C)nc4ccccc34)ccc2OC)nc1]

1 mmol of the compound F40, N,N-dimethylglycine, cuprous iodide, $Cs_2CO_3$, 1,4-dioxane and 2 mmol methyl 2-chloropyrimidine-5-carboxylate were added into a reaction flask successively, and then heated to 80° C. under nitrogen atmosphere and allowed for reaction for 24 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether: ethyl acetate=1:1) to give a pale yellow oily liquid target product.

Example 84

Synthesis of the Compound (III-9) N-hydroxy-2-(2-methoxy-5-(methyl(2-methyl-4-quinazolinyl)amino)phenoxy)pyrimidin-5-formamide 0.5 mmol of the compound F49, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol. The target product (III-9) was then obtained.

Example 85

Synthesis of the Compound methyl 5-(2-methoxy-5-(methyl(2-methyl-4-quinazolinyl)amino)phenoxy)pyrimidin-2-formate (F50)

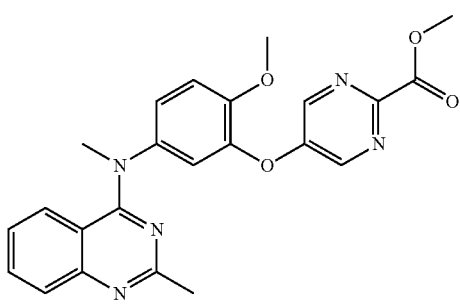 [SMILES: COC(=O)c1ncc(Oc2cc(N(C)c3nc(C)nc4ccccc34)ccc2OC)cn1]

1 mmol of the compound F40, N,N-dimethylglycine, cuprous iodide, $Cs_2CO_3$, 1,4-dioxane and 2 mmol methyl 5-bromo-2-pyrimidinecarboxylate were added into a reaction flask successively, and then heated to 80° C. under nitrogen atmosphere and allowed for reaction for 24 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether: ethyl acetate=1:1) to give a pale yellow oily liquid target product.

Example 86

Synthesis of the Compound (III-10) N-hydroxy-5-(2-methoxy-5-(methyl(2-methyl-4-quinazolinyl)amino)phenoxy)pyrimidin-2-formamide 0.5 mmol of the compound F50, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol. The target product (III-10) was then obtained.

Example 87

Synthesis of the Compound methyl 5-(2-methoxy-5-(methyl(2-methyl-4-quinazolinyl)amino)phenoxy)pyrazin-2-formate (F51)

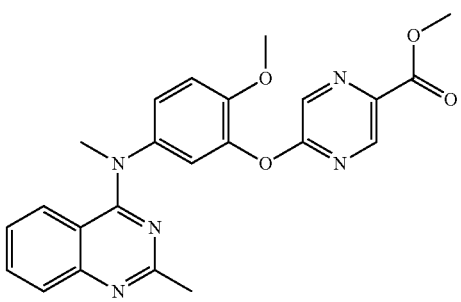 [SMILES: COC(=O)c1cnc(Oc2cc(N(C)c3nc(C)nc4ccccc34)ccc2OC)cn1]

1 mmol of the compound F40, N,N-dimethylglycine, cuprous iodide, $Cs_2CO_3$, 1,4-dioxane and 2 mmol methyl 5-bromopyrazin-2-carboxylate were added into a reaction flask successively, and then heated to 80° C. under nitrogen atmosphere and allowed for reaction for 24 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether: ethyl acetate=1:1) to give a pale yellow oily liquid target product.

Example 88

Synthesis of the Compound (III-11) N-hydroxy-5-(2-methoxy-5-(methyl(2-methyl-4-quinazolinyl)amino)phenoxy)pyrazin-2-formamide 0.5 mmol of the compound F51, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol. The target product (III-11) was then obtained.

Example 89

Synthesis of 1-(methoxymethoxy)-3-nitrobenzene (F52)

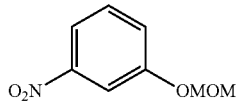

100 mmol 3-nitrophenol was added into 300 ml dichloromethane, while stirring in an ice-water bath. Then 120 mmol DIPEA and 200 mmol MOMCl were successively added dropwise, and stirred at room temperature. After reaction for 3 hours, the reaction solution was washed with saturated brine, water, 1N hydrochloric acid and saturated brine successively. The organic layers were spin-dried under reduced pressure and then a dark red oily target product was obtained.

Example 90

Synthesis of 3-(methoxymethoxy)aniline (F53)

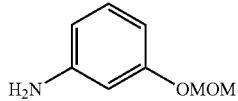

100 mmol of the compound F52 and 5 mmol 10% Pd/C were added into 250 ml methanol, followed by inletting hydrogen gas and allowing for reaction overnight at room temperature. After the reaction was complete, the reaction solution was filtered with diatomite followed by washing with ethyl acetate. The organic layers were combined and dried with NaSO₄ followed by spin-drying under reduced pressure to give a dark red oily target product.

Example 91

Synthesis of 3-(methoxymethoxy)-N-methylaniline (F54)

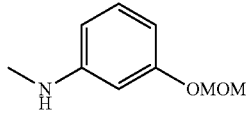

100 mmol Na was added into 200 ml methanol in batches. After the reaction was complete, 20 mmol of the compound F53 and 28 mmol paraformaldehyde were added to the reaction flask, allowed for reaction overnight at room temperature. Then 20 mmol NaBH4 was added in batches, followed by heating reflux for 2 hours. The reaction solution was concentrated under reduced pressure and then 2 N NaOH solution was added into the residue, followed by extraction with tert-butyl methyl ether. The organic phases were combined, dried over anhydrous sodium sulfate and concentrated under reduced pressure to give a dark red oily target product.

Example 92

Synthesis of 3-(methyl(2-methyl-4-quinazolinyl)amino)phenol (F55)

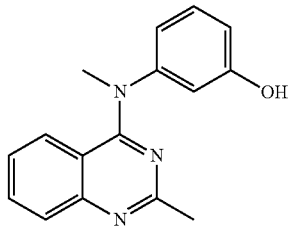 [SMILES: Cc1nc(N(C)c2cccc(O)c2)c2ccccc2n1]

200 ml isopropanol was added into a reaction flask containing 100 mmol of the compound F4, and then 100 mmol of the compound F54 was added and stirred at room temperature. After the reaction was complete, the reaction solution was concentrated under elevated pressure. The residue was added into ethyl acetate and concentrated hydrochloric acid while stirring, followed by TLC detection. After the reaction was complete, saturated NaHCO₃ solution was added to adjust the pH value to about 7. The ethyl acetate layers were collected, and the aqueous phase was extracted with ethyl acetate. The organic layers were combined and concentrated under reduced pressure to obtain a solid product which was recrystallized from ethanol to give a light gray solid product.

Example 93

Synthesis of ethyl 2-(3-(methyl(2-methyl-4-quinazolinyl)amino)phenoxy)acetate (F56)

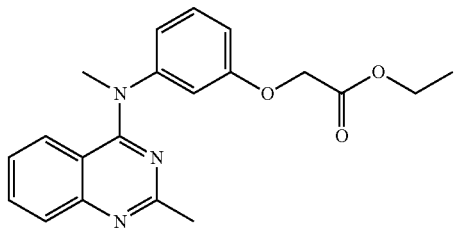 [SMILES: CCOC(=O)COc1cccc(N(C)c2nc(C)nc3ccccc23)c1]

1 mmol of the compound F55, 2 mmol Cs₂CO₃, 1 ml DMF and 2 mmol ethyl bromoacetate were added into a reaction flask successively, and then heated to 80° C. and allowed for reaction for 2 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether:ethyl acetate=1:1) to give a pale yellow oily liquid target product.

1H NMR (400 MHz, DMSO-d6) δ: 7.71 (d, J=8.2 Hz, 1H), 7.65 (t, J=7.5 Hz, 1H), 7.34 (t, J=8.1 Hz, 1H), 7.11 (t, J=7.5 Hz, 1H), 6.99 (d, J=8.5 Hz, 1H), 6.93 (dd, J=14.1, 8.0 Hz, 3H), 4.69 (s, 2H), 4.13 (q, J=7.1 Hz, 2H), 3.31 (s, 3H), 2.54 (s, 3H), 1.19 (t, J=7.0 Hz, 3H).

Example 94

Synthesis of the Compound (III-12) N-hydroxy-2-(3-(methyl(2-methyl-4-quinazolinyl)amino)phenoxy)acetamide 0.5 mmol of the compound F56, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol to give the target product (III-12).

MS (ESI, m/z): 339.36 [M+H]+.

Example 95

Synthesis of the Compound ethyl 2-(3-(methyl(2-methyl-4-quinazolinyl)amino)phenoxy)butyrate (F57)

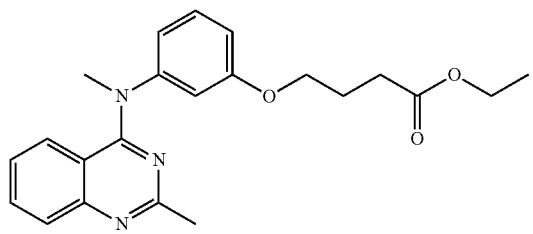 [SMILES: CCOC(=O)CCCOc1cccc(N(C)c2nc(C)nc3ccccc23)c1]

1 mmol of the compound F55, 2 mmol Cs$_2$CO$_3$, 1 ml DMF and 2 mmol ethyl bromobutyrate were added into a reaction flask successively, and then heated to 80° C. and allowed for reaction for 2 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether:ethyl acetate=1:1) to give a pale yellow oily liquid target product.

1H NMR (400 MHz, DMSO-d6) δ: 7.67 (d, J=8.1 Hz, 1H), 7.60 (t, J=7.2 Hz, 1H), 7.31 (t, J=8.1 Hz, 1H), 7.07 (t, J=7.5 Hz, 1H), 7.01-6.97 (m, 1H), 6.94 (s, 1H), 6.88 (s, 1H), 6.82 (d, J=8.0 Hz, 1H), 4.13 (t, J=7.0 Hz, 2H), 4.01 (q, J=7.1 Hz, 2H), 3.31 (s, 3H), 2.59 (s, 3H), 2.40 (t, J=7.1 Hz, 2H), 1.98-1.89 (m, 2H), 1.14 (t, J=7.1 Hz, 3H).

Example 96

Synthesis of the Compound (III-13) N-hydroxy-2-(3-(methyl(2-methyl-4-quinazolinyl)amino)phenoxy)butanamide 0.5 mmol of the compound F57, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol to give the target product (III-13).

MS (ESI, m/z): 367.58 [M+H]+.

Example 97

Synthesis of the Compound ethyl 2-(3-(methyl(2-methyl-4-quinazolinyl)amino)phenoxy)valerate (F58)

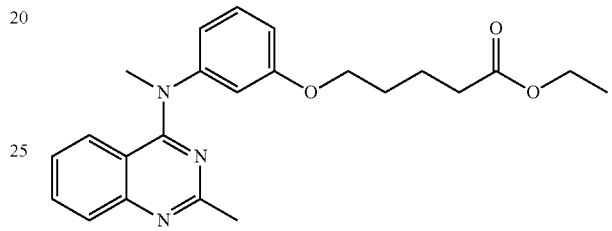

1 mmol of the compound F55, 2 mmol Cs$_2$CO$_3$, 1 ml DMF and 2 mmol ethyl bromovalerate were added into a reaction flask successively, and then heated to 80° C. and allowed for reaction for 2 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether:ethyl acetate=1:1) to give a pale yellow oily liquid target product.

1H NMR (400 MHz, DMSO-d6) δ: 7.66 (d, J=8.2 Hz, 1H), 7.60 (t, J=7.3 Hz, 1H), 7.31 (t, J=8.1 Hz, 1H), 7.06 (t, J=7.4 Hz, 1H), 6.96 (t, J=8.1 Hz, 2H), 6.86 (s, 1H), 6.80 (d, J=7.8 Hz, 1H), 4.10 (t, J=7.1 Hz, 2H), 4.04-3.97 (m, 2H), 3.31 (s, 3H), 2.59 (s, 3H), 2.36 (t, J=7.1 Hz, 2H), 1.68 (dd, J=14.1, 7.2 Hz, 2H), 1.60 (dd, J=14.6, 7.4 Hz, 2H), 1.13 (t, J=7.1 Hz, 3H).

Example 98

Synthesis of the Compound (III-14) N-hydroxy-2-(3-(methyl(2-methyl-4-quinazolinyl)amino)phenoxy)pentanamide 0.5 mmol of the compound F58, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol to give the target product (III-14).

MS (ESI, m/z): 381.65 [M+H]+.

Example 99

Synthesis of the Compound ethyl 2-(3-(methyl(2-methyl-4-quinazolinyl)amino)phenoxy)hexanoate (F59)

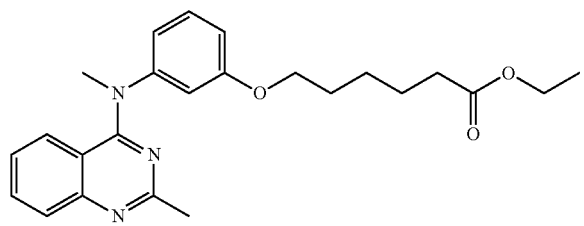 [SMILES: CCOC(=O)CCCCCOc1cccc(N(C)c2nc(C)nc3ccccc23)c1]

1 mmol of the compound F55, 2 mmol Cs₂CO₃, 1 ml DMF and 2 mmol ethyl bromohexanoate were added into a reaction flask successively, and then heated to 80° C. and allowed for reaction for 2 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether:ethyl acetate=1:1) to give a pale yellow oily liquid target product.
MS (ESI, m/z): 408.21 [M+H]+

Example 100

Synthesis of the Compound (III-15) N-hydroxy-2-(3-(methyl(2-methyl-4-quinazolinyl)amino)phenoxy)hexanamide 0.5 mmol of the compound F59, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol to give the target product (III-15).
MS (ESI, m/z): 395.36 [M+H]⁺

Example 101

Synthesis of the Compound methyl 4-((3-(methyl(2-methyl-4-quinazolinyl)amino)phenoxy)methyl)benzoate (F60)

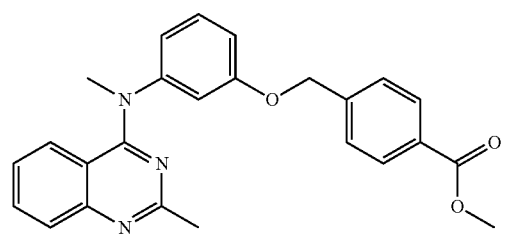 [SMILES: COC(=O)c1ccc(COc2cccc(N(C)c3nc(C)nc4ccccc34)c2)cc1]

1 mmol of the compound F55, 2 mmol Cs₂CO₃, 1 ml DMF and 2 mmol methyl 4-(bromomethyl)benzoate were added into a reaction flask successively, and then heated to 80° C. and allowed for reaction for 2 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether:ethyl acetate=1:1) to give a pale yellow oily liquid target product.

Example 102

Synthesis of the Compound (III-16) N-hydroxy-4-((3-(methyl(2-methyl-4-quinazolinyl)amino)phenoxy)methyl)benzamide 0.5 mmol of the compound F60, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol to give the target product (III-16).

Example 103

Synthesis of the Compound methyl 4-(3-(methyl(2-methyl-4-quinazolinyl)amino)phenoxy)benzoate (F61)

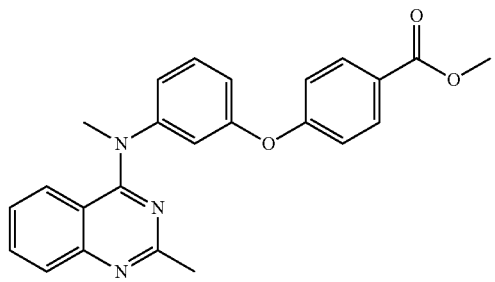 [SMILES: COC(=O)c1ccc(Oc2cccc(N(C)c3nc(C)nc4ccccc34)c2)cc1]

1 mmol of the compound F55, N,N-dimethylglycine, cuprous iodide, Cs₂CO₃, 1,4-dioxane and 2 mmol methyl 4-bromobenzoate were added into a reaction flask successively, and then heated to 80° C. under nitrogen atmosphere and allowed for reaction for 24 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether:ethyl acetate=1:1) to give a pale yellow oily liquid target product.

Example 104

Synthesis of the Compound (III-17) N-hydroxy-4-(3-(methyl(2-methyl-4-quinazolinyl)amino)phenoxy)benzamide 0.5 mmol of the compound F61, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol. The target product (III-17) was then obtained.

Example 105

Synthesis of the Compound methyl 6-(3-(methyl(2-methyl-4-quinazolinyl)amino)phenoxy)nicotinate (F62)

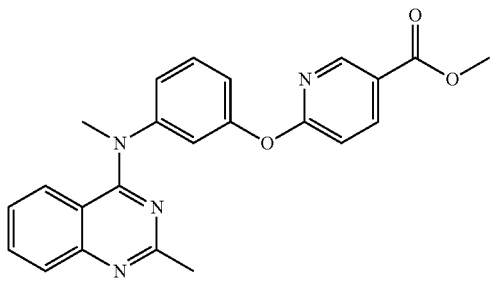

1 mmol of the compound F55, N,N-dimethylglycine, cuprous iodide, Cs$_2$CO$_3$, 1,4-dioxane and 2 mmol methyl 6-chloronicotinate were added into a reaction flask successively, and then heated to 80° C. under nitrogen atmosphere and allowed for reaction for 24 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether:ethyl acetate=1:1) to give a pale yellow oily liquid target product.

Example 106

Synthesis of the Compound (III-18) N-hydroxy-6-(3-(methyl(2-methyl-4-quinazolinyl)amino)phenoxy) nicotinamide 0.5 mmol of the compound F62, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol. The target product (III-18) was then obtained.

Example 107

Synthesis of the Compound methyl 5-(3-(methyl(2-methyl-4-quinazolinyl)amino)phenoxy)pyridinecarboxylate (F63)

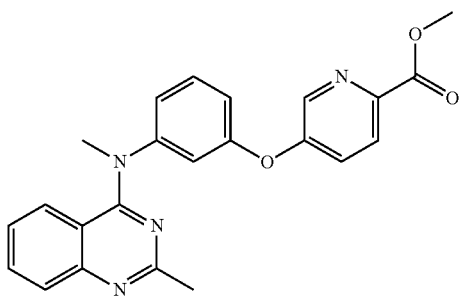 [SMILES: COC(=O)c1ccc(Oc2cccc(N(C)c3nc(C)nc4ccccc34)c2)cn1]

1 mmol of the compound F55, N,N-dimethylglycine, cuprous iodide, Cs$_2$CO$_3$, 1,4-dioxane and 2 mmol methyl 5-chloropyridine-2-carboxylate were added into a reaction flask successively, and then heated to 80° C. under nitrogen atmosphere and allowed for reaction for 24 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether:ethyl acetate=1:1) to give a pale yellow oily liquid target product.

Example 108

Synthesis of the Compound (III-19) N-hydroxy-5-(3-(methyl(2-methyl-4-quinazolinyl)amino)phenoxy) picolinamide 0.5 mmol of the compound F63, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol. The target product (III-19) was then obtained.

Example 109

Synthesis of the Compound methyl 2-(3-(methyl(2-methyl-4-quinazolinyl)amino)phenoxy)pyrimidin-5-formate (F64)

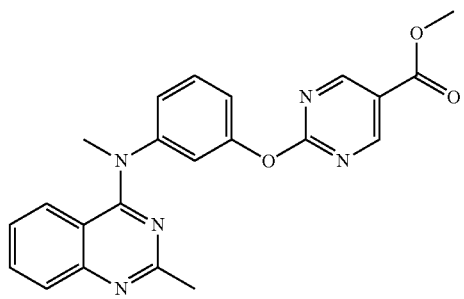 [SMILES: COC(=O)c1cnc(Oc2cccc(N(C)c3nc(C)nc4ccccc34)c2)nc1]

1 mmol of the compound F55, N,N-dimethylglycine, cuprous iodide, Cs$_2$CO$_3$, 1,4-dioxane and 2 mmol methyl 2-chloropyrimidine-5-carboxylate were added into a reaction flask successively, and then heated to 80° C. under nitrogen atmosphere and allowed for reaction for 24 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether: ethyl acetate=1:1) to give a pale yellow oily liquid target product.

Example 110

Synthesis of the Compound (III-20) N-hydroxy-2-(3-(methyl(2-methyl-4-quinazolinyl)amino)phenoxy) pyrimidin-5-formamide 0.5 mmol of the compound F64, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol. The target product (III-20) was then obtained.

Example 111

Synthesis of the Compound methyl 5-(3-(methyl(2-methyl-4-quinazolinyl)amino)phenoxy)pyrimidin-2-formate (F65)

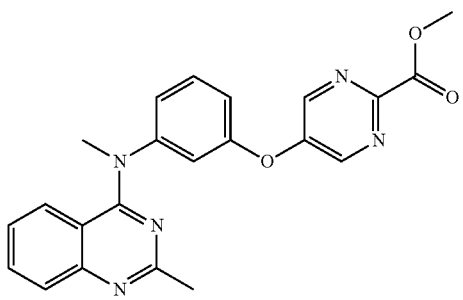 [SMILES: COC(=O)c1ncc(Oc2cccc(N(C)c3nc(C)nc4ccccc34)c2)cn1]

1 mmol of the compound F55, N,N-dimethylglycine, cuprous iodide, Cs$_2$CO$_3$, 1,4-dioxane and 2 mmol methyl 5-bromo-2-pyrimidinecarboxylate were added into a reaction flask successively, and then heated to 80° C. under nitrogen atmosphere and allowed for reaction for 24 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether: ethyl acetate=1:1) to give a pale yellow oily liquid target product.

Example 112

Synthesis of the Compound (III-21) N-hydroxy-5-(3-(methyl(2-methyl-4-quinazolinyl)amino)phenoxy)pyrimidin-2-formamide 0.5 mmol of the compound F65, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol. The target product (III-21) was then obtained.

Example 113

Synthesis of the Compound methyl 5-(3-(methyl(2-methyl-4-quinazolinyl)amino)phenoxy)pyrazin-2-formate (F66)

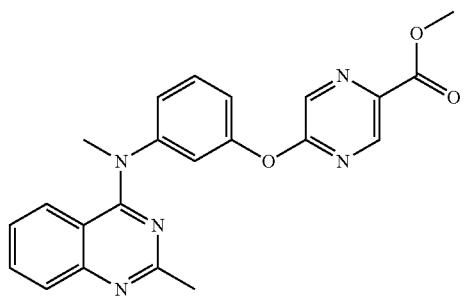 [SMILES: COC(=O)c1cnc(Oc2cccc(N(C)c3nc(C)nc4ccccc34)c2)cn1]

1 mmol of the compound F55, N,N-dimethylglycine, cuprous iodide, Cs$_2$CO$_3$, 1,4-dioxane and 2 mmol methyl 5-bromopyrazin-2-carboxylate were added into a reaction flask successively, and then heated to 80° C. under nitrogen atmosphere and allowed for reaction for 24 hours. Water was added after the reaction was complete, followed by extraction with ethyl acetate. The organic° phases were combined and then dried over anhydrous sodium sulfate, followed by concentration under elevated pressure and then purification by silica gel column (the eluant was petroleum ether: ethyl acetate=1:1) to give a pale yellow oily liquid target product.

Example 114

Synthesis of the Compound (III-22) N-hydroxy-5-(3-(methyl(2-methyl-4-quinazolinyl)amino)phenoxy) pyrazin-2-formamide 0.5 mmol of the compound F66, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol. The target product (III-22) was then obtained.

Example 115

Synthesis of the Compound ethyl 4-(2-methoxy-5-nitrophenoxy)butyrate (F67)

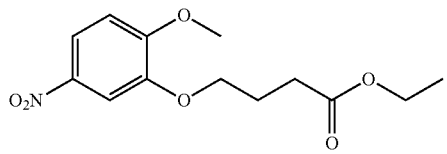

2-methoxy-5-nitrophenol and 20% KOH aqueous solution were added into a reaction flask. The mixture was allowed for reaction at 60° C. for 3 hours and then 6 N HCl was added to adjust the pH value to about 7, followed by extraction with ethyl acetate. The organic phases were combined and then washed with saturated NaCO₃ for 3 times. The resulting organic phases were concentrated under reduced pressure to give the target product.

Example 116

Synthesis of the Compound ethyl 4-(5-amino-2-methoxyphenoxy)butyrate (F68)

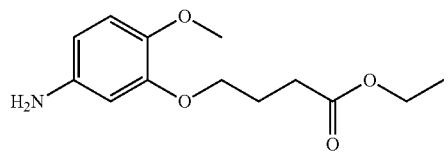 [SMILES: CCOC(=O)CCCOc1cc([N+](=O)[O-])ccc1OC]

100 mmol of the compound F67 and 5 mmol 10% Pd/C were added into 250 ml methanol, followed by inletting hydrogen gas and allowing for reaction overnight at room temperature. After the reaction was complete, the reaction solution was filtered with diatomite followed by washing with ethyl acetate. The organic layers were combined and dried with NaSO₄ followed by spin-drying under reduced pressure to give a dark red oily target product.

Example 117

Synthesis of the Compound ethyl 4-(2-methoxy-5-((2-methyl-4-quinazolinyl)amino)phenoxy)butyrate (F69)

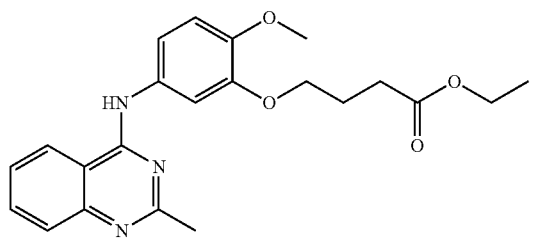 [SMILES: CCOC(=O)CCCOc1cc(Nc2nc(C)nc3ccccc23)ccc1OC]

200 ml isopropanol was added into a reaction flask containing 100 mmol of the compound F4, and then 100 mmol of the compound F68 was added and stirred at room temperature. After the reaction was complete, the reaction solution was concentrated under elevated pressure. The residue was added into ethyl acetate and concentrated hydrochloric acid while stirring, followed by TLC detection. After the reaction was complete, saturated NaHCO₃ solution was added to adjust the pH value to about 7. The ethyl acetate layers were collected, and the aqueous phase was extracted with ethyl acetate. The organic layers were combined and concentrated under reduced pressure to obtain a solid product which was recrystallized from ethanol to give a light gray solid product.

Example 118

Synthesis of the Compound ethyl 4-(5-(ethyl(2-methyl-4-quinazolinyl)amino)-2-methoxyphenoxy)butyrate (F70)

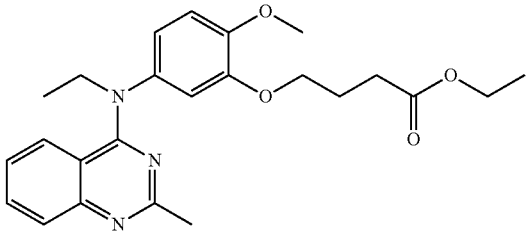 [SMILES: CCOC(=O)CCCOc1cc(N(CC)c2nc(C)nc3ccccc23)ccc1OC]

1 mmol of the compound F69, 2 mmol Cs₂CO₃, 1 ml DMF and 2 mmol iodoethane were added into a reaction flask successively, and then heated to 80° C. and allowed for reaction for 2 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether:ethyl acetate=1:1) to give a pale yellow oily liquid target product.

Example 119

Synthesis of the Compound (IV-1)4-(5-(ethyl(2-methyl-4-quinazolinyl)amino)-2-methoxyphenyl)-N-hydroxybutanamide 0.5 mmol of the compound F70, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol. The target product (IV-1) was then obtained.

Example 120

Synthesis of the Compound ethyl 4-(2-methoxy-5-((2-methyl-4-quinazolinyl)(propyl)amino)phenoxy)butyrate (F71)

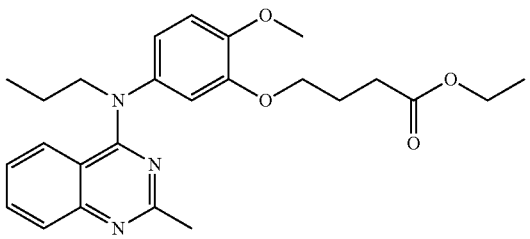 [SMILES: CCCN(c1ccc(OC)c(OCCCC(=O)OCC)c1)c1nc(C)nc2ccccc12]

1 mmol of the compound F69, 2 mmol Cs₂CO₃, 1 ml DMF and 2 mmol iodopropane were added into a reaction flask successively, and then heated to 80° C. and allowed for reaction for 2 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether:ethyl acetate=1:1) to give a pale yellow oily liquid target product.

Example 121

Synthesis of the Compound (IV-2) N-hydroxy-4-(2-methoxy-5-((2-methyl-4-quinazolinyl)(propyl)amino)phenoxy)butanamide 0.5 mmol of the compound F71, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol. The target product (IV-2) was then obtained.

Example 122

Synthesis of the Compound ethyl 4-(5-(butyl(2-methyl-4-quinazolinyl)amino)-2-methoxyphenoxy)butyrate (F72)

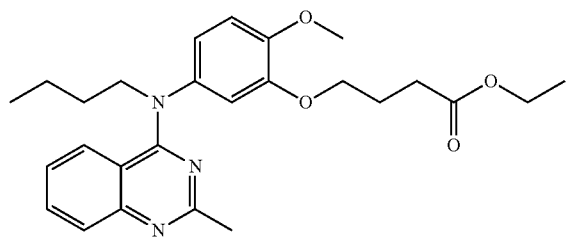 [SMILES: CCCCN(c1ccc(OC)c(OCCCC(=O)OCC)c1)c1nc(C)nc2ccccc12]

1 mmol of the compound F69, 2 mmol Cs$_2$CO$_3$, 1 ml DMF and 2 mmol iodobutane were added into a reaction flask successively, and then heated to 80° C. and allowed for reaction for 2 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether:ethyl acetate=1:1) to give a pale yellow oily liquid target product.

Example 123

Synthesis of the Compound (IV-3)4-(5-(butyl(2-methyl-4-quinazolinyl)amino)-2-methoxyphenyl)-N-hydroxybutanamide 0.5 mmol of the compound F72, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol. The target product (IV-3) was then obtained.

Example 124

Synthesis of the Compound ethyl 4-(2-methoxy-5-((2-methyl-4-quinazolinyl)(pentyl)amino)phenoxy)butyrate (F73)

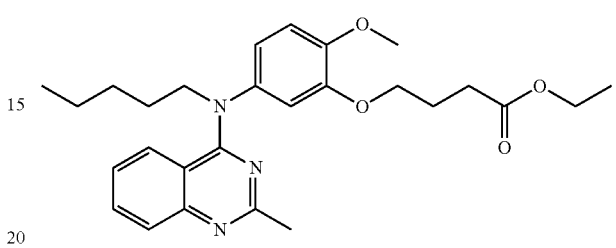

1 mmol of the compound F69, 2 mmol Cs$_2$CO$_3$, 1 ml DMF and 2 mmol iodopropane were added into a reaction flask successively, and then heated to 80° C. and allowed for reaction for 2 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether:ethyl acetate=1:1) to give a pale yellow oily liquid target product.

Example 125

Synthesis of the Compound (IV -4) N-hydroxy-4-(2-methoxy-5-((2-methyl-4-quinazolinyl)(pentyl)amino)phenoxy)butanamide 0.5 mmol of the compound F73, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol. The target product (IV-4) was then obtained.

Example 126

Synthesis of the Compound ethyl 4-(2-methoxy-5-((methoxymethyl)(2-methyl-4-quinazolinyl)amino)phenoxy)butyrate (F74)

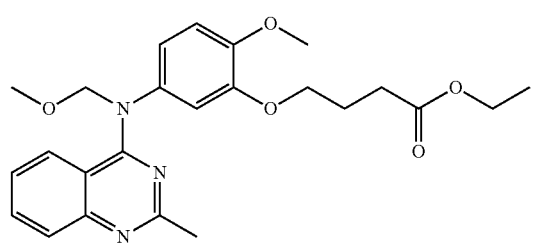

1 mmol of the compound F69, 2 mmol $Cs_2CO_3$, 1 ml DMF and 2 mmol MOMCl were added into a reaction flask successively, and then heated to 80° C. and allowed for reaction for 2 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether: ethyl acetate=1:1) to give a pale yellow oily liquid target product.

Example 127

Synthesis of the Compound (IV -5) N-hydroxy-4-(2-methoxy-5-((methoxymethyl)(2-methyl-4-quinazolinyl)amino)phenoxy)butanamide 0.5 mmol of the compound F74, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol. The target product (IV-5) was then obtained.

Example 128

Synthesis of the Compound ethyl 4-(2-methoxy-5-(((methoxymethoxy)methyl)(2-methyl-4-quinazolinyl)amino)phenoxy)butyrate (F75)

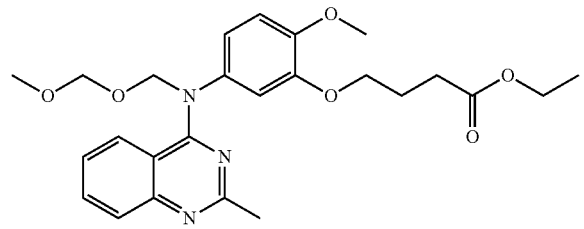 [SMILES: CCCCCN(c1ccc(OC)c(OCCCC(=O)OCC)c1)c1nc(C)nc2ccccc12]

1 mmol of the compound F69, 2 mmol $Cs_2CO_3$, 1 ml DMF and 2 mmol 1-iodomethylmethoxymethoxy were added into a reaction flask successively, and then heated to 80° C. and allowed for reaction for 2 hours. Water was added after the reaction was complete, followed by extraction with ethyl acetate. The organic phases were combined and then dried over anhydrous sodium sulfate, followed by concentration under elevated pressure and then purification by silica gel column (the eluant was petroleum ether:ethyl acetate=1:1) to give a pale yellow oily liquid target product.

Example 129

Synthesis of the Compound (IV -6) N-hydroxy-4-(2-methoxy-5-(((methoxymethoxy)methyl)(2-methyl-4-quinazolinyl)amino)phenoxy)butanamide 0.5 mmol of the compound F75, 10 mmol of methanol solution containing 2.5 ml 4 N hydroxylamine and 0.75 mmol KOH were added into a reaction flask successively and then stirred overnight at room temperature. The reaction solution was poured into 50 ml water, followed by adjusting the pH value to pH=7~8 with glacial acetic acid to produce a large amount of white solid, which was dried by suction filtration and then recrystallized from ethanol. The target product (IV-6) was then obtained.

Example 130

The following experiments were used to determine the activity of the compounds of the present invention to inhibit HDAC kinases, as well as in vitro anti-proliferative activity and in vivo anti-tumor activity thereof.

1. In Vitro Assay for Determining the HDAC Inhibitory Activity of the Small Molecule Compounds of the Present Invention The HDAC inhibitory activity was determined by fluorescence-coupled acetylated peptide substrate assay (Lys-Ac-AMC). HDAC1 protein was purchased from BPS Bioscience, and the reaction buffer system was a modified tris(hydroxymethyl)aminomethane buffer (pH 7.0). The small molecule compounds of the present invention were prepared by being dissolved in 100% DMSO. HDAC was prepared in a buffer at a certain concentration as an enzyme solution; trypsin and fluorescent group 4-amino-7-coumarin coupled-acetylated peptide (Ac-peptide) substrate were prepared in a buffer at a certain concentration as a substrate solution. The compounds were added into the reaction wells in a 384-well plate at a designed concentration of 10 µM, 1 µM, 0.5 µM, 0.1 µM, 0.05 µM, 0.01 µM, 0.005 µM, 0.001 µM, and 0.00005 µM, respectively, and then 15 µl of the HDAC solution was added into the reaction wells (15 µl of blank buffer to the control well). After incubation at room temperature for 15 minutes, 10 µl of the substrate solution was added to initiate the reaction, wherein the final concentration of HDAC1 protein was 6 nM, the final concentration of trypsin was 0.05 µM, and the final concentration of Ac-peptide was 8 µM. The 384-well plate was incubated at room temperature under dark condition. After incubation for 1 hour, the fluorescence intensity was measured by a microplate reader (the emission wavelength was 355 nm and the absorption wavelength was 460 nm). The results were analyzed by GraphPad Prism software and IC50 values were calculated according to the formula:

$$Y = \text{Background Data} + (\text{Top Data} - \text{Background Data}) / (1 + 10^{((\text{Log IC50} - X) \text{ a curve slope})}),$$

where Y: the inhibition rate (%) and X: the concentration of the compound.

2. Determination of Cell Proliferative Activity

Tumor cell line A375: human melanoma cell; H460: lung adenocarcinoma cell; Hela: human cervical cancer cell; HepG2: human liver cancer cell; and SKOV-3: human ovarian cancer cell, were all purchased from ATCC and cultured to logarithmic phase according to the cultivation protocol recommended by ATCC. The cells in the logarithmic phase were plated onto a 96-well plate at 2000-3000 cells/well; in the case of adherent cells, the cells should be adherent to the wall. The compounds were then added into the experiment wells at a designed concentration and incubated for 96 hours. After that, the cell proliferative activity was determined by MTT assay for the tumor cells representing the solid tumor model and by cck-8 assay for the tumor cells representing the hematologic tumor model. The results were analyzed by Graph Pad Prism software and the $IC_{50}$ values were calculataed according to the formula:

$$Y = \text{Background Data} + (\text{Top Data} - \text{Background Data}) / (1 + 10^{((\text{Log IC50} - X) \text{ a curve slope})}),$$

where Y is the inhibition rate (%) and X is the concentration of the compound.

TABLE 1

In vitro anti-proliferation activity of the preferred compounds against tumor cells

| Compound | Human melanoma A375 | Human lung cancer cell H460 | Human cervical cancer cell Hela | Human liver cancer cell HepG2 | Human ovarian cancer cell SKOV-3 |
|---|---|---|---|---|---|
| | | | Half-Inhibitory Concentration $IC_{50}$ | | |
| II-1 | a | b | b | b | b |
| II-2 | b | b | b | c | c |
| II-3 | a | b | a | a | b |
| II-4 | a | a | a | a | b |
| II-5 | a | a | a | a | a |
| II-6 | b | b | b | b | b |
| II-7 | b | b | b | b | b |
| II-13 | b | b | b | b | b |
| II-14 | a | a | a | a | a |
| II-15 | b | a | a | a | a |
| II-16 | a | a | a | a | a |
| II-18 | b | b | b | b | b |
| II-24 | a | a | a | a | a |
| III-1 | c | d | d | d | d |
| III-2 | c | c | c | c | c |
| III-3 | b | b | b | b | b |
| III-4 | b | b | b | b | b |
| III-12 | a | b | b | b | b |
| III-13 | b | b | b | c | c |
| III-14 | b | b | c | c | c |
| III-15 | a | b | b | b | b |
| IV-1 | b | b | b | b | b |
| IV-2 | b | b | a | b | b |
| IV-3 | c | c | b | c | b |
| IV-4 | b | a | b | b | a |
| SAHA ($IC_{50}$) μM | a | a | a | a | a | a: $IC_{50} > 1$ μM;
b: $0.1$ μM $< IC_{50} < 1$ μM;
c: $0.01$ μM $< IC_{50} < 0.1$ μM;
d: $IC_{50} < 0.01$ μM.

3. Determination of Half-inhibitory Activity of Some of the Compounds Against HDAC1, HDAC6 and HDAC8

TABLE 2

$IC_{50}$ of some of the compounds against HDACs 1, 6 and 8

| Compound | HDAC1 | HDAC6 | HDAC8 |
|---|---|---|---|
| | | $IC_{50}$ | |
| II-1 | b | d | a |
| II-2 | c | b | a |
| II-3 | b | c | a |
| II-4 | b | c | a |
| II-5 | b | d | a |
| II-6 | b | c | a |
| II-7 | b | d | a |
| II-13 | c | c | a |
| II-14 | b | c | a |
| II-15 | b | c | a |
| II-16 | b | d | a |
| II-18 | b | c | a |
| II-24 | a | b | a |
| III-1 | a | a | a |
| III-2 | b | c | a |
| III-3 | b | b | a |
| III-4 | b | c | a |
| III-12 | b | c | a |
| III-13 | b | b | a |
| III-14 | b | b | a |
| III-15 | c | c | a |
| IV-1 | a | a | a |
| IV-2 | a | a | a |
| IV-3 | a | a | a |
| IV-4 | c | c | a |
| SAHA | c | c | b | a: $IC_{50} > 1$ μM;
b: $0.1$ μM $< IC_{50} < 1$ μM;
c: $0.01$ μM $< IC_{50} < 0.1$ μM;
d: $IC_{50} < 0.01$ μM.

4. Selectivity of Some of the Compounds Against Histone Deacetylase Isoforms

TABLE 3

Activity and selectivity of some of the compounds against HDAC1, HDAC6 and HDAC8

| Compound | HDAC1 | HDAC6 | HDAC8 | HDAC1/6 | HDAC8/6 |
|---|---|---|---|---|---|
| | | $IC_{50}$ (nM) | | Selection Ratio | |
| II-4 | 272 | 34 | 1510 | 8.0 | 44.4 |
| II-2 | 84 | 196 | 1465 | 0.4 | 7.5 |
| II-1 | 172 | 8.6 | 1181 | 20.0 | 137.3 |
| II-3 | 451 | 57 | 1698 | 7.9 | 29.8 |
| II-5 | 44.5 | 6.4 | 2376 | 6.9 | 371.3 |
| II-6 | 552 | 72 | 4933 | 7.7 | 68.5 |
| II-7 | 638 | 5.8 | 1265 | 110.0 | 218.1 |
| II-13 | 76 | 34 | 2457 | 2.2 | 72.3 |
| II-14 | 203 | 49 | 1326 | 4.1 | 27.1 |
| II-15 | 176 | 19 | 1058 | 9.3 | 55.7 |
| II-16 | 385 | 10 | 1676 | 38.5 | 167.6 |
| II-18 | 437 | 15 | 2916 | 29.1 | 194.4 |

5. Therapeutic Effect of the Compounds II-2 and III-2 on the MV4-11 Chronic MMelomonocytic Leukemia Model Female NOD/SCID mice weighing 18-20 g were adopted in the experiment and were subcutaneously inoculated with $5.0 \times 10^5$ MV4-11 cells. 24 mice were inoculated in total and randomly divided into 4 groups: the compound II-2 group, the compound II-2 group and the SAHA group (positive drug group) (setting a dose of 50 mg/kg), as well as the physiological saline group as a negative control group. At Day 10 after inoculation of the tumor cells, the drugs were intravenously administered to the mice once every other day, continuously for a total of 12 times. After drug withdrawal, the mice were weighed and the tumor volume, formation rate and tumor weight of the mice were also observed. The results were shown in FIG. 1 and suggested that, compared with the blank control group, the compound III-2 significantly inhibited tumor growth in the tumor-bearing nude mice (P<0.01), and the activity of the compound III-2 was superior to that of the positive control group SAHA. The tumor weight of the treatment groups was significantly lower than that of the control group.

Figure 2:
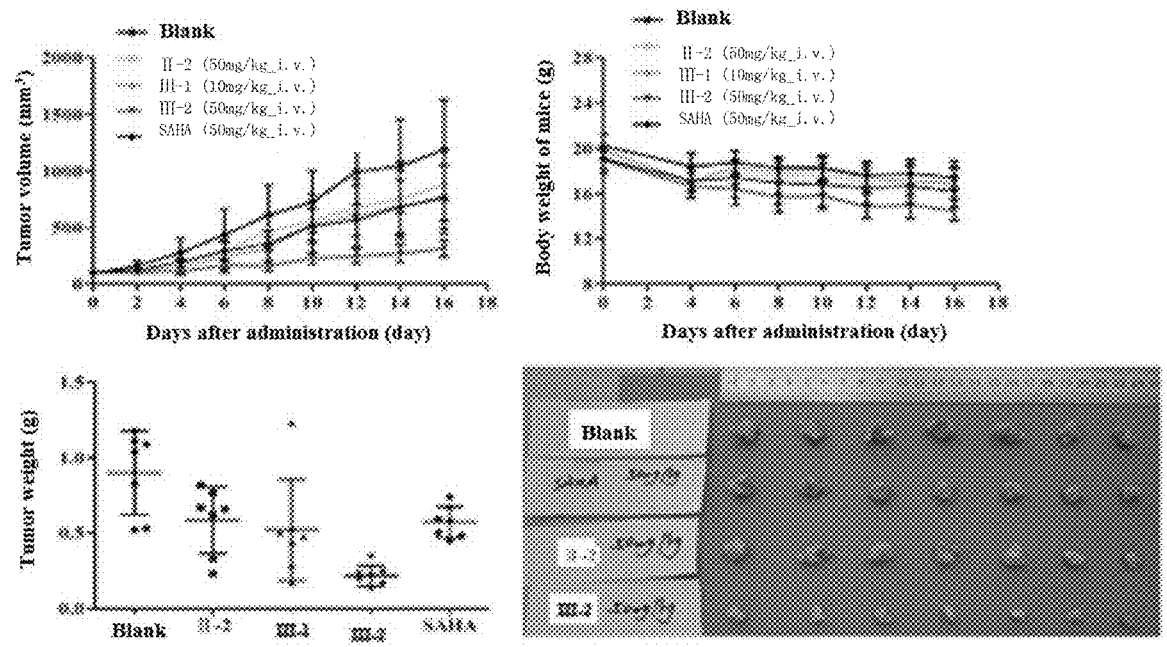
FIG. 2 depicts the therapeutic effect of the compound (II-2), the compound (III-1) and the compound (III-2) according to the present invention on the HCT116 colon cancer model.

6. Therapeutic Effect of the Compounds II-2, III-1 and III-2 on the Colon Cancer HCT116 Model Female nude mice weighing 18-20 g were adopted in the experiment and were subcutaneously inoculated with $5.0 \times 10^5$ HCT116 cells. 28 mice were inoculated in total and randomly divided into 4 groups: the compound II-2 group, the compound III-2 group and the SAHA group (setting a dose of 50 mg/kg), the compound III-1(setting a dose of 10 mg/kg), as well as the physiological saline group as a negative control group. At Day 10 after inoculation of the tumor cells, the compounds II-2, III-1 and III-2 were intravenously administered to the mice, and SAHA was intraperitoneally administered. Administration was conducted once every other day, continuously for a total of 9 times. After drug withdrawal, the mice were weighed and the tumor volume, formation rate and tumor weight of the mice were also observed. The results were shown in FIG. 2.

The experiment results suggested that, compared with the blank control group, the compounds II-2, III-1 and III-2 significantly prolonged the survival time of mice (P<0.01), and the effect of the compounds II-2, III-1 and III-2 prolonging the survival time of mice was superior to that of the positive control group. The tumor weight of the treatment groups was significantly lower than that of the control group.

7. Western Blot Assay for Detecting the Level of Acetylated Proteins with the Preferred Compound III-2

The compounds or the positive control compound were added into each group of cells already adherent to the walls ($2\times10^6$ HCT116 cells or $5\times10^6$ MV4-11 cells) at a designed concentration. After treatment for 4 hours, trypsin was added for digestion, followed by collecting the cells. After washing with cold PBS twice, the cells were lysed by adding RIPA lysis solution (which was purchased from Beyotime, Art. No.: P0013B, adding 1 mM PMSF before use), allowing for lysis on ice for 30 minutes while vortexing at intervals. The lysate was subjected to ultrasonic treatment on an ice bath (ultrasonicated for 3 seconds and repeated 5 times for each group at an interval of 10 seconds). The supernatant was collected by centrifugation at 12,000 g for 20 min at 4° C. and then mixed the SDS-PAGE loading buffer (purchased from Beyotime, Art. No.: P0015F). The mixture was heated in boiling water for 5 minutes to obtain a protein sample. The protein concentration of the sample was quantified by BCA method. 20 μg total protein from each group was subjected to 15% SDS-PAGE electrophoresis, and 5μl of a pre-stained protein marker (purchased from Thermo, Art. No.: 26616) was loaded to an additional selective lane in order to compare protein molecular weights as well as to detect the transmembrane result. When the bromophenol blue bands ran close to the bottom of the gel, the electrophoresis was terminated and the proteins on the gel were transferred to a PVDF membrane at a pore size of 0.22 μm. After 1.5 hours of transmembrane at a constant current of 200 mA, the PVDF membrane was removed and blocked in 5% skimmed milk for 1 hour. After completion of blocking, the membrane was incubated with the primary antibody (Ac-H3 antibody was purchased from Santa Cruz, Art. No.: sc-56616; Ac-α-tubulin antibody was purchased from Santa Cruz, Art. No.: sc-23950) overnight at 4° C. and then washed with TBS/T for 10 minutes for 3 times. The membrane was incubated with the horseradish peroxidase-coupled secondary antibody at room temperature for 1 hour, and then washed with TBS/T for 10 minutes for 3 times. After washing with TBS for 5 minutes, the membrane was exposed and developed by using a film in the darkroom. The detected GAPDH protein was an internal reference protein (GAPDH antibody was purchased from ZSGB-Bio, Art. No.: TA-08).

Figure 3:
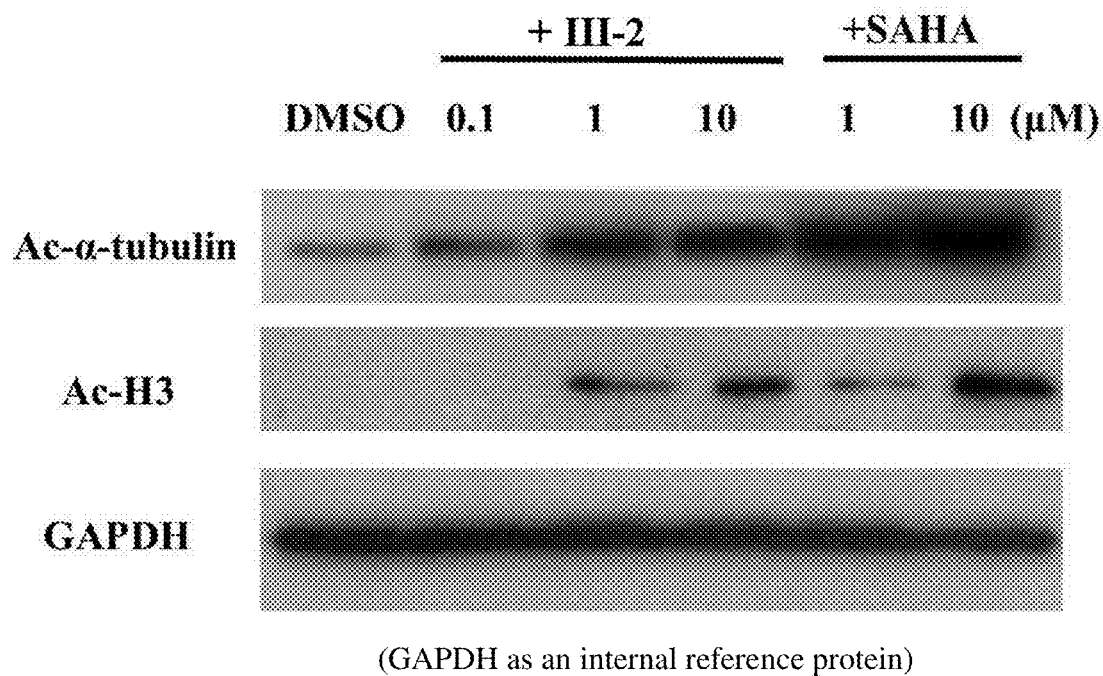
FIG. 3 depicts the changes of the acetylation level of HDAC substrate, as measured by Western assay, after treatment of colon cancer HCT116 cells with the compound (III-2) according to the present invention or the positive control SAHA for 16 hours.
Figure 4:
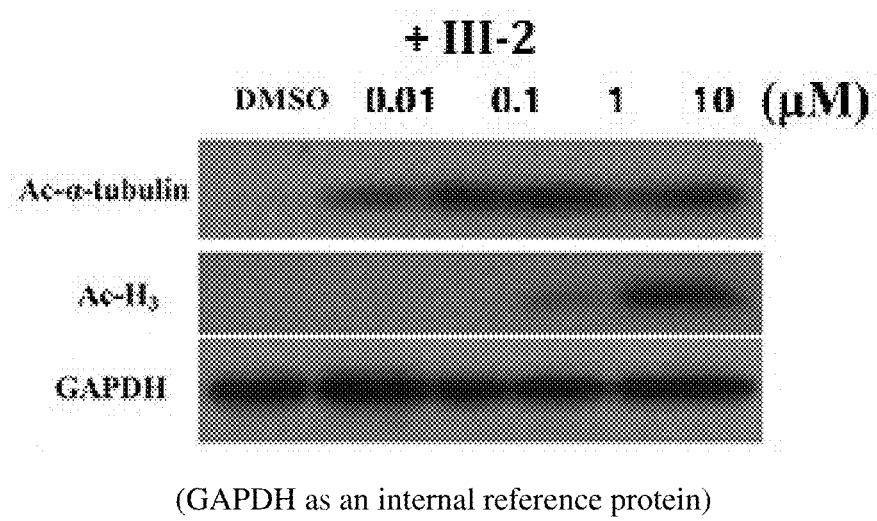
FIG. 4 depicts the changes of the acetylation level of HDAC substrate, as measured by Western assay, after treatment of chronic leukemia NV4-11 cells with the compound (III-2) according to the present invention for 16 hours.

It can be seen from FIGS. 3 and 4 that the positive drug SAHA was a broad-spectrum HDACi inhibitor and could up-regulate acetylation of tubulin and H3, while the compound III-2 was a selective inhibitor of HDAC6. In addition, HDAC6 was a protease associated with α-tubulin deacetylation. Thus it was verified by western blot that the compound III-2 inhibited α-tubulin deacetylation. It was found that the compound III-2 could up-regulate the acetylated α-tubulin protease in a dose-dependent manner. The deacetylation of Ac-H3 by the compound III-2 was also demonstrated.

8. Study on the Activity of the Preferred Compound III-2 Against Various HDAC Isoforms

TABLE 4

Comparison of activity of the preferred compound III-2 against various HDAC isoforms with that of the positive controls ACY-1215, LBH-589 and SAHA

| Classes of HDACs | Isoforms | IC$_{50}$ (nM) | | | |
|---|---|---|---|---|---|
| | | III-2 | ACY-1215 | LBH-589 | SAHA |
| Class I | HDAC1 | 422 ± 1 | 38 ± 5 | 1 ± 0.1 | 11 ± 1 |
| | HDAC2 | 386 ± 7 | 95 ± 9 | 3 ± 0.05 | 35 ± 11 |
| | HDAC3 | 439 ± 9 | 135 ± 27 | 2 ± 0.1 | 30 ± 5 |
| | HDAC8 | 3398 ± 487 | 254 ± 57 | 5 ± 0.4 | 172 ± 45 |
| Class IIa | HDAC4 | >10000 | >10000 | 338 ± 17 | >10000 |
| | HDAC5 | >10000 | >10000 | 190 ± 35 | >10000 |
| | HDAC7 | >10000 | >10000 | 4354 ± 267 | >10000 |
| | HDAC9 | >10000 | >10000 | 888 ± 26 | >10000 |
| Class IIb | HDAC6 | 17 ± 2 | 9 ± 2 | 4 ± 0.2 | 15 ± 3 |
| | HDAC10 | 1176 ± 168 | 194 ± 54 | 4 ± 1 | 170 ± 10 |
| Class IV | HDAC11 | >10000 | >10000 | 4112 ± 84 | >10000 |

9. Study on the Anti-proliferative Activity of the Preferred Compound III-2 Against Various Tumor Cell Strains

TABLE 5

Comparison of the anti-proliferative activity of the preferred compound III-2 against various tumor cell strains with that of the positive controls ACY-1215 and SAHA

| Types of Tumors | Cell Strains | Half-Inhibitory Concentration IC$_{50}$ (nM) | | |
|---|---|---|---|---|
| | | III-2 | ACY-1215 | SAHA |
| Multiple myeloma | U266 | 14 ± 6 | >5000 | 581 ± 96 |
| | RPMI8226 | 15 ± 4 | 1468 ± 310 | 423 ± 54 |
| Leukemia | MV4-11 | 60 ± 32 | >5000 | 85 ± 19 |
| | K562 | 63 ± 18 | >5000 | 444 ± 43 |
| B-cell lymphoma | Ramos | 71 ± 31 | >5000 | >1000 |
| Ovarian cancer | A2780s | 46 ± 11 | >5000 | >1000 |
| | SKOV-3 | 50 ± 8 | >5000 | >1000 |
| Breast cancer | SKBR3 | 22 ± 8 | >5000 | >1000 |
| Liver cancer | HepG2 | 41 ± 1 | >5000 | >1000 |
| Lung cancer | H460 | 55 ± 13 | >5000 | >1000 |
| | A549 | 104 ± 29 | >5000 | >1000 |
| Cervical cancer | Hela | 49 ± 20 | >5000 | 711 ± 245 |
| Colon cancer | HCT116 | 35 ± 21 | >5000 | >1000 |
| | HT29 | 72 ± 37 | >5000 | >1000 |

10. Assay on the Bioavailability of the Preferred Compound III-2

SD rats were orally administered or intravenously injected with the compound and the blood samples were collected at 0.25, 0.5, 1, 2, 4, 8 and 24 h. Plasma was separated by centrifugation and added into EDTA-containing medium. Intravenous administration: 8 mg/kg of the compound, dissolved in 2% DMA (dimethylamine), 15% polyethylene glycol 400, 77% carboxymethyl-β-cyclodextrin, adjusted to pH=7. Oral administration: 40 mg/kg of the compound suspension, dissolved in 2% high-substituted hydroxypropyl cellulose, 0.1% Tween 80. The compound in plasma was determined by LC-MS/MS.

TABLE 6

Bioavailability of the preferred compound III-2 in SD rats

| | III-2 | |
|---|---|---|
| | Intravenous administration | Oral administration |
| Number of animals | 6 | 6 |
| Administration dose (mg/kg) | 12 | 12 |
| Clearance rate (L/h/kg) | 7.008 | 12.877 |
| Distribution volume (L/kg) | 61.263 | 154.811 |
| Area under the curve (μg/L · h) | 2434.117 | 1242.234 |
| Maximum plasma concentration (μg/L) | 2213.217 | 238.133 |
| Half-life (h) | 7.658 | 9.62 |
| Bioavailability (%) | | 47.0 |

Figure 5:
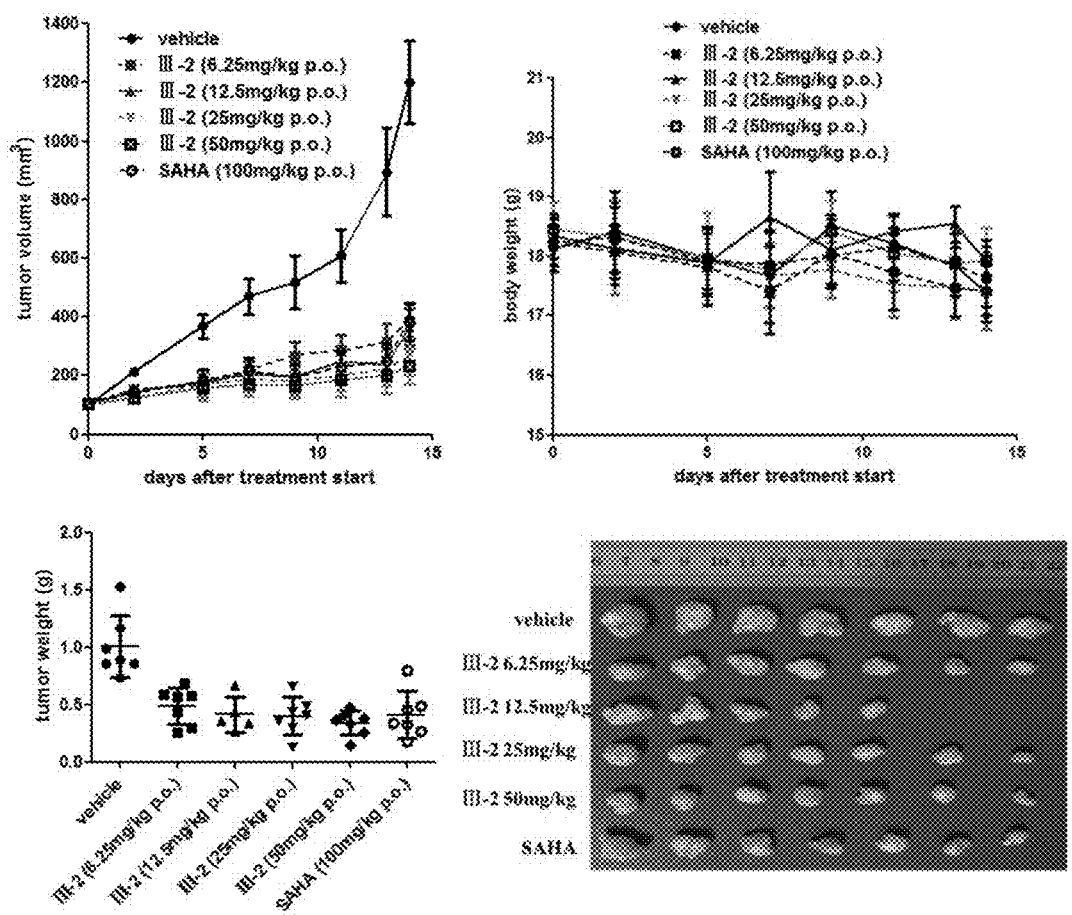
FIG. 5 depicts the therapeutic effect of the compound III-2 according to the present invention on the colon cancer HCT116 model.

11. Therapeutic Effect of the Preferred Compound III-2 on the Colon Cancer HCT116 Model Female nude mice weighing 18-20 g were adopted in the experiment and were subcutaneously inoculated with $5.0 \times 10^6$ HCT116 cells. 42 mice were inoculated in total and randomly divided into 6 groups: the preferred compound III-2 groups (setting a four-dose gradient of 6.25 mg/kg, 12.5 mg/kg, 25 mg/kg and 50 mg/kg), the control drug SAHA group (setting a dose of 100 mg/kg) and the physiological saline group as a solvent control group. At Day 10 after inoculation of the tumor cells, the compound III-2 and SAHA were intragastrically administered once every other day, continuously for a total of 8 times (during the course of the experiment, there were two experimental animals died accidentally in the III-2 12.5 mg/kg dose group). After drug withdrawal, the mice were weighed and the tumor volume, formation rate and tumor weight of the mice were also observed. The results were shown in FIG. 5.

The experiment results suggested that, compared with the solvent group, the tumor inhibitory rate of the compound III-2 at the doses of 6.25, 12.5, 25 and 50 mg/kg was 51.28%, 58.64%, 60.37% and 66.05%, respectively; the tumor inhibitory rate of the control drug SAHA group was 59.23%. Thus, the compound III-2 had a significant effect on inhibiting the growth of the colon cancer HCT116 subcutaneous tumor model, and the effect was superior to the control drug SAHA.

Figure 6:
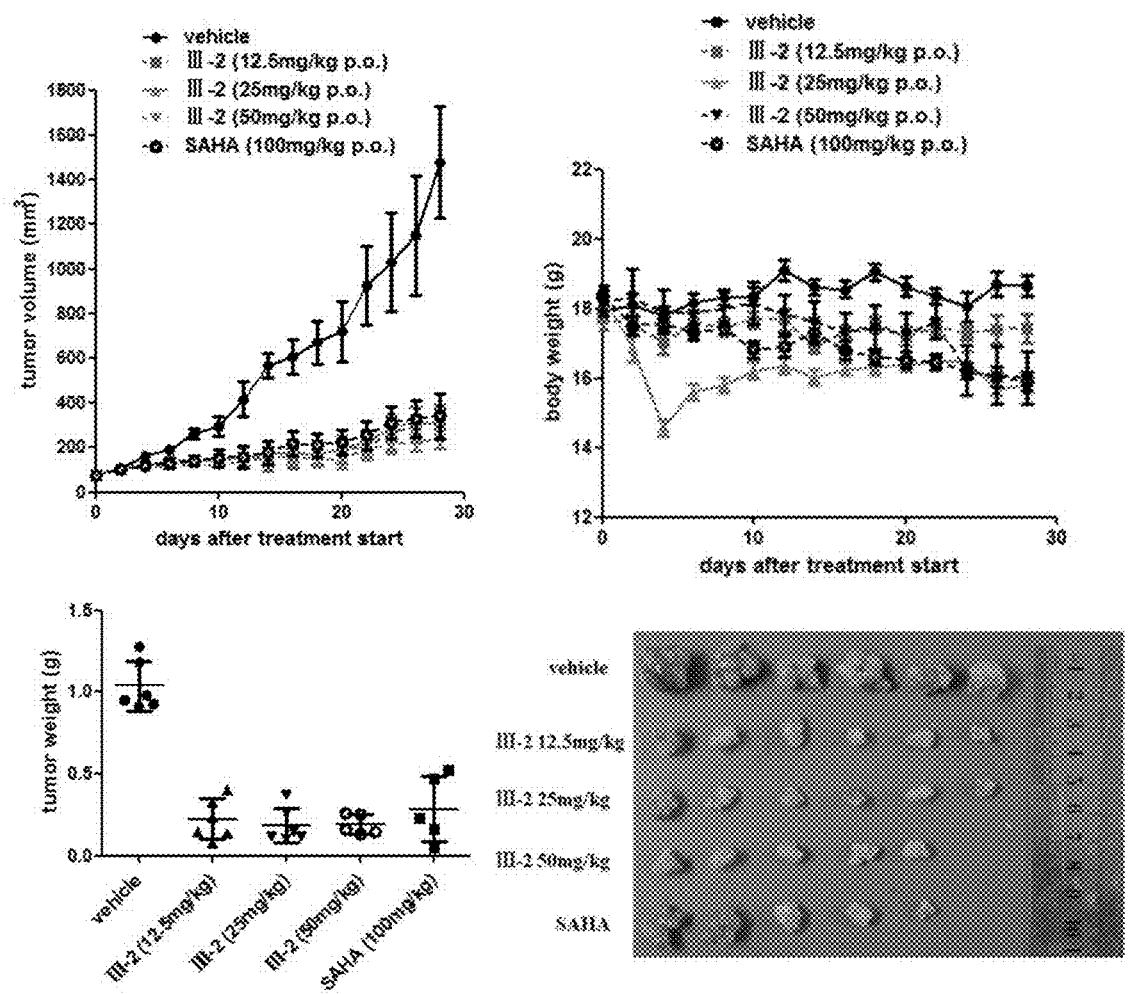
FIG. 6 depicts the therapeutic effect of the compound III-2 according to the present invention on the ovarian cancer A2780s model.

12. Therapeutic Effect of the Preferred Compound III-2 on the Ovarian Cancer A2780s Model Female nude mice weighing 16-20 g were adopted in the experiment and were subcutaneously inoculated with $5.0 \times 10^6$ A2780s cells. 30 mice were inoculated in total and randomly divided into 5 groups: the preferred compound III-2 groups (setting a three-dose gradient of 12.5 mg/kg, 25 mg/kg and 50 mg/kg), the control drug SAHA group (setting a dose of 100 mg/kg), and the physiological saline group as a solvent control group. At Day 12 after inoculation of the tumor cells, the compound III-2 and SAHA were intragastrically administered once every other day, continuously for a total of 16 times. After drug withdrawal, the mice were weighed (in either of the III-2 50 mg/kg group and the SAHA group, there was one mouse died), and the tumor volume, formation rate and tumor weight of the mice were also observed. The results were shown in FIG. 6.

The experiment results suggested that, compared with the solvent group, the tumor inhibitory rate of the compound III-2 at the doses of 12.5, 25 and 50 mg/kg was 78.49%, 82.02% and 81.70%, respectively; the tumor inhibitory rate of the control drug SAHA group was 72.46%. Thus, the compound III-2 had a significant effect on inhibiting the growth of the ovarian cancer A2780s subcutaneous tumor model, and the effect was superior to the control drug SAHA.

Figure 7:
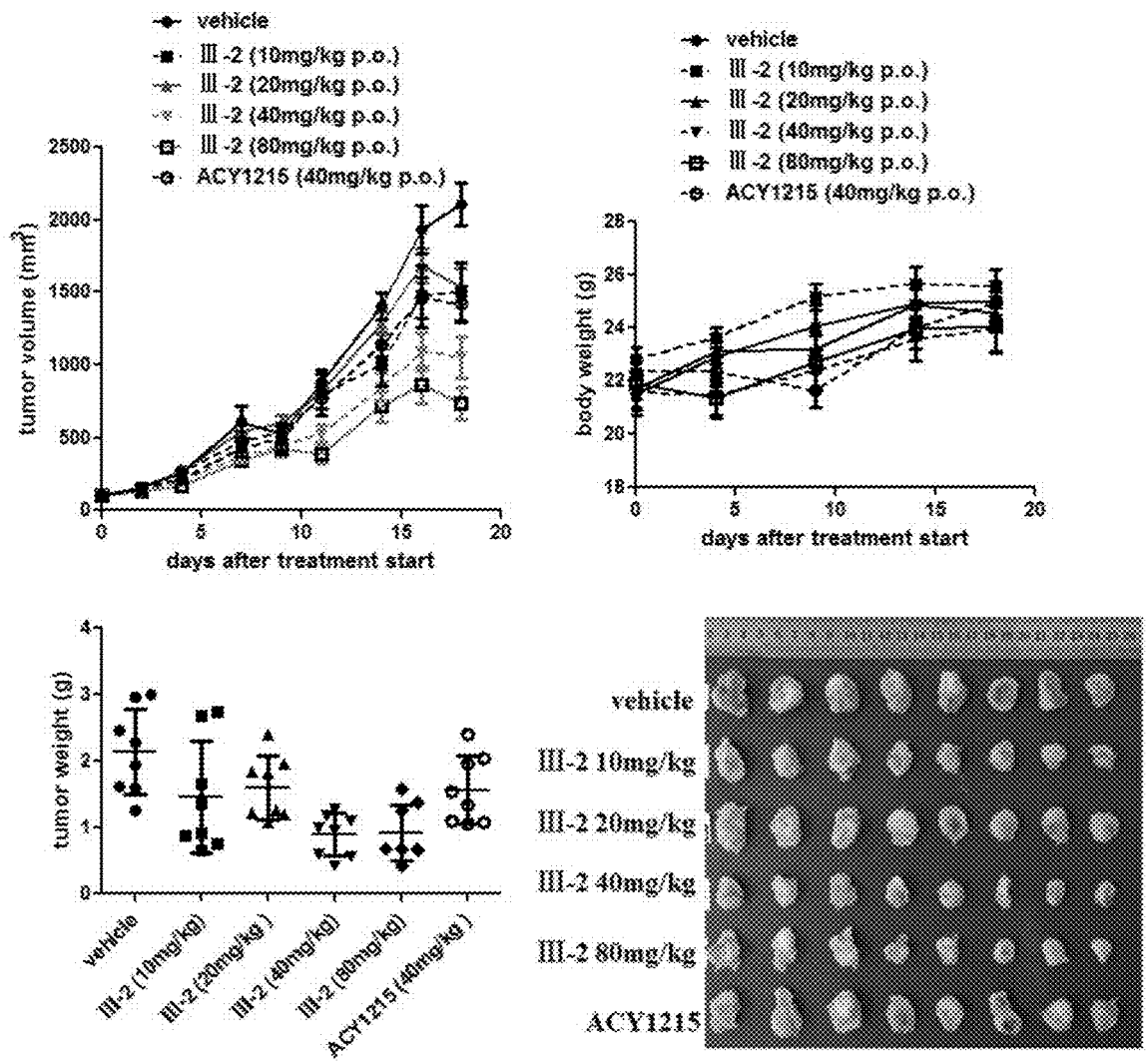
FIG. 7 depicts the therapeutic effect of the compound III-2 according to the present invention on the B-cell lymphoma HBL-1 model.

13. Therapeutic Effect of the Preferred Compound III-2 on the B-cell Lymphoma HBL-1 Model Female NOD/SCID mice weighing 20-25 g were adopted in the experiment and were subcutaneously inoculated with $1 \times 10^7$ HBL-1 cells. 48 mice were inoculated in total and randomly divided into 6 groups: the preferred compound III-2 groups (setting a four-dose gradient of 10 mg/kg, 20 mg/kg, 40 mg/kg and 80 mg/kg), the HDAC6 selective inhibitor ACY1215 group as a control drug group (at a dose of 40 mg/kg), and the physiological saline group as a solvent control group. At Day 14 after inoculation of the tumor cells, the compound III-2 and ACY1215 were intragastrically administered once every other day, continuously for a total of 9 times. After drug withdrawal, the mice were weighed and the tumor volume, formation rate and tumor weight of the mice were also observed. The results were shown in FIG. 7.

The experiment results suggested that, compared with the solvent group, the tumor inhibitory rate of the compound III-2 at the doses of 10, 20, 40 and 80 mg/kg was 31.70%, 25.23%, 58.22% and 56.88%, respectively; the tumor inhibitory rate of the control drug ACY1215 group was 26.75%. Thus, the compound III-2 had a significant effect on inhibiting the growth of the B-cell lymphoma HBL-1 subcutaneous tumor model, and the effect was superior to the control drug ACY1215.

Figure 8:
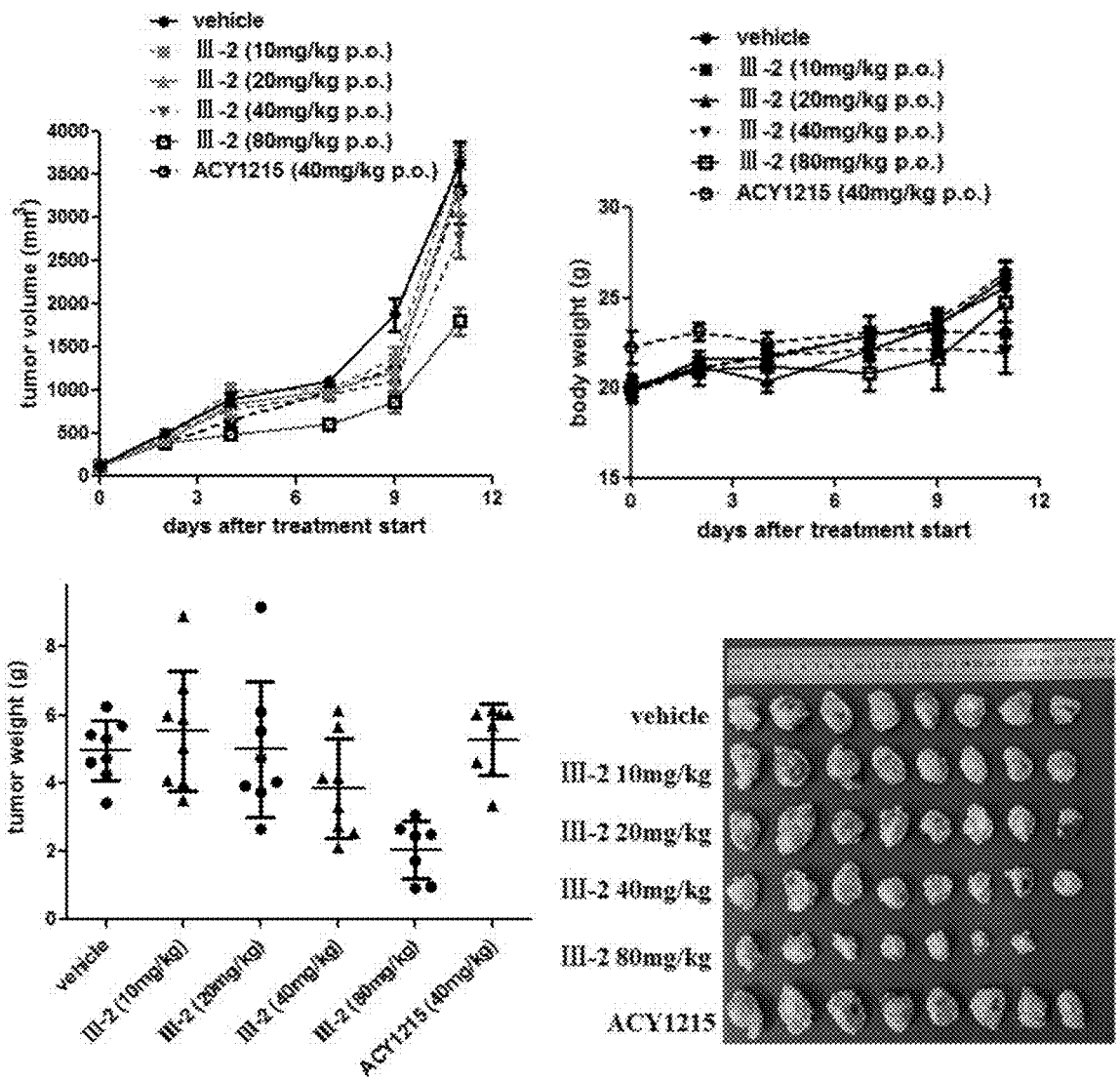
FIG. 8 depicts the therapeutic effect of the compound III-2 according to the present invention on the B-cell lymphoma Ramos model.

14. Therapeutic Effect of the Preferred Compound III-2 on the B-cell Lymphoma Ramos Model Female NOD/SCID mice weighing 20-24 g were adopted in the experiment and were subcutaneously inoculated with $1 \times 10^7$ Ramos cells. 48 mice were inoculated in total and randomly divided into 6 groups: the preferred compound III-2 groups (setting a four-dose gradient of 10 mg/kg, 20 mg/kg, 40 mg/kg and 80 mg/kg), the HDAC6 selective inhibitor ACY1215 as a control drug group (at a dose of 40 mg/kg), and the physiological saline group as a solvent control group. At Day 8 after inoculation of the tumor cells, the compound III-2 and ACY1215 were intragastrically administered, once every other day, continuously for a total of 6 times. After drug withdrawal, the mice were weighed (during the course of the experiment, there was a mouse died in the III-2 80 mg/kg dose group, indicating that this dose may exhibit toxicity to a few individuals), and the tumor volume, formation rate and tumor weight of the mice were also observed. The results were shown in FIG. 8.

The experiment results suggested that, compared with the solvent group, the compound III-2 at the two doses of 10 and 20 mg/kg had no effects on inhibiting tumor growth, while the tumor inhibitory rate of the compound III-2 at the doses of 40 and 80 mg/kg was 22.54% and 58.79%, respectively; there were no inhibitory effects of tumor growth in the control drug ACY1215 group. Thus, the compound III-2 at a dose of 80 mg/kg had a significant effect on inhibiting the growth of the B-cell lymphoma Ramos subcutaneous tumor model, and the effect was superior to the control drug ACY1215.

The invention claimed is:

1. A compound as shown in Formula I and pharmaceutically acceptable salts thereof:

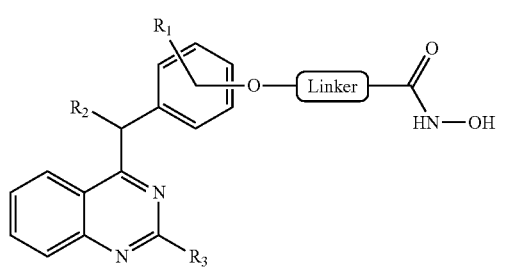

(I)

wherein, $R_1$, $R_2$ and $R_3$ are each independently hydrogen, halogen, $C_{1-10}$ alkyl, $R_4O$—, —$NH_2$, —$NO_2$, $R_4NH$—, wherein $R_4$ is $C_{1-10}$ alkyl or benzyl;

the Linker is a bond, —$(CH_2)_n$—, —$(CH_2)_nO$—, —$O(CH_2)_n$—, wherein n is an integer from 1 to 10; or is substituted phenyl, phenyl or six-membered heterocyclyl having 1 or 2 nitrogen atoms;

in said substituted phenyl, there are 1 to 4 substituents on the benzene ring, wherein the substituent of the substituted phenyl is halogen, —OH, —$NO_2$, cyano, alkoxy, $C_{1-4}$ alkyl or amino group;

the halogen is fluorine, chlorine, bromine or iodine;

in the above-mentioned groups, the $C_{1-10}$ alkyl is a linear, branched or cyclic saturated hydrocarbon containing 1-10 carbon atoms, wherein the alkyl is unsubstituted or is pyrrolidin-1-yl-$C_{2-10}$ alkyl, morpholin-1-yl-$C_{2-10}$ alkyl or piperazin-1-$C_{2-10}$ alkyl; and the pharmaceutically acceptable salts are hydrochloride, hydrobromide, sulfate, acetate, lactate, tartrate, tannate, citrate, trifluoroacetate, malate, maleate, succinate, p-toluenesulfonate or methanesulfonate.

2. The compound according to claim 1 or pharmaceutically acceptable salts thereof, wherein the compound is as shown in Formula II:

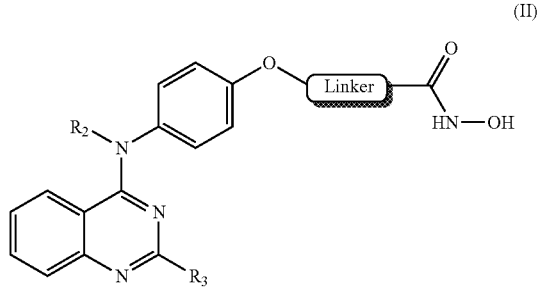

(II)

wherein, $R_2$ and $R_3$ are each independently hydrogen or $C_{1-4}$ alkyl;

the Linker is —$(CH_2)_n$—, wherein n is an integer from 1 to 5; or is —$(CH_2)_m$ phenyl-, wherein m is an integer from 0 to 5; or is six-membered heterocyclyl having 1 or 2 nitrogen atoms; and the pharmaceutically acceptable salts are hydrochloride, hydrobromide, sulfate, acetate, lactate, tartrate, tannate, citrate, trifluoroacetate, malate, maleate, succinate, p-toluenesulfonate or methanesulfonate.

3. The compound according to claim 1 or pharmaceutically acceptable salts thereof, wherein the $C_{1-10}$ alkyl is methyl, ethyl, propyl, isopropyl, cyclopropyl, butyl, isobutyl, sec-butyl, tert-butyl, cyclobutyl, pentyl, cyclopentyl, hexyl, cyclohexyl, heptyl, octyl, nonyl or decyl.

4. The compound according to claim 1 or pharmaceutically acceptable salts thereof, wherein the $R_4O$— is benzyloxy, pyrrolidin-1-yl-$C_{2-10}$ alkoxy, morpholin-1-yl-$C_{2-10}$ alkoxy or piperazin-1-$C_{2-10}$ alkoxy.

5. The compound according to claim 1 or pharmaceutically acceptable salts thereof, wherein the $R_4NH$— is aminoethyl, 1-aminopropyl, 2-aminopropyl, 1-aminobutyl, 2-aminobutyl, 1-aminopentyl, 1-aminohexyl, 1-aminoheptyl, 1-aminooctyl, 1-aminononyl, 1-aminodecyl, N-methylamino, N-ethylamino, N-propylamino, N-butylamino, N-pentylamino, N-hexylamino, N-heptylamino, N-octylamino, N-nonylamino or N-decylamino.

6. The compound or pharmaceutically acceptable salts thereof according to claim 1, wherein the compound is selected from:

(II-1) N-hydroxy-2-(4-(methyl(2-methyl-4-quinazolinyl)amino)phenoxy)acetamide;

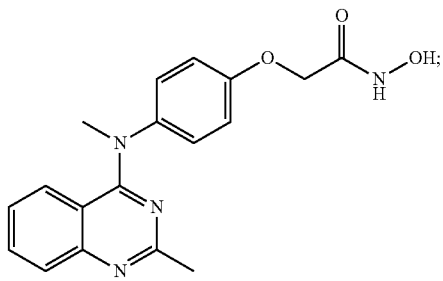 [SMILES: Cc1nc(N(C)c2ccc(OCC(=O)NO)cc2)c2ccccc2n1]

(II-2) N-hydroxy-4-(4-(methyl(2-methyl-4-quinazolinyl)amino)phenoxy)butanamide;

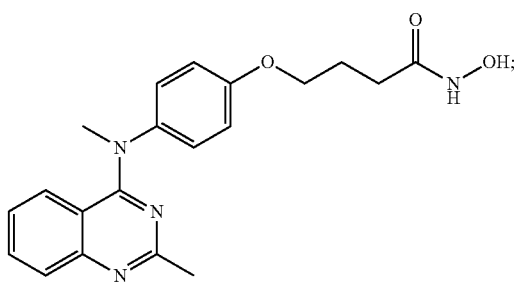 [SMILES: Cc1nc(N(C)c2ccc(OCCCC(=O)NO)cc2)c2ccccc2n1]

(II-3) N-hydroxy-5-(4-(methyl(2-methyl-4-quinazolinyl)amino)phenoxy)pentanamide;

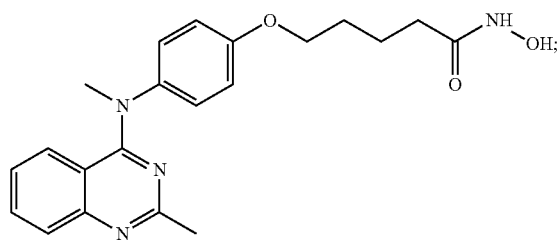 [SMILES: Cc1nc(N(C)c2ccc(OCCCCC(=O)NO)cc2)c2ccccc2n1]

(II-4) N-hydroxy-6-(4-(methyl(2-methyl-4-quinazolinyl)amino)phenoxy)hexanamide;

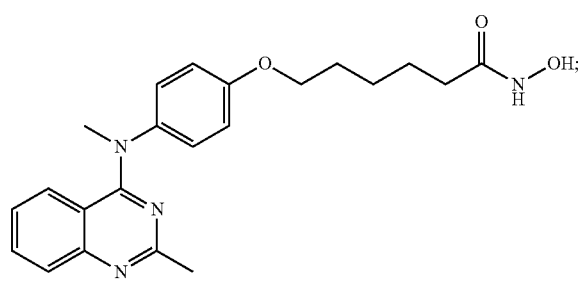 [SMILES: Cc1nc(N(C)c2ccc(OCCCCCC(=O)NO)cc2)c2ccccc2n1]

(II-5) N-hydroxy-4-((4-(methyl(2-methyl-4-quinazolinyl)amino)phenoxy)methyl)benzamide;

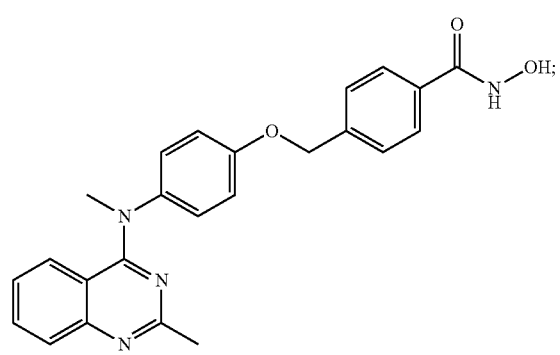 [SMILES: Cc1nc(N(C)c2ccc(OCc3ccc(C(=O)NO)cc3)cc2)c2ccccc2n1]

(II-6) N-hydroxy-4-(4-(methyl(2-methyl-4-quinazolinyl)amino)phenoxy)benzamide;

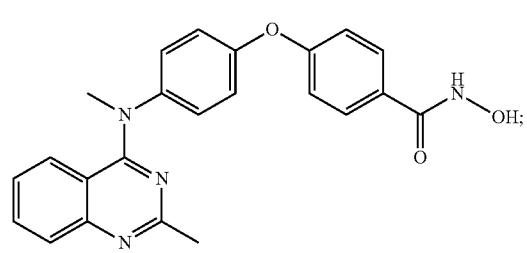 [SMILES: Cc1nc(N(C)c2ccc(Oc3ccc(C(=O)NO)cc3)cc2)c2ccccc2n1]

(II-7) N-hydroxy-6-(4-(methyl(2-methyl-4-quinazolinyl)amino)phenoxy)nicotinamide;

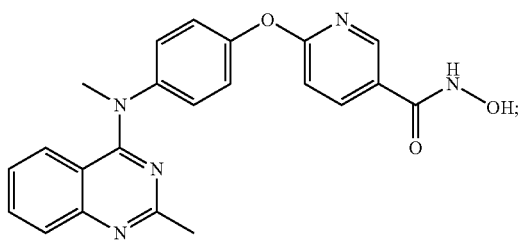 [SMILES: Cc1nc(N(C)c2ccc(Oc3ccc(C(=O)NO)cn3)cc2)c2ccccc2n1]

(II-8) N-hydroxy-5-(4-(methyl(2-methyl-4-quinazolinyl)amino)phenoxy)picolinamide;

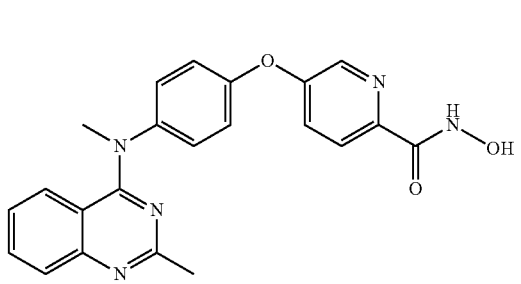

(II-9) N-hydroxy-2-(4-(methyl(2-methyl-4-quinazolinyl)amino)phenoxy)pyrimidin-5-amide;

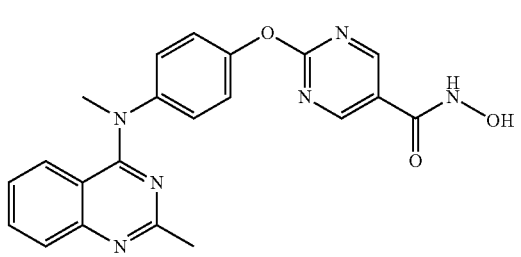 [SMILES: Cc1nc(N(C)c2ccc(Oc3ncc(C(=O)NO)cn3)cc2)c2ccccc2n1]

(II-10) N-hydroxy-5-(4-(methyl(2-methyl-4-quinazolinyl)amino)phenoxy)pyrimidin-2-amide;

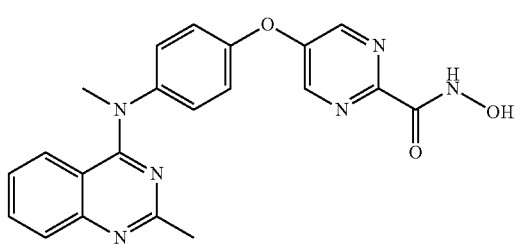 [SMILES: Cc1nc(N(C)c2ccc(Oc3cnc(C(=O)NO)nc3)cc2)c2ccccc2n1]

(II-11) N-hydroxy-5-(4-(methyl(2-methyl-4-quinazolinyl)amino)phenoxypyrazine-2-amide;

113 114

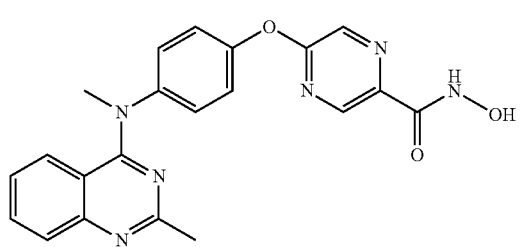

(II-12) N-hydroxy-2-(4-(methyl(4-quinazolinyl)amino)phenoxy)acetamide;

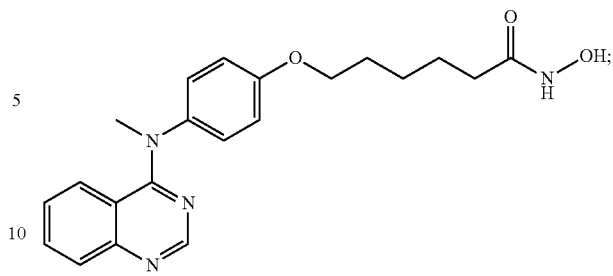

(II-16) N-hydroxy-4-((4-(methyl(4-quinazolinyl)amino)phenoxy)methyl)benzamide;

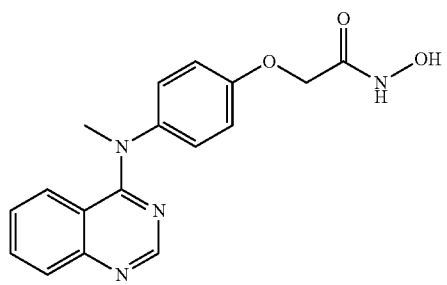 [SMILES: CN(c1ccc(OCC(=O)NO)cc1)c1ncnc2ccccc12]

(II-13) N-hydroxy-4-(4-(methyl(4-quinazolinyl)amino)phenoxy)butanamide;

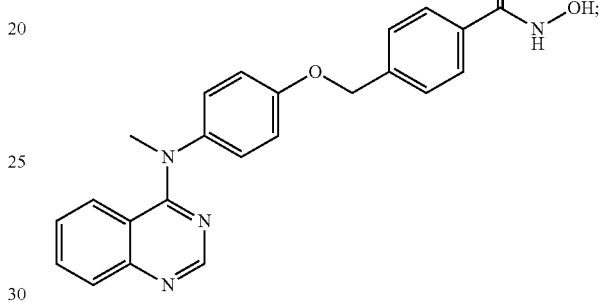

(II-17) N-hydroxy-4-(4-(methyl(4-quinazolinyl)amino)phenoxy)benzamide;

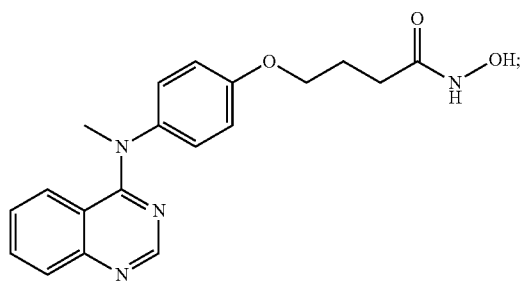 [SMILES: CN(c1ccc(OCCCC(=O)NO)cc1)c1ncnc2ccccc12]

(II-14) N-hydroxy-5-(4-(methyl(4-quinazolinyl)amino)phenoxy)pentanamide;

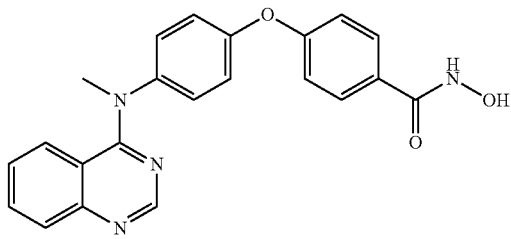

(II-18) N-hydroxy-6-(4-(methyl(4-quinazolinyl)amino)phenoxy)nicotinamide;

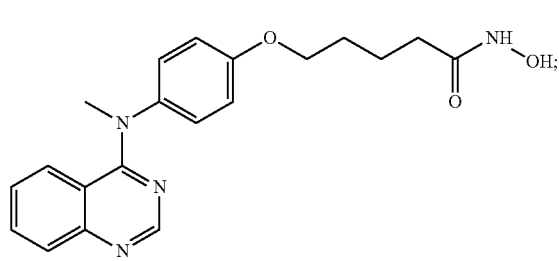 [SMILES: CN(c1ccc(OCCCCC(=O)NO)cc1)c1ncnc2ccccc12]

(II-15) N-hydroxy-6-(4-(methyl(4-quinazolinyl)amino)phenoxy)hexanamide;

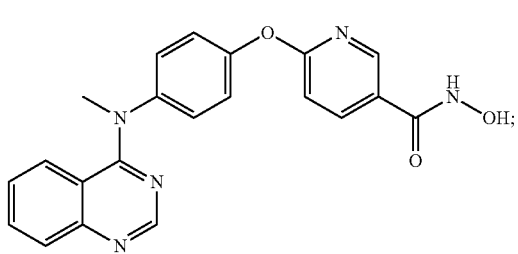 [SMILES: CN(c1ccc(Oc2ccc(C(=O)NO)cn2)cc1)c1ncnc2ccccc12]

(II-19) N-hydroxy-5-(4-(methyl(4-quinazolinyl)amino)phenoxypicolinamide;

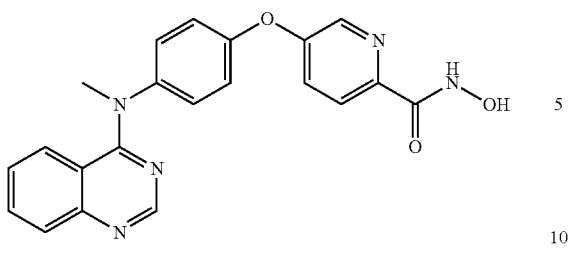

(II-20) N-hydroxy-2-(4-(methyl(4-quinazolinyl)amino)phenoxy)pyrimidin-5-formamide;

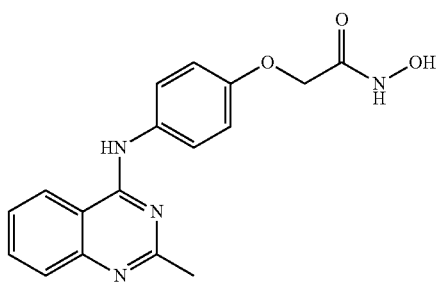

(II-24) N-hydroxy-3-(4-((2-methyl-4-quinazolinyl)amino)phenoxy)propionamide;

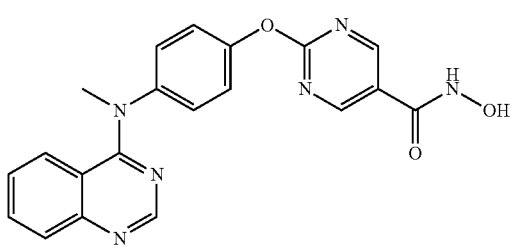

(II-21) N-hydroxy-5-(4-(methyl(4-quinazolinyl)amino)phenoxy)pyrimidin-2-formamide;

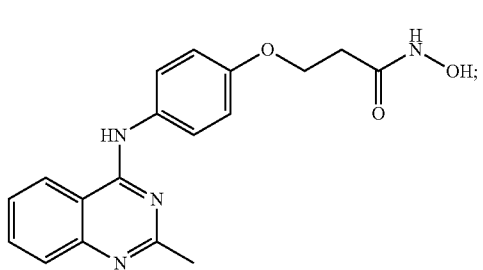 [SMILES: Cc1nc(Nc2ccc(OCCC(=O)NO)cc2)c2ccccc2n1]

(II-25) N-hydroxy-4-(4-((2-methyl-4-quinazolinyl)amino)phenoxy)butanamide;

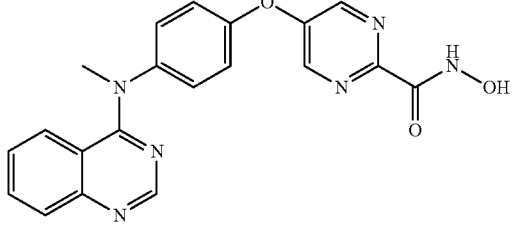

(II-22) N-hydroxy-5-(4-(methyl(4-quinazolinyl)amino)phenoxy)pyrazin-2-formamide;

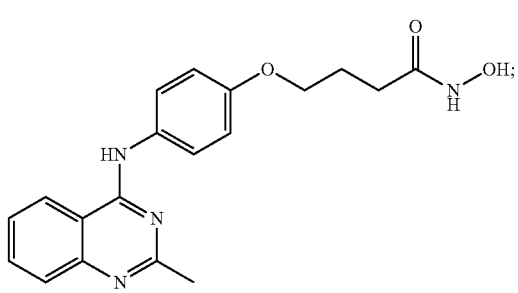

(II-26) N-hydroxy-5-(4-((2-methyl-4-quinazolinyl)amino)phenoxy)pentanamide;

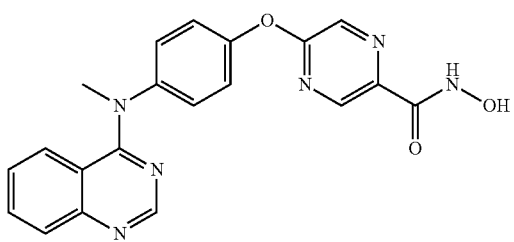

(II-23) N-hydroxy-2-(4-((2-methyl-4-quinazolinyl)amino)phenoxy)acetamide;

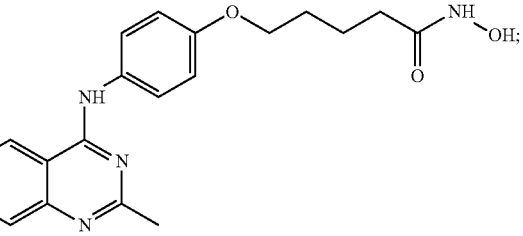

and (II-27) N-hydroxy-6-(4-((2-methyl-4-quinazolinyl)amino)phenoxy)hexanamide;

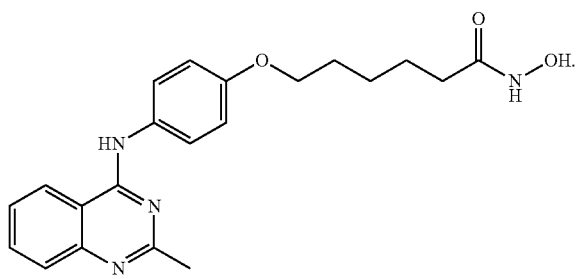 [SMILES: Cc1nc(Nc2ccc(OCCCCCC(=O)NO)cc2)c2ccccc2n1]

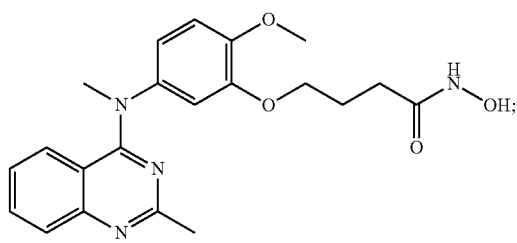

7. The compound or pharmaceutically acceptable salts thereof according to claim 1, wherein the compound is as shown in Formula III:

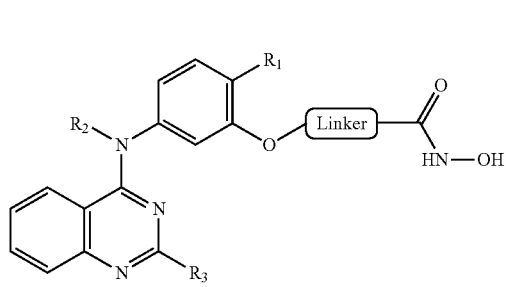

(III)

wherein,
  $R_1$ is hydrogen or $C_{1-4}$ alkoxy; $R_2$ and $R_3$ are independently hydrogen or $C_{1-4}$ alkyl;
  the Linker is a bond, —(CH$_2$)$_n$—, —(CH$_2$)$_n$O—, —O(CH$_2$)$_n$—, wherein n is an integer from 1 to 10; or is substituted phenyl, phenyl or six-membered heterocyclyl having 1 or 2 nitrogen atoms;
  in the substituted phenyl, there are 1 to 4 substituents on the benzene ring, wherein the substituent of the substituted phenyl is halogen, —OH, —NO$_2$, cyano, alkoxy, $C_{1-4}$ alkyl or amino group;
  the halogen is fluorine, chlorine, bromine or iodine; and
  the pharmaceutically acceptable salts are hydrochloride, hydrobromide, sulfate, acetate, lactate, tartrate, tannate, citrate, trifluoroacetate, malate, maleate, succinate, p-toluenesulfonate or methanesulfonate.

8. The compound or pharmaceutically acceptable salts thereof according to claim 1, wherein the compound is selected from:
  (III-1) N-hydroxy-2-(2-methoxy-5-(methyl(2-methyl-4-quinazolinyl)amino)phenoxy)acetamide;

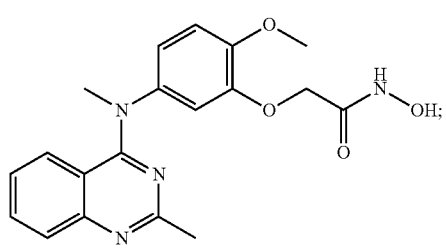 [SMILES: COc1ccc(N(C)c2nc(C)nc3ccccc23)cc1OCC(=O)NO]

(III-2) N-hydroxy-4-(2-methoxy-5-(methyl(2-methyl-4-quinazolinyl)amino)phenoxy)butanamide;

(III-3) N-hydroxy-5-(2-methoxy-5-(methyl(2-methyl-4-quinazolinyl)amino)phenoxy)pentanamide;

(III-4) N-hydroxy-6-(2-methoxy-5-(methyl(2-methyl-4-quinazolinyl)amino)phenoxy)hexanamide;

(III-5) N-hydroxy-4-((2-methoxy-5-(methyl(2-methyl-4-quinazolinyl)amino)phenoxy)methyl) benzamide;

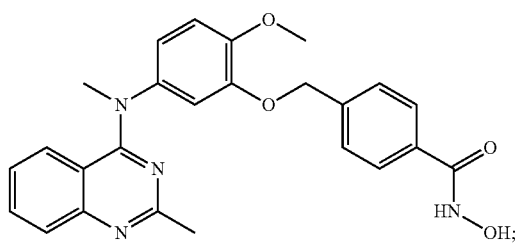 [SMILES: COc1ccc(N(C)c2nc(C)nc3ccccc23)cc1OCc1ccc(C(=O)NO)cc1]

(III-6) N-hydroxy-4-(2-methoxy-5-(methyl(2-methyl-4-quinazolinyl)amino)phenoxy)benzamide;

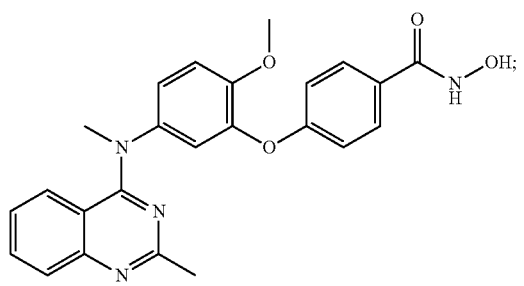 [SMILES: COc1ccc(N(C)c2nc(C)nc3ccccc23)cc1Oc1ccc(C(=O)NO)cc1]

(III-7) N-hydroxy-6-(2-methoxy-5-(methyl(2-methyl-4-quinazolinyl)amino)phenoxy)nicotinamide;

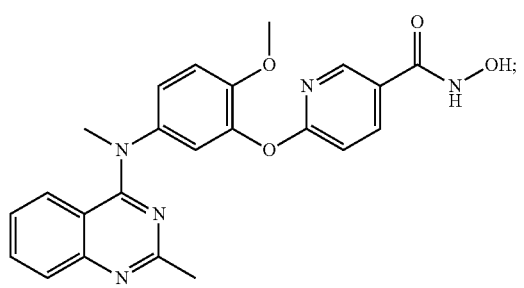 [SMILES: COc1ccc(N(C)c2nc(C)nc3ccccc23)cc1Oc1ccc(C(=O)NO)cn1]

(III-8) N-hydroxy-5-(2-methoxy-5-(methyl(2-methyl-4-quinazolinyl)amino)phenoxy)picolinamide;

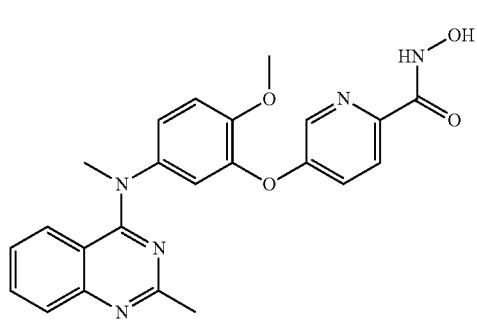 [SMILES: COc1ccc(N(C)c2nc(C)nc3ccccc23)cc1Oc1ccc(C(=O)NO)nc1]

(III-9) N-hydroxy-2-(2-methoxy-5-(methyl(2-methyl-4-quinazolinyl)amino)phenoxy)pyrimidin-5-formamide;

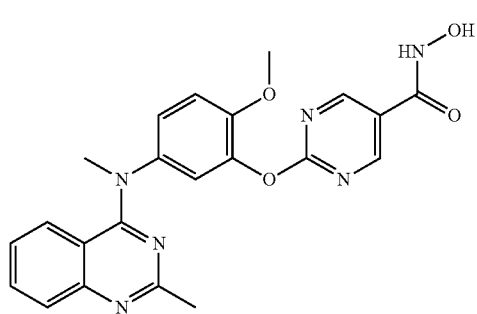 [SMILES: COc1ccc(N(C)c2nc(C)nc3ccccc23)cc1Oc1ncc(C(=O)NO)cn1]

(III-10) N-hydroxy-5-(2-methoxy-5-(methyl(2-methyl-4-quinazolinyl)amino)phenoxy)pyrimidin-2-formamide;

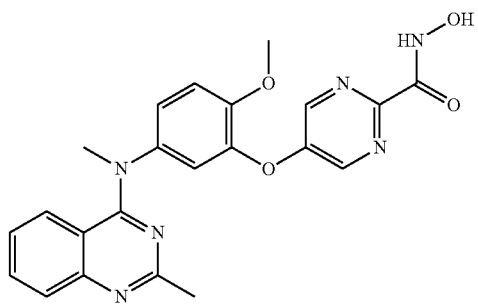

(III-11) N-hydroxy-5-(2-methoxy-5-(methyl(2-methyl-4-quinazolinyl)amino)phenoxy)pyrazin-2-formamide;

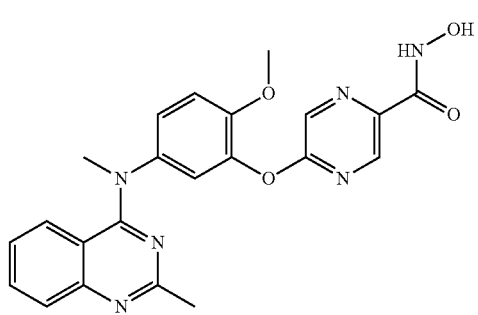 [SMILES: COc1ccc(N(C)c2nc(C)nc3ccccc23)cc1Oc1cnc(C(=O)NO)cn1]

(III-12) N-hydroxy-2-(3-(methyl(2-methyl-4-quinazolinyl)amino)phenoxy)acetamide;

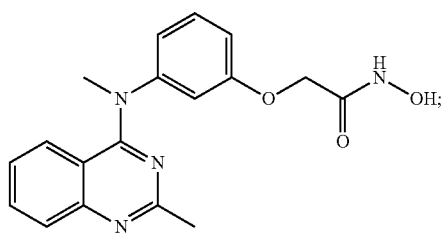 [SMILES: Cc1nc(N(C)c2cccc(OCC(=O)NO)c2)c2ccccc2n1]

(III-13) N-hydroxy-4-(3-(methyl(2-methyl-4-quinazolinyl)amino)phenoxy)butanamide;

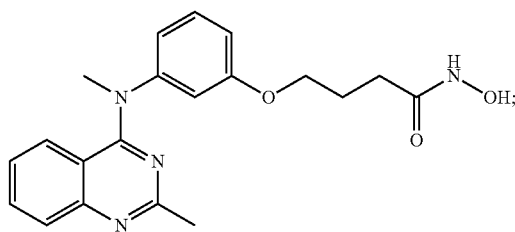 [SMILES: Cc1nc(N(C)c2cccc(OCCCC(=O)NO)c2)c2ccccc2n1]

(III-14) N-hydroxy-5-(3-(methyl(2-methyl-4-quinazolinyl)amino)phenoxy)pentanamide;

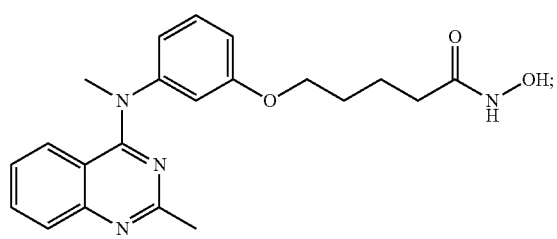 [SMILES: Cc1nc(N(C)c2cccc(OCCCCC(=O)NO)c2)c2ccccc2n1]

(III-15) N-hydroxy-6-(3-(methyl(2-methyl-4-quinazolinyl)amino)phenoxy)hexanamide;

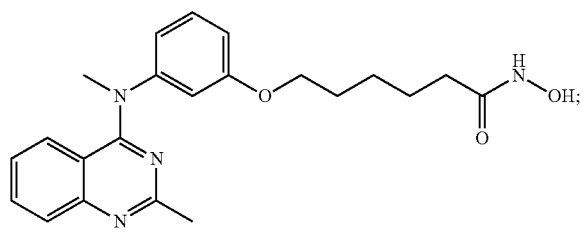 [SMILES: Cc1nc(N(C)c2cccc(OCCCCCC(=O)NO)c2)c2ccccc2n1]

(III-16) N-hydroxy-4-((3-(methyl(2-methyl-4-quinazolinyl)amino)phenoxy)methyl)benzamide;

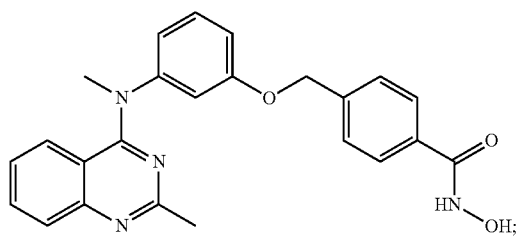 [SMILES: Cc1nc(N(C)c2cccc(OCc3ccc(C(=O)NO)cc3)c2)c2ccccc2n1]

(III-17) N-hydroxy-4-(3-(methyl(2-methyl-4-quinazolinyl)amino)phenoxy)benzamide;

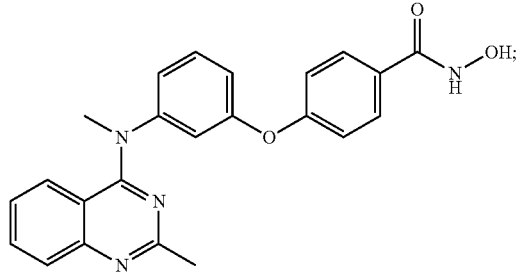 [SMILES: Cc1nc(N(C)c2cccc(Oc3ccc(C(=O)NO)cc3)c2)c2ccccc2n1]

(III-18) N-hydroxy-6-(3-(methyl(2-methyl-4-quinazolinyl)amino)phenoxy)nicotinamide;

(III-19) N-hydroxy-5-(3-(methyl(2-methyl-4-quinazolinyl)amino)phenoxy)picolinamide;

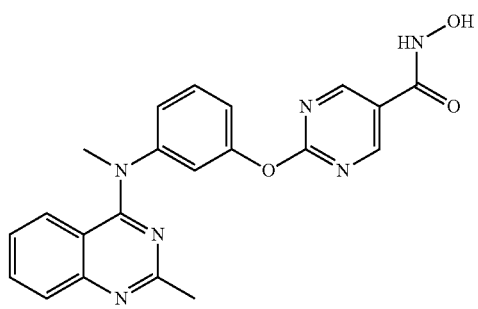 [SMILES: Cc1nc(N(C)c2cccc(Oc3ncc(C(=O)NO)cn3)c2)c2ccccc2n1]

(III-20) N-hydroxy-2-(3-(methyl(2-methyl-4-quinazolinyl)amino)phenoxy)pyrimidin-5-formamide;

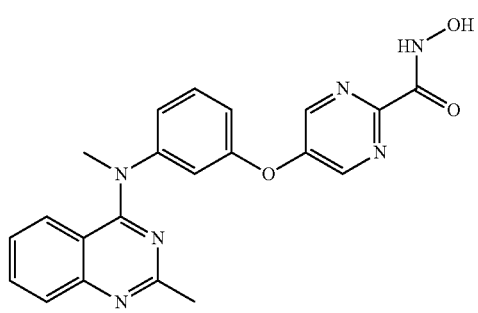 [SMILES: Cc1nc(N(C)c2cccc(Oc3cnc(C(=O)NO)nc3)c2)c2ccccc2n1]

(III-21) N-hydroxy-5-(3-(methyl(2-methyl-4-quinazolinyl)amino)phenoxy)pyrimidin-2-formamide;

and (III-22) N-hydroxy-5-(3-(methyl(2-methyl-4-quinazolinyl)amino)phenoxy)pyrazine-2-formamide;

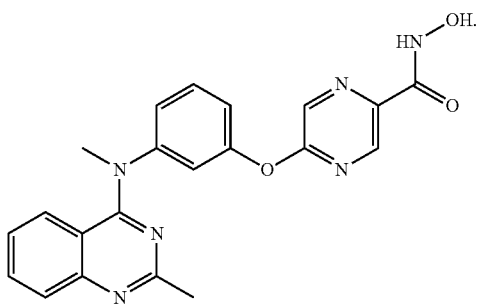 [SMILES: Cc1nc(N(C)c2cccc(Oc3cnc(C(=O)NO)cn3)c2)c2ccccc2n1]

9. The compound or pharmaceutically acceptable salts thereof according to claim 1, wherein, the compound is as shown in Formula IV:

(IV)

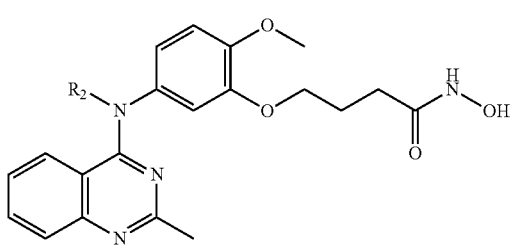

wherein, R₂ is independently hydrogen, halogen, C$_{1-6}$ alkyl, R₄O—, —NH₂, —NO₂, R₄NH—, wherein R₄ is C$_{1-10}$ alkyl or benzyl;

the pharmaceutically acceptable salts are hydrochloride, hydrobromide, sulfate, acetate, lactate, tartrate, tannate, citrate, trifluoroacetate, malate, maleate, succinate, p-toluenesulfonate or methanesulfonate.

10. A compound or pharmaceutically acceptable salts thereof selected from the following:

(IV-1)  4-(5-(ethyl(2-methyl-4-quinazolinyl)amino)-2-methoxyphenyl)-N-hydroxybutanamide;

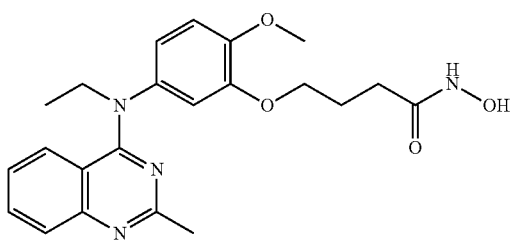 [SMILES: CCN(c1ccc(OC)c(OCCCC(=O)NO)c1)c1nc(C)nc2ccccc12]

(IV-2)  N-hydroxy-4-(2-methoxy-5-((2-methyl-4-quinazolinyl)(propyl)amino)phenoxy)butanamide;

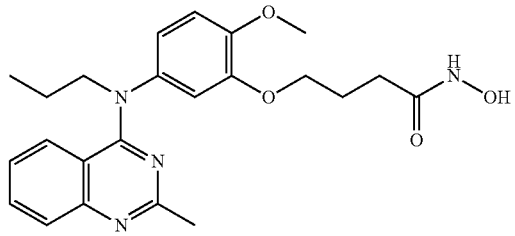 [SMILES: CCCN(c1ccc(OC)c(OCCCC(=O)NO)c1)c1nc(C)nc2ccccc12]

(IV-3)  4-(5-(butyl(2-methyl-4-quinazolinyl)amino)-2-methoxyphenyl)-N-hydroxybutanamide;

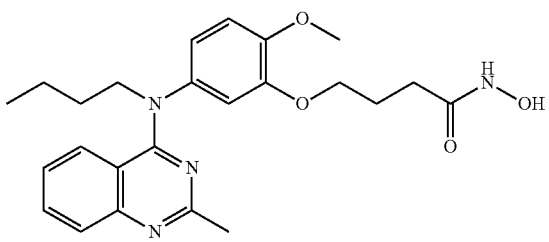 [SMILES: CCCCN(c1ccc(OC)c(OCCCC(=O)NO)c1)c1nc(C)nc2ccccc12]

(IV-4)  N-hydroxy-4-(2-methoxy-5-((2-methyl-4-quinazolinyl)(pentyl)amino)phenoxy)butanamide;

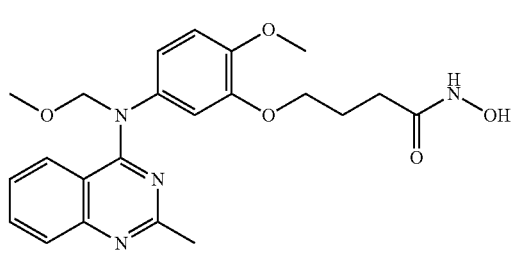 [SMILES: COCN(c1ccc(OC)c(OCCCC(=O)NO)c1)c1nc(C)nc2ccccc12]

(IV-5)  N-hydroxy-4-(2-methoxy-5-((methoxymethyl)(2-methyl-4-quinazolinyl)amino)phenoxy) butanamide;

and (IV-6)  N-hydroxy-4-(2-methoxy-5-(((methoxymethoxy)methyl)(2-methyl-4-quinazolinyl)amino) phenoxy)butanamide;

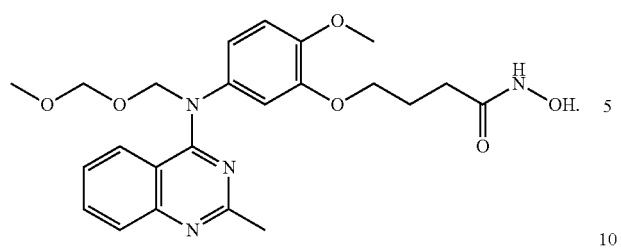

11. A pharmaceutical composition, comprising the compound or pharmaceutically acceptable salts thereof according to claim 1 and pharmaceutically acceptable excipients, wherein the pharmaceutical composition is a tablet, a suppository, a dispersible tablet, an enteric-coated tablet, a chewable tablet, an orally-disintegrating tablet, a capsule, a sugar-coating formulation, a granule, a dry powder, an oral solution, a small injection, a freeze-dried powder injection or an infusion solution; and the pharmaceutically acceptable excipients include one or more selected from the following: diluent, solubilizer, disintegrant, suspending agent, lubricant, binder, filler, correctant, sweetening agent, antioxidant, surfactant, preservative, coating agent or pigment.

* * * * *

UNITED STATES PATENT AND TRADEMARK OFFICE
CERTIFICATE OF CORRECTION

PATENT NO. : 10,532,053 B2  
APPLICATION NO. : 15/558370  
DATED : January 14, 2020  
INVENTOR(S) : Lijuan Chen et al.

Page 1 of 1

It is certified that error appears in the above-identified patent and that said Letters Patent is hereby corrected as shown below:

In the Claims

Column 109, the formula beginning at Line 12-24 reading:

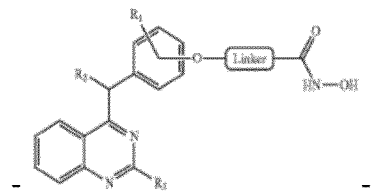

Should be read as:

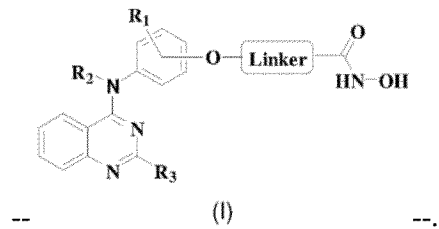

Signed and Sealed this  
Nineteenth Day of July, 2022

Katherine Kelly Vidal  
*Director of the United States Patent and Trademark Office*